United States Patent
Fung et al.

(10) Patent No.: US 9,198,664 B2
(45) Date of Patent: Dec. 1, 2015

(54) TISSUE LIGATION DEVICES AND CONTROLS THEREFOR

(75) Inventors: Gregory W. Fung, San Mateo, CA (US); Russell A. Seiber, Redwood Shores, CA (US); Eduardo Sager, Milpitas, CA (US); Gary H. Miller, Milpitas, CA (US); Maria Garcia, San Jose, CA (US); Ryan Douglas Helmuth, Saratoga, CA (US); Arnold M. Escano, Santa Clara, CA (US); Douglas Todd Ellison, Plano, TX (US); William E. Cohn, Bellaire, TX (US)

(73) Assignee: SentreHEART, Inc., Redwood City, CA (US)

( * ) Notice: Subject to any disclaimer, the term of this patent is extended or adjusted under 35 U.S.C. 154(b) by 1135 days.

(21) Appl. No.: 12/752,873

(22) Filed: Apr. 1, 2010

(65) Prior Publication Data

US 2011/0087247 A1    Apr. 14, 2011

Related U.S. Application Data

(60) Provisional application No. 61/165,828, filed on Apr. 1, 2009.

(51) Int. Cl.
  *A61B 17/04*    (2006.01)
  *A61B 17/12*    (2006.01)
  (Continued)

(52) U.S. Cl.
  CPC ....... *A61B 17/12013* (2013.01); *A61B 17/0469* (2013.01); *A61B 17/0487* (2013.01);
  (Continued)

(58) Field of Classification Search
  CPC ............. A61B 17/0469; A61B 17/12013; A61B 17/1487; A61B 17/16114; A61B 2017/00243; A61B 2017/00331; A61B 2017/0496; A61B 2017/0475; A61B 2017/00867; A61B 2017/00557; A61B 2017/003; A61B 2017/3445; A61B 2019/307; A61B 2019/4857

USPC ......... 606/113, 114, 110, 111, 139, 169, 144, 606/148, 228
  See application file for complete search history.

(56) References Cited

U.S. PATENT DOCUMENTS

| 3,496,932 A | 2/1970 | Prisk et al. |
| 3,677,597 A | 7/1972 | Stipek |

(Continued)

FOREIGN PATENT DOCUMENTS

| EP | 0 598 219 A2 | 5/1994 |
| EP | 0 598 219 A3 | 5/1994 |

(Continued)

OTHER PUBLICATIONS

Afibfacts.com (Date Unknown). "Cox-Maze III: The Gold Standard Treatment for Atrial Fibrillation: Developing a Surgical Option for Atrial Fibrillation," located at <http://www.afibfacts.com/Treatment_Options_for_Atrial_Fibrillation/Cox-Maze_III%_3a_The_Gold_Standard_Treatment_for_Atrial_Fibrillation >, last visited on Apr. 20, 2007, 4 pages.

(Continued)

*Primary Examiner* — Tuan V Nguyen
*Assistant Examiner* — Tin Nguyen
(74) *Attorney, Agent, or Firm* — Morrison & Foerster LLP

(57) ABSTRACT

Described here are devices for closing one or more tissues, and handles for controlling these devices. Generally, the devices described here comprise a snare loop assembly, wherein the snare loop assembly comprises a snare and a suture loop, and a handle for controlling the snare loop assembly. In some variations the snare loop assembly may comprise a retention member that may releasably connect the suture loop to the snare. In other variations the devices comprise one or more force-reducing suture locks to help prevent the suture loop from inadvertently disengaging from the snare loop assembly. In still other variations, the excess-suture management features. The handles described here may be configured to remove excess suture from a suture loop, and may also be configured to release the suture loop from the snare loop assembly.

11 Claims, 26 Drawing Sheets

(51) Int. Cl.
  *A61B 17/06* (2006.01)
  *A61B 17/00* (2006.01)
  *A61B 17/34* (2006.01)
  *A61B 19/00* (2006.01)

(52) U.S. Cl.
  CPC ..... *A61B17/06114* (2013.01); *A61B 2017/003* (2013.01); *A61B 2017/00243* (2013.01); *A61B 2017/00331* (2013.01); *A61B 2017/00557* (2013.01); *A61B 2017/00867* (2013.01); *A61B 2017/0475* (2013.01); *A61B 2017/0496* (2013.01); *A61B 2017/3445* (2013.01); *A61B 2019/307* (2013.01); *A61B 2019/4857* (2013.01)

(56) References Cited

U.S. PATENT DOCUMENTS

| | | |
|---|---|---|
| 3,802,074 A | 4/1974 | Hoppe |
| 3,841,685 A | 10/1974 | Kolodziej |
| 3,999,555 A | 12/1976 | Person |
| 4,018,229 A | 4/1977 | Komiya |
| 4,030,509 A | 6/1977 | Heilman et al. |
| 4,078,305 A | 3/1978 | Akiyama |
| 4,181,123 A | 1/1980 | Crosby |
| 4,249,536 A | 2/1981 | Vega |
| 4,257,278 A | 3/1981 | Papadofrangakis et al. |
| 4,319,562 A | 3/1982 | Crosby |
| 4,596,530 A | 6/1986 | McGlinn |
| 4,662,377 A | 5/1987 | Heilman et al. |
| 4,765,341 A | 8/1988 | Mower et al. |
| 4,817,608 A | 4/1989 | Shapland et al. |
| 4,901,405 A | 2/1990 | Grover et al. |
| 4,944,753 A | 7/1990 | Burgess et al. |
| 4,991,578 A | 2/1991 | Cohen |
| 4,991,603 A | 2/1991 | Cohen et al. |
| 4,998,975 A | 3/1991 | Cohen et al. |
| 5,033,477 A | 7/1991 | Chin et al. |
| 5,108,406 A | 4/1992 | Lee |
| 5,163,942 A | 11/1992 | Rydell |
| 5,163,946 A | 11/1992 | Li |
| 5,176,691 A | 1/1993 | Pierce |
| 5,181,123 A | 1/1993 | Swank |
| 5,226,535 A | 7/1993 | Rosdhy et al. |
| 5,226,908 A | 7/1993 | Yoon |
| 5,242,459 A | 9/1993 | Buelna |
| 5,243,977 A | 9/1993 | Trabucco et al. |
| 5,269,326 A | 12/1993 | Verrier |
| 5,281,238 A | 1/1994 | Chin et al. |
| 5,300,078 A | 4/1994 | Buelna |
| 5,306,234 A | 4/1994 | Johnson |
| 5,318,578 A | 6/1994 | Hasson |
| 5,336,229 A | 8/1994 | Noda |
| 5,336,252 A | 8/1994 | Cohen |
| 5,385,156 A | 1/1995 | Oliva |
| 5,387,219 A | 2/1995 | Rappe |
| 5,403,331 A | 4/1995 | Chesterfield et al. |
| 5,405,351 A | 4/1995 | Kinet et al. |
| 5,417,684 A | 5/1995 | Jackson et al. |
| 5,423,821 A | 6/1995 | Pasque |
| 5,423,830 A | 6/1995 | Schneebaum et al. |
| 5,433,457 A | 7/1995 | Wright |
| 5,433,730 A | 7/1995 | Alt |
| 5,443,481 A | 8/1995 | Lee |
| 5,449,367 A | 9/1995 | Kadry |
| 5,494,240 A | 2/1996 | Waugh |
| 5,498,228 A | 3/1996 | Royalty et al. |
| 5,540,711 A | 7/1996 | Kieturakis et al. |
| 5,571,161 A | 11/1996 | Starksen |
| 5,591,177 A | 1/1997 | Lehrer |
| 5,609,597 A | 3/1997 | Lehrer |
| 5,624,430 A | 4/1997 | Eton et al. |
| 5,624,453 A | 4/1997 | Ahmed |
| 5,634,895 A | 6/1997 | Igo et al. |
| 5,676,162 A | 10/1997 | Larson, Jr. et al. |
| 5,676,651 A | 10/1997 | Larson, Jr. et al. |
| 5,678,547 A | 10/1997 | Faupel et al. |
| 5,681,278 A | 10/1997 | Igo et al. |
| 5,682,906 A | 11/1997 | Sterman et al. |
| 5,683,364 A | 11/1997 | Zadini et al. |
| 5,683,445 A | 11/1997 | Swoyer |
| 5,693,059 A | 12/1997 | Yoon |
| 5,693,091 A | 12/1997 | Larson, Jr. et al. |
| 5,699,748 A | 12/1997 | Linskey, Jr. et al. |
| 5,702,430 A | 12/1997 | Larson, Jr. et al. |
| 5,707,336 A | 1/1998 | Rubin |
| 5,716,367 A | 2/1998 | Koike et al. |
| 5,716,392 A | 2/1998 | Bourgeois et al. |
| 5,727,569 A | 3/1998 | Benetti et al. |
| 5,728,151 A | 3/1998 | Garrison et al. |
| 5,735,877 A | 4/1998 | Pagedas |
| 5,741,281 A * | 4/1998 | Martin .................. 606/148 |
| 5,752,526 A | 5/1998 | Cosgrove |
| 5,766,151 A | 6/1998 | Valley et al. |
| 5,766,216 A | 6/1998 | Gangal et al. |
| 5,766,217 A | 6/1998 | Christy |
| 5,769,863 A | 6/1998 | Garrison |
| 5,779,727 A | 7/1998 | Orejola |
| 5,792,151 A | 8/1998 | Heck et al. |
| 5,797,870 A | 8/1998 | March et al. |
| 5,797,929 A | 8/1998 | Andreas et al. |
| 5,797,946 A | 8/1998 | Chin |
| 5,799,661 A | 9/1998 | Boyd et al. |
| 5,810,845 A | 9/1998 | Yoon |
| 5,823,946 A | 10/1998 | Chin |
| 5,827,216 A | 10/1998 | Igo et al. |
| 5,840,059 A | 11/1998 | March et al. |
| 5,855,586 A | 1/1999 | Habara et al. |
| 5,865,791 A | 2/1999 | Whayne et al. |
| 5,871,531 A | 2/1999 | Struble |
| 5,873,876 A | 2/1999 | Christy |
| 5,879,375 A | 3/1999 | Larson, Jr. et al. |
| 5,882,299 A | 3/1999 | Rastegar et al. |
| 5,893,869 A | 4/1999 | Barnhart et al. |
| 5,895,298 A | 4/1999 | Faupel et al. |
| 5,897,586 A | 4/1999 | Molina |
| 5,900,433 A | 5/1999 | Igo et al. |
| 5,906,620 A | 5/1999 | Nakao et al. |
| 5,908,429 A | 6/1999 | Yoon |
| 5,908,435 A | 6/1999 | Samuels |
| 5,910,124 A | 6/1999 | Rubin |
| 5,910,129 A | 6/1999 | Koblish et al. |
| 5,921,994 A | 7/1999 | Andreas et al. |
| 5,924,424 A | 7/1999 | Stevens et al. |
| RE36,269 E | 8/1999 | Wright |
| 5,941,819 A | 8/1999 | Chin |
| 5,961,440 A | 10/1999 | Schweich, Jr. et al. |
| 5,964,699 A | 10/1999 | Rullo et al. |
| 5,968,010 A | 10/1999 | Waxman et al. |
| 5,972,013 A | 10/1999 | Schmidt |
| 5,984,866 A | 11/1999 | Rullo et al. |
| 5,984,917 A | 11/1999 | Fleischman et al. |
| 5,991,668 A | 11/1999 | Leinders et al. |
| 5,997,525 A | 12/1999 | March et al. |
| 6,006,122 A | 12/1999 | Smits |
| 6,010,531 A | 1/2000 | Donlon et al. |
| 6,015,382 A | 1/2000 | Zwart et al. |
| 6,045,570 A | 4/2000 | Epstein et al. |
| 6,048,329 A | 4/2000 | Thompson et al. |
| 6,059,750 A | 5/2000 | Fogarty et al. |
| 6,067,942 A | 5/2000 | Fernandez |
| 6,071,281 A | 6/2000 | Burnside et al. |
| 6,081,738 A | 6/2000 | Hinohara et al. |
| 6,083,153 A | 7/2000 | Rullo et al. |
| 6,090,042 A | 7/2000 | Rullo et al. |
| 6,095,968 A | 8/2000 | Snyders |
| 6,110,170 A | 8/2000 | Taylor et al. |
| 6,120,431 A | 9/2000 | Magovern et al. |
| 6,132,438 A | 10/2000 | Fleischman et al. |
| 6,148,230 A | 11/2000 | KenKnight |
| 6,149,595 A | 11/2000 | Seitz et al. |
| 6,152,144 A | 11/2000 | Lesh et al. |
| 6,152,920 A | 11/2000 | Thompson et al. |
| 6,152,936 A | 11/2000 | Christy et al. |

(56) References Cited

U.S. PATENT DOCUMENTS

| | | |
|---|---|---|
| 6,155,968 A | 12/2000 | Wilk |
| 6,157,852 A | 12/2000 | Selmon et al. |
| 6,161,543 A | 12/2000 | Cox et al. |
| 6,162,195 A | 12/2000 | Igo et al. |
| 6,167,889 B1 | 1/2001 | Benetti |
| 6,199,556 B1 | 3/2001 | Benetti et al. |
| 6,200,303 B1 | 3/2001 | Verrior et al. |
| 6,206,004 B1 | 3/2001 | Schmidt et al. |
| 6,224,584 B1 | 5/2001 | March et al. |
| 6,231,518 B1 | 5/2001 | Grabek et al. |
| 6,237,605 B1 | 5/2001 | Vaska et al. |
| 6,241,667 B1 | 6/2001 | Vetter et al. |
| 6,258,021 B1 | 7/2001 | Wilk |
| 6,266,550 B1 | 7/2001 | Selmon et al. |
| 6,280,415 B1 | 8/2001 | Johnson |
| 6,283,127 B1 | 9/2001 | Sterman et al. |
| 6,290,674 B1 | 9/2001 | Roue et al. |
| 6,293,906 B1 | 9/2001 | Vanden Hoek et al. |
| 6,296,630 B1 | 10/2001 | Altman et al. |
| 6,311,692 B1 | 11/2001 | Vaska et al. |
| 6,311,693 B1 | 11/2001 | Sterman et al. |
| 6,314,962 B1 | 11/2001 | Vaska et al. |
| 6,314,963 B1 | 11/2001 | Vaska et al. |
| 6,319,201 B1 | 11/2001 | Wilk |
| 6,333,347 B1 | 12/2001 | Hunter et al. |
| 6,346,074 B1 | 2/2002 | Roth |
| 6,379,366 B1 | 4/2002 | Fleischman et al. |
| 6,423,051 B1 | 7/2002 | Kaplan et al. |
| 6,474,340 B1 | 11/2002 | Vaska et al. |
| 6,485,407 B2 | 11/2002 | Alferness et al. |
| 6,488,689 B1 | 12/2002 | Kaplan et al. |
| 6,494,211 B1 | 12/2002 | Boyd et al. |
| 6,551,303 B1 | 4/2003 | Van Tassel et al. |
| 6,561,969 B2 | 5/2003 | Frazier et al. |
| 6,592,552 B1 | 7/2003 | Schmidt |
| 6,610,055 B1 | 8/2003 | Swanson et al. |
| 6,610,072 B1 | 8/2003 | Christy et al. |
| 6,613,062 B1 | 9/2003 | Leckrone et al. |
| 6,632,229 B1 | 10/2003 | Yamanouchi |
| 6,652,555 B1 | 11/2003 | Van Tassel et al. |
| 6,656,175 B2 | 12/2003 | Francischelli et al. |
| 6,666,861 B1 | 12/2003 | Grabek |
| 6,692,491 B1 | 2/2004 | Phan |
| 6,733,509 B2 | 5/2004 | Nobles et al. |
| 6,736,774 B2 | 5/2004 | Benetti et al. |
| 6,755,338 B2 | 6/2004 | Hahnen et al. |
| 6,786,898 B2 | 9/2004 | Guenst |
| 6,789,509 B1 | 9/2004 | Motsinger |
| 6,830,174 B2 | 12/2004 | Hillstead et al. |
| 6,830,576 B2 | 12/2004 | Fleischman et al. |
| 6,985,776 B2 | 1/2006 | Kane et al. |
| 7,011,671 B2 | 3/2006 | Welch |
| 7,041,111 B2 | 5/2006 | Chu |
| 7,056,294 B2 | 6/2006 | Khairkhahan et al. |
| 7,063,682 B1 | 6/2006 | Whayne et al. |
| 7,063,693 B2 | 6/2006 | Guenst |
| 7,175,619 B2 | 2/2007 | Koblish et al. |
| 7,186,214 B2 | 3/2007 | Ness |
| 7,207,988 B2 | 4/2007 | Leckrone et al. |
| 7,226,440 B2 | 6/2007 | Gelfand et al. |
| 7,226,458 B2 | 6/2007 | Kaplan et al. |
| 7,264,587 B2 | 9/2007 | Chin |
| 7,294,115 B1 | 11/2007 | Wilk |
| 7,297,144 B2 | 11/2007 | Fleischman et al. |
| 7,309,328 B2 | 12/2007 | Kaplan et al. |
| 7,318,829 B2 | 1/2008 | Kaplan et al. |
| 7,326,221 B2 | 2/2008 | Sakamoto et al. |
| 7,331,979 B2 | 2/2008 | Khosravi et al. |
| 7,473,260 B2 | 1/2009 | Opolski et al. |
| 7,608,091 B2 | 10/2009 | Goldfarb et al. |
| 7,618,425 B2 | 11/2009 | Yamamoto et al. |
| 7,722,641 B2 | 5/2010 | van der Burg et al. |
| 7,828,810 B2 | 11/2010 | Liddicoat et al. |
| 7,846,168 B2 | 12/2010 | Liddicoat et al. |
| 7,905,900 B2 | 3/2011 | Palermo et al. |
| 7,918,865 B2 | 4/2011 | Liddicoat et al. |
| 8,105,342 B2 | 1/2012 | Onuki et al. |
| 8,157,818 B2 | 4/2012 | Gartner et al. |
| 8,287,561 B2 | 10/2012 | Nunez et al. |
| 8,469,983 B2 | 6/2013 | Fung et al. |
| 8,636,767 B2 | 1/2014 | McClain |
| 8,771,297 B2 | 7/2014 | Miller et al. |
| 8,795,297 B2 | 8/2014 | Liddicoat et al. |
| 2001/0025132 A1 | 9/2001 | Alferness et al. |
| 2002/0017306 A1 | 2/2002 | Cox et al. |
| 2002/0022860 A1 | 2/2002 | Borillo et al. |
| 2002/0049457 A1 | 4/2002 | Kaplan et al. |
| 2002/0058925 A1 | 5/2002 | Kaplan et al. |
| 2002/0062136 A1 | 5/2002 | Hillstead et al. |
| 2002/0068970 A1 | 6/2002 | Cox et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111636 A1 | 8/2002 | Fleischman et al. |
| 2002/0111637 A1 | 8/2002 | Kaplan et al. |
| 2003/0014049 A1 | 1/2003 | Koblish et al. |
| 2003/0024537 A1 | 2/2003 | Cox et al. |
| 2003/0045900 A1 | 3/2003 | Hahnen et al. |
| 2003/0069577 A1 | 4/2003 | Vaska et al. |
| 2003/0083542 A1 | 5/2003 | Alferness et al. |
| 2003/0083674 A1 | 5/2003 | Gibbens, III |
| 2003/0109863 A1 | 6/2003 | Francischelli et al. |
| 2003/0120264 A1 | 6/2003 | Lattouf |
| 2003/0158464 A1 | 8/2003 | Bertolero |
| 2003/0181942 A1 | 9/2003 | Sutton et al. |
| 2003/0187460 A1 | 10/2003 | Chin et al. |
| 2003/0236535 A1 | 12/2003 | Onuki et al. |
| 2004/0030335 A1 | 2/2004 | Zenati et al. |
| 2004/0034347 A1 | 2/2004 | Hall et al. |
| 2004/0044361 A1 | 3/2004 | Frazier et al. |
| 2004/0049210 A1 | 3/2004 | VanTassel et al. |
| 2004/0059352 A1* | 3/2004 | Burbank et al. ............... 606/148 |
| 2004/0064138 A1 | 4/2004 | Grabek |
| 2004/0078069 A1 | 4/2004 | Francischelli et al. |
| 2004/0102804 A1 | 5/2004 | Chin |
| 2004/0106918 A1 | 6/2004 | Cox et al. |
| 2004/0111101 A1 | 6/2004 | Chin |
| 2004/0116943 A1 | 6/2004 | Brandt et al. |
| 2004/0162579 A1* | 8/2004 | Foerster ..................... 606/228 |
| 2004/0225212 A1 | 11/2004 | Okerlund et al. |
| 2004/0225300 A1 | 11/2004 | Goldfarb et al. |
| 2004/0243176 A1 | 12/2004 | Hahnen et al. |
| 2004/0260273 A1 | 12/2004 | Wan |
| 2005/0033280 A1 | 2/2005 | Francischelli et al. |
| 2005/0033287 A1 | 2/2005 | Sra |
| 2005/0033321 A1 | 2/2005 | Fleischman et al. |
| 2005/0043745 A1 | 2/2005 | Alferness et al. |
| 2005/0085843 A1 | 4/2005 | Opolski et al. |
| 2005/0107824 A1 | 5/2005 | Hillstead et al. |
| 2005/0149068 A1 | 7/2005 | Williams et al. |
| 2005/0149069 A1 | 7/2005 | Bertolero et al. |
| 2005/0154376 A1 | 7/2005 | Riviere et al. |
| 2005/0154404 A1 | 7/2005 | Liddicoat |
| 2005/0165466 A1 | 7/2005 | Morris et al. |
| 2005/0256532 A1 | 11/2005 | Nayak et al. |
| 2006/0004323 A1 | 1/2006 | Chang et al. |
| 2006/0004388 A1 | 1/2006 | Whayne et al. |
| 2006/0009715 A1 | 1/2006 | Khairkhahan et al. |
| 2006/0020162 A1 | 1/2006 | Whayne et al. |
| 2006/0020271 A1 | 1/2006 | Stewart et al. |
| 2006/0020336 A1 | 1/2006 | Liddicoat |
| 2006/0034930 A1 | 2/2006 | Khosravi et al. |
| 2006/0100545 A1 | 5/2006 | Ayala et al. |
| 2006/0200169 A1 | 9/2006 | Sniffin |
| 2006/0212045 A1 | 9/2006 | Schilling et al. |
| 2006/0247672 A1 | 11/2006 | Vidlund et al. |
| 2006/0253128 A1 | 11/2006 | Sekine et al. |
| 2006/0253129 A1 | 11/2006 | Liddicoat et al. |
| 2007/0016228 A1 | 1/2007 | Salas |
| 2007/0027456 A1 | 2/2007 | Gartner et al. |
| 2007/0060951 A1 | 3/2007 | Shannon |
| 2007/0073313 A1 | 3/2007 | Liddicoat et al. |
| 2007/0083082 A1 | 4/2007 | Kiser et al. |
| 2007/0083225 A1 | 4/2007 | Kiser et al. |

(56) References Cited

U.S. PATENT DOCUMENTS

| | | |
|---|---|---|
| 2007/0083232 A1 | 4/2007 | Lee |
| 2007/0088369 A1 | 4/2007 | Shaw et al. |
| 2007/0100405 A1 | 5/2007 | Thompson et al. |
| 2007/0135822 A1 | 6/2007 | Onuki et al. |
| 2007/0149988 A1 | 6/2007 | Michler et al. |
| 2007/0179345 A1 | 8/2007 | Santilli |
| 2007/0249991 A1 | 10/2007 | Whayne et al. |
| 2007/0260278 A1 | 11/2007 | Wheeler et al. |
| 2007/0270637 A1* | 11/2007 | Takemoto et al. ............ 600/104 |
| 2007/0270891 A1 | 11/2007 | McGuckin, Jr. |
| 2008/0009843 A1 | 1/2008 | de la Torre |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0097489 A1 | 4/2008 | Goldfarb et al. |
| 2008/0147097 A1 | 6/2008 | Liddicoat et al. |
| 2008/0221593 A1 | 9/2008 | Liddicoat et al. |
| 2008/0228265 A1 | 9/2008 | Spence et al. |
| 2008/0243183 A1 | 10/2008 | Miller et al. |
| 2008/0294174 A1 | 11/2008 | Bardsley et al. |
| 2008/0294175 A1 | 11/2008 | Bardsley et al. |
| 2008/0312664 A1 | 12/2008 | Bardsley et al. |
| 2009/0043317 A1 | 2/2009 | Cavanaugh et al. |
| 2009/0082797 A1 | 3/2009 | Fung et al. |
| 2009/0143791 A1 | 6/2009 | Miller et al. |
| 2009/0157118 A1 | 6/2009 | Miller et al. |
| 2010/0069925 A1 | 3/2010 | Friedman et al. |
| 2010/0174296 A1 | 7/2010 | Vakharia et al. |
| 2011/0144660 A1 | 6/2011 | Liddicoat et al. |
| 2013/0144311 A1 | 6/2013 | Fung et al. |

FOREIGN PATENT DOCUMENTS

| | | |
|---|---|---|
| EP | 0 598 219 B1 | 5/1994 |
| EP | 1 010 397 A1 | 6/2000 |
| GB | 1 506 142 A | 4/1978 |
| JP | 7-296645 A2 | 11/1995 |
| JP | 7-299073 A | 11/1995 |
| JP | 11-507262 A | 6/1999 |
| JP | 2001-120560 A | 5/2001 |
| JP | 2002-540901 A | 12/2002 |
| JP | 2003-225241 A | 8/2003 |
| JP | 2004-000601 A | 1/2004 |
| JP | 2005-110860 A | 4/2005 |
| JP | 2005-296645 A | 10/2005 |
| JP | 2005-531360 A | 10/2005 |
| JP | 2007-504886 A | 3/2007 |
| WO | WO-94/01045 A1 | 1/1994 |
| WO | WO-94/04079 A1 | 3/1994 |
| WO | WO-94/08514 A1 | 4/1994 |
| WO | WO-96/40356 A1 | 12/1996 |
| WO | WO-97/11644 A1 | 4/1997 |
| WO | WO-97/43957 A1 | 11/1997 |
| WO | WO-00/61202 A1 | 10/2000 |
| WO | WO-2004/002327 A1 | 1/2004 |
| WO | WO-2004/066828 A2 | 8/2004 |
| WO | WO-2004/066828 A3 | 8/2004 |
| WO | WO-2005/034767 A1 | 4/2005 |
| WO | WO-2005/034767 C2 | 4/2005 |
| WO | WO-2005/034802 A2 | 4/2005 |
| WO | WO-2005/034802 A3 | 4/2005 |
| WO | WO-2006/110734 A2 | 10/2006 |
| WO | WO-2006/115689 A1 | 11/2006 |
| WO | WO-2007/056502 A1 | 5/2007 |
| WO | WO-2008/036408 A2 | 3/2008 |
| WO | WO-2008/036408 A3 | 3/2008 |
| WO | WO-2008/091612 A2 | 7/2008 |
| WO | WO-2008/091612 A3 | 7/2008 |
| WO | WO-2008/121278 A2 | 10/2008 |
| WO | WO-2009/039191 A2 | 3/2009 |
| WO | WO-2009/094237 A1 | 7/2009 |
| WO | WO-2010/006061 A2 | 1/2010 |
| WO | WO-2010/006061 A3 | 1/2010 |
| WO | WO-2010/048141 A2 | 4/2010 |
| WO | WO-2010/048141 A3 | 4/2010 |
| WO | WO-2010/110530 A1 | 10/2010 |

OTHER PUBLICATIONS

Al-Saady, N.M. et al. (1999). "Left Atrial Appendage: Structure, Function, and Role in Thromboembolism," *Heart* 82:547-554.

Albers, G.W. (Jul. 11, 1994). "Atrial Fibrillation and Stroke: Three New Studies, Three Remaining Questions," *Arch Intern Med* 154:1443-1448.

Alonso, M. et al. (Mar. 4, 2003). "Complications With Femoral Access in Cardiac Catheterization. Impact of Previous Systematic Femoral Angiography and Hemostasis With VasoSeal-Es® Collagen Plug," *Rev. Esp. Cardiol.* 56(6):569-577.

Aronow, W.S. et al. (Apr. 2009). "Atrial Fibrillation: The New Epidemic of the Age-ing World," *Journal of Atrial Fibrillation* 1(6):337-361.

Babaliaros, V.C. et al. (Jun. 3, 2008). "Emerging Applications for Transseptal Left Heart Catheterization: Old Techniques for New Procedures," *Journal of the American College of Cardiology* 51(22):2116-2122.

Bath, P.M.W. et al. (2005). "Current Status of Stroke Prevention in Patients with Atrial Fibrillation," *European Heart Journal Supplements* 7(Supplement C):C12-C18.

Benjamin, B.A. et al. (1994). "Effect of Bilateral Atrial Appendectomy on Postprandial Sodium Excretion in Conscious Monkeys," *Society for Experimental Biology and Medicine* 2006:1 page.

Beygui, F. et al. (2005, e-pub. Oct. 21, 2005). "Multimodality Imaging of Percutaneous Closure of the Left Atrial Appendage," *Clinical Vignette*, 1 page.

Bisleri, G. et al. (Jun. 3, 2005). "Innovative Monolateral Approach for Closed-Chest Atrial Fibrillation Surgery," *The Annals of Thoracic Surgery* 80:e22-e25.

Björk, V.O. et al. (Aug. 1961). "Sequelae of Left Ventricular Puncture with Angiocardiography," *Circulation* 24:204-212.

Blackshear, J.L. et al. (Feb. 1996). "Appendage Obliteration to Reduce Stroke in Cardiac Surgical Patients With Atrial Fibrillation," *Ann. Thorac. Surg.* 61(2), 13 pages.

Blackshear, J.L. et al. (Oct. 1, 2003). "Thorascopic Extracardiac Obliteration of the Left Atrial Appendage for Stroke Risk Reduction in Atrial Fibrillation," *J. Am. Coll. Cardiol.* 42(7):1249-1252.

Bonanomi, G. et al. (Jan. 1, 2003). "Left Atrial Appendectomy and Maze," *Journal of the American College of Cardiology* 41(1):169-171.

Bonow, R.O. et al. (1998). "Guidelines for the Management of Patients With Valvular Heart Disease: Executive Summary: A Report of the American College of Cardiology/American Heart Association Task Force on Practice Guidelines (Committee on Management of Patients With Valvular Heart Disease)," *Journal of the American Heart Association* 98:1949-1984.

Botham, R.J. et al. (May 1959). "Pericardial Tamponade Following Percutaneous Left Ventricular Puncture," *Circulation* 19:741-744.

Brock, R. et al. (1956). "Percutaneous Left Ventricular Puncture in the Assessment of Aortic Stenosis," *Thorax* 11:163-171.

Burke, R.P. et al. (1992). "Improved Surgical Approach to Left Atrial Appendage Aneurysm," *Journal of Cardiac Surgery* 7(2):104-107.

Canaccord Adams (Aug. 11, 2008). "A-Fib: Near a Tipping Point," 167 pages.

Chung, M.K. (Jul. 2003). "Current Clinical Issues in Atrial Fibrillation," *Cleveland Clinic Journal of Medicine* 70(Supp. 3):S6-S11.

Coffin, L.H. (Jun. 1985). "Use of the Surgical Stapler to Obliterate the Left Atrial Appendage," *Surgery, Gynecology & Obstetric* 160:565-566.

Connolly, S.J. (Sep. 7, 1999). "Preventing Stroke in Atrial Fibrillation: Why Are So Many Eligible Patients Not Receiving Anticoagulant Therapy?" *Canadian Medical Association* 161(5):533-534.

Costa, R. et al. (2006). "Bi-Atrial Subxiphoid Epicardial Pacemaker in Superior Vena Cava Syndrome," *Arq. Bras. Cardiol.* 87:e45-e47.

Cox, J.L. et al. (Apr. 1991). "The Surgical Treatment of Atrial Fibrillation: IV. Surgical Technique," *J. Thorac. Cardiovasc. Surg.* 101(4):584-592.

(56) References Cited

OTHER PUBLICATIONS

Cox, J.L. et al. (Aug. 1995). "Modification of the Maze Procedure for Atrial Flutter and Atrial Fibrillation I. Rationale and Surgical Results," *J. Thorac. Cardiovasc. Surg.* 110(2):473-484.

Cox, J.L. et al. (Aug. 1995). "Modification of the Maze Procedure for Atrial Flutter and Atrial Fibrillation II. Surgical Technique of the Maze III Procedure," *J. Thorac. Cardiovasc. Surg.* 110(2):485-495.

Cox, J.L. et al. (Nov. 1999). "Impact of the Maze Procedure on the Stroke Rate in Patients with Atrial Fibrillation," *J. Thorac. Cardiovasc. Surg.* 118:833-840.

Cox, J.L. et al. (2004). "The Role of Surgical Intervention in the Management of Atrial Fibrillation," *Texas Heart Institute Journal* 31(3):257-265.

Crystal, E. et al. (Jan. 2003). "Left Atrial Appendage Occlusion Study (LAAOS): A Randomized Clinical Trial of Left Atrial Appendage Occlusion During Routine Coronary Artery Bypass Graft Surgery for Long-term Stroke Prevention," *Am Heart J* 145(1):174-178.

D'Avila, A. et al. (Apr. 2003). "Pericardial Anatomy for the Interventional Electrophysiologist," *Journal of Cardiovascular Electrophysiology* 14(4):422-430.

D'Avila, A. et al. (Nov. 2007). "Experimental Efficacy of Pericardial Instillation of Anti-inflammatory Agents During Percutaneous Epicardial Catheter Ablation to Prevent Postprocedure Pericarditis," *Journal of Cardiovascular Electrophysiology* 18(11):1178-1183.

Demaria, A.N. et al. (Dec. 17, 2003). "Highlights of the Year JACC 2003," *Journal of the American College of Cardiology* 42(12):2156-2166.

Deneu, S. et al. (Jul. 11, 1999). "Catheter Entrapment by Atrial Suture During Minimally Invasive Port-access Cardiac Surgery," *Canadian Journal of Anesthesia* 46(10):983-986.

Deponti, R. et al. (Mar. 7, 2006). "Trans-Septal Catheterization in the Electrophysiology Laboratory: Data From a Multicenter Survey Spanning 12 Years," *Journal of the American College of Cardiology* 47(5):1037-1042.

Donal, E. et al. (Sep. 2005). "The Left Atrial Appendage, a Small, Blind-Ended Structure: A Review of Its Echocardiographic Evaluation and Its Clinical Role," *Chest* 128(3):1853-1862.

Donnino, R. et al. (2007). "Left Atrial Appendage Thrombus Outside of a 'Successful' Ligation," *European Journal of Echocardiography* pp. 1-2.

Dullum, M.K.C. et al. (1999). "Xyphoid MIDCAB: Report of the Technique and Experience with a Less Invasive MIDCAB Procedure," *Heart Surgery Forum* 2(1):77-81.

Feinberg, W.M. et al. (Mar. 13, 1995). "Prevalence, Age Distribution, and Gender of Patients With Atrial Fibrillation," *Arch Intern Med* 155:469-473.

Fieguth, H.G. et al. (1997). "Inhibition of Atrial Fibrillation by Pulmonary Vein Isolation and Auricular Resection-Experimental Study in a Sheep Model," *European Journal of Cardio-Thoracic Surgery* 11:714-721.

Final Office Action mailed on Jun. 22, 2009, for U.S. Appl. No. 10/963,371, filed on Oct. 11, 2004, 11 pages.

Final Office Action mailed on Apr. 14, 2010, for U.S. Appl. No. 11/600,671, filed on Nov. 15, 2006, 7 pages.

Final Office Action mailed on Jul. 21, 2010, for U.S. Appl. No. 11/400,714, filed on Apr. 7, 2006, 10 pages.

Fisher, D.C. et al. (Dec. 1998). "Large Gradient Across a Partially Ligated Left Atrial Appendage," *Journal of the American Society of Echocardiography* 11(12):1163-1165.

Friberg, L. et al. (2006). "Stroke Prophylaxis in Atrial Fibrillation: Who Gets it and Who Does Not?" *European Heart Journal* 27:1954-1964.

Friedman, P.A. et al. (Aug. 2009). "Percutaneous Epicardial Left Atrial Appendage Closure: Preliminary Results of an Electrogram Guided Approach," *Journal of Cardiovascular Electrophysiology* 20(8):908-915.

Fuster, V. et al. (Oct. 2001). "ACC/AHA/ESC Guidelines for the Management of Patients with Atrial Fibrillation," *European Heart Journal* 22(20):1852-1923.

Garcia-Fernandez, M.A. et al. (Oct. 1, 2003). "Role of Left Atrial Appendage Obliteration in Stroke Reduction in Patients With Mitral Valve Prosthesis," *Journal of the American College of Cardiology* 42(7):1253-1258.

Gardiner, G.A. Jr. et al. (Apr. 1986). "Complications of Transluminal Angioplasty," *Radiology* 159:201-208.

Gillinov, A.M. (2007). "Advances in Surgical Treatment of Atrial Fibrillation," *Stroke* 38(part 2):618-623.

Gilman, R.A. et al. (Apr. 1963). "Direct Left Ventricular Puncture," *California Medicine* 98(4):200-203.

Goodwin, W.E. et al. (Nov. 1950). "Translumbar Aortic Puncture and Retrograde Catheterization of the Aorta in Aortography and Renal Arteriography," *Annals of Surgery* 132(5):944-958.

Gottlieb, L.K. et al. (Sep. 12, 1994). "Anticoagulation in Atrial Fibrillation," *Arch Intern Med.* 154:1945-1953.

Graffigna, A. et al. (1993). "Surgical Treatment of Wolff-Parkinson-White Syndrome: Epicardial Approach Without the Use of Cardiopulmonary Bypass," *J. Card. Surg.* 8:108-116.

Haissaguerre, M. et al. (Nov. 2005). "Catheter Ablation of Long-Lasting Persistent Atrial Fibrillation: Clinical Outcome and Mechanisms of Subsequent Arrhythmias," *Journal of Cardiovascular Electrophysiology* 16(11):1138-1147.

Halperin, J.L. et al. (Aug. 1988). "Atrial Fibrillation and Stroke: New Ideas, Persisting Dilemmas," *Journal of the American Heart Association* 19(8):937-941.

Halperin, J.L. et al. (Oct. 1, 2003). "Obliteration of the Left Atrial Appendage for Prevention of Thromboembolism," *Journal of the American College of Cardiology* 42(7):1259-1261.

Hammill, S.C. (May 2006). "Epicardial Ablation: Reducing the Risks," *J. Cardiovasc. Electrophysiol.* 17:550-552.

Hara, H. et al. (Jan. 2008). "Percutaneous Left Atrial Appendage Obliteration," *JACC: Cardiovascular Imagin* 1(1):92-93.

Hart, R.G. et al. (Nov. 2, 1999). "Atrial Fibrillation and Thromboembolism: A Decade of Progress in Stroke Prevention," *Annals of Internal Medicine* 131(9):688-695.

Hart, R.G. et al. (2001). "Atrial Fibrillation and Stroke: Concepts and Controversies," *Stroke* 32:803-808.

Hart, R.G. (Sep. 11, 2003). "Atrial Fibrillation and Stroke Prevention," *The New England Journal of Medicine* 349(11):1015-1016.

Healey, J.S. et al. (Oct. 2003). "Surgical Closure of the Left Atrial Appendage for the Prevention of Stroke: A Randomized Pilot Trial of Safety and Efficacy (The Left Atrial Appendage Occlusion Study—LAAOS)," presented at The Canadian Cardiovascular Congress 2003, Toronot, Canada, Abstract No. 666, 2 pages.

Healey, J.S. et al. (Aug. 2005). "Left Atrial Appendage Occlusion Study (LAAOS): Results of a Randomized Controlled Pilot Study of Left Atrial Appendage Occlusion During Coronary Bypass Surgery in Patients at Risk for Stroke," *American Heart Journal* 150(2):288-293.

Hein, R. et al. (2005). "Patent Foramen Ovale and Left Atrial Appendage: New Devices and Methods for Closure," *Pediatric Cardiology* 26(3):234-240.

Heist, E.K. et al. (Nov. 2006). "Analysis of the Left Atrial Appendage by Magnetic Resonance Angiography in Patients with Atrial Fibrillation," *Heart Rhythm* 3(11):1313-1318.

Ho, I. et al. (Apr. 24, 2007). "Percutaneous Epicardial Mapping Ablation of a Posteroseptal Accessory Pathway," *Circulation* 115:e418-e421.

Ho, S.Y. et al. (Nov. 1999). "Anatomy of the Left Atrium: Implications for Radiofrequency Ablation of Atrial Fibrillation," *Journal of Cardiovascular Electrophysiology* 10(11):1525-1533.

Hoit, B.D. et al. (Jan. 1993). "Altered Left Atrial Compliance After Atrial Appendectomy. Influence on Left Atrial and Ventricular Filling," *Circulation Research* 72(1):167-175.

Inoue, Y. et al. (Jul.-Aug. 1997). "Video Assisted Thoracoscopic and Cardioscopic Radiofrequency Maze Ablation," *Asaio Journal* 43(4):334-337, Abstract Only.

International Search Report mailed on Jun. 1, 2010, for PCT Application No. PCT/US2010/029668, filed on Apr. 1, 2010, 1 page.

Jaïs, P. et al. (2003). "Radiofrequency Ablation for Atrial Fibrillation," *European Society of Cardiology* 5(Supplement H):H34-H39.

(56) References Cited

OTHER PUBLICATIONS

Johnson, W.D. et al. (2000). "The Left Atrial Appendage: Our Most Lethal Human Attachment! Surgical Implications," *Euro. J. Cardiothoracic. Surg.* 17:718-722.

Jongbloed, M.R.M. et al. (2005). "Clinical Applications of Intracardiac Echocardiography in Interventional Procedures," *Heart* 91:981-990.

Kamohara, K. et al. (Aug. 2006). "Evaluation of a Novel Device for Left Atrial Appendage Exclusion: The Second-generation Atrial Exclusion Device," *The Journal of Thoracic and Cardiovascular Surgery* 132(2):340-346.

Kanderian, A.S. et al. (2008). "Success of Surgical Left Atrial Appendage Closure: Assessment by Transesophageal Echocardiography," *Journal of the American College of Cardiology* 52(11):924-929.

Kato, H. et al. (Aug. 1, 1996). "Evaluation of Left Atrial Appendage Stasis in Patients With Atrial Fibrillation Using Transesophageal Echocardiography With an Intravenous Albumin-Contrast Agent," *The American Journal of Cardiology* 78:365-369.

Katz, E.S. et al. (Aug. 2000). "Surgical Left Atrial Appendage Ligation is Frequently Incomplete: A Transesophageal Echocardiographic Study," *Journal of the American College of Cardiology* 36(2):468-471.

Kenner, H.M. et al. (Dec. 1966). "Intrapericardial, Intrapleural, and Intracardiac Pressures During Acute Heart Failure in Dogs Studied without Thoracotomy," *Circulation Research* 19:1071-1079.

Kerut, E.K. et al. (Jul. 2008). "Anatomy of the Left Atrial Appendage," *Echocardiography* 25(6):669-673.

Khargi, K. et al. (2005). "Surgical Treatment of Atrial Fibrillation: A Systematic Review," *European Journal of Cardiothoracic Surgery* 27:258-265.

Kim, K.B. et al. (Jan. 1998). "Effect of the Cox Maze Procedure on the Secretion of Atrial Natriuretic Peptide," *J. Thorac. Cardiovasc. Surg.* 115(1):139-146; discussion 146-147.

Kistler, P.M. et al. (May 2007). "The Left Atrial Appendage: Not Just an Innocent Bystander," *J. Cardiovasc Electrophysiol* 18(5):465-466.

Klein, H. et al. (Apr. 1990). "The Implantable Automatic Cardioverter-Defibrillator," *Herz* 15(2):111-125, Abstract Only.

Kolb, C. et al. (Feb. 2004). "Incidence of Antitachycardia Therapy Suspension Due to Magnet Reversion in Implantable Cardioverter Defibrillators," *Pace* 27:221-223.

Krikorian, J.G. et al. (Nov. 1978). "Pericardiocentesis," *Am. J. Med.* 65(5):808-814.

Krum, D. et al. (2004). "Visualization of Remnants of the left Atrial Appendage Following Epicardial Surgical Removal," *Heart Rhythm* 1:249.

Lacomis, J.M. et al. (Oct. 2003). "Multi-Detector Row CT of the Left Atrium and Pulmonary Veins before Radio-frequency Catheter Ablation for Atrial Fibrillation," *Radio Graphics* 23:S35-S48.

Lacomis, J.M. et al. (2007, e-pub. Oct. 17, 2007). "Dynamic Multidimensional Imaging of the Human Left Atrial Appendage," *Europace* 9:1134-1140.

Lee, R. et al. (1999). "The Closed Heart MAZE: A Nonbypass Surgical Technique," *The Annals of Thoracic Surgery* 67:1696-1702.

Levinson, M.L. et al. (1998). "Minimally Invasive Atrial Septal Defect Closure Using the Subxyphoid Approach," *Heart Surg. Forum* 1(1):49-53, Abstract Only.

Lewis, D.R. et al. (1999). "Vascular Surgical Intervention for Complications of Cardiovascular Radiology: 13 Years' Experience in a Single Centre," *Ann. R. Coll. Surg. Engl.* 81:23-26.

Li, H. (2007). "Magnet Decoration, Beautiful But Potentially Dangerous for Patients with Implantable Pacemakers or Defibrillators," *Heart Rhythm* 4(1):5-6.

Lindsay, B.D. (1996). "Obliteration of the Left Atrial Appendage: A Concept Worth Testing," *The Annals of Thoracic Surgery* 61:515.

Lip, G.Y.H. et al. (Jun. 2001). "Thromboprophylaxis for Atrial Flutter," *European Heart Journal* 22(12):984-987.

Lustgarten, D.L. et al. (May/Jun. 1999). "Cryothermal Ablation: Mechanism of Tissue Injury and Current Experience in the Treatment of Tachyarrhythmias," *Progress in Cardiovascular Diseases* 41(6):481-498.

Macris, M. et al. (Jan. 1999). "Minimally Invasive Access of the Normal Pericardium: Initial Clinical Experience with a Novel Device," *Clin. Cardiol.* 22(Suppl. I):I-36-I-39.

Maisch, B. et al. (Jan. 1999). "Intrapreicardial Treatment of Inflammatory and Neoplastic Pericarditis Guided by Pericardioscopy and Epicardial Biopsy—Results from a Pilot Study," *Clin. Cardiol.* 22(Supp. I):I-17-I-22.

Mannam, A.P. et al. (Apr. 1, 2002). "Safety of Subxyphoid Pericardial Access Using a Blunt-Tip Needle," *The American Journal of Cardiology* 89:891-893.

Mattox, K.L. et al. (May 1997). "Newer Diagnostic Measure and Emergency Management," *Ches Surg Clin N Am.* 7(2):213-226, Abstract Only.

McCarthy, P.M. et al. (2008). "Epicardial Atrial Fibrillation Ablation," Chapter 23 in *Contemporary Cardiology: Atrial Fibrillation, From Bench to Bedside*, Natale, A. et al. eds., Humana Press,: Totowa, NJ, pp. 323-332.

McCaughan, J.J. Jr., et al. (Nov. 1957). "Aortography Utilizing Percutaneous Left Ventricular Puncture," located at <http://www.archsurg.com>, last visited on Apr. 7, 2009, 73:746-751, Abstract Only.

McClelland, R.R. (1978). "Congenital Aneurysmal Dilatation of the Left Auricle Demonstrated by Sequential Cardiac Blood-Pool Scintiscanning," *J. Nucl. Med.* 19(5):507-509.

Melo, J. et al. (Apr. 21, 2008). "Surgery for Atrial Fibrillation in Patients with Mitral Valve Disease: Results at Five Years from the International Registry of Atrial Fibrillation Surgery," *The Journal of Thoracic and Cardiovascular Surgery* 135(4):863-869.

Miller, P.S.J. et al. (Feb. 2005). "Are Cost Benefits of Anticoagulation for Stroke Prevention in Atrial Fibrillation Underestimated?" *Stroke* 36:360-366.

Miyasaka, Y. et al. (Jul. 11, 2006). "Secular Trends in Incidence of Atrial Fibrillation in Olmsted County, Minnesota, 1980 to 2000, and Implications on the Projections for Future Prevalence," *Circulation* 114:119-125.

Morris, J.J. Jr. (1979). "Transvenous versus Transthoracic Cardiac Pacing," Chapter 16 in *Cardiac Pacins: A Concise Guide to Clinical Practice*, pp. 239-245.

Mráz, T. et al. (Apr. 2007). "Role of Echocardiography in Percutaneous Occlusion of the left Atrial Appendage," *Echocardiography* 24(4):401-404.

Naclerio, E.A. et al. (1979). "Surgical Techniques for Permanent Ventricular Pacing," Chapter 10 in *Cardiac Pacing: A Concise Guide to Clinical Practice*, pp. 145-168.

Nakai, T. et al. (May 7, 2002). "Percutaneous Left Atrial Appendage Occlusion (PLAATO) for Preventing Cardioembolism: First Experience in Canine Model," *Circulation* 105:2217-2222.

Nakajima, H. et al. (2004). "Consequence of Atrial Fibrillation and the Risk of Embolism After Percutaneous Mitral Commissurotomy: The Necessity of the Maze Procedure," *The Annals of Thoracic Surgery* 78:800-806.

Non-Final Office Action mailed on Mar. 13, 2008 for U.S. Appl. No. 10/963,371, filed on Oct. 11, 2004, 13 pages.

Non-Final Office Action mailed on Aug. 6, 2008 for U.S. Appl. No. 10/963,371, filed on Oct. 11, 2004, 14 pages.

Non-Final Office Action mailed on Jun. 26, 2009, for U.S. Appl. No. 11/600,671, filed on Nov. 15, 2006, 9 pages.

Non-Final Office Action mailed on Dec. 30, 2009, for U.S. Appl. No. 11/400,714, filed on Apr. 7, 2006, 8 pages.

Non-Final Office Action mailed on Jul. 22, 2010, for U.S. Appl. No. 12/037,802, filed on Feb. 26, 2008, 10 pages.

Non-Final Office Action mailed on Nov. 15, 2010, for U.S. Appl. No. 12/055,213, filed on Mar. 25, 2008, 18 pages.

Notice of Allowance mailed on Sep. 17, 2010, for U.S. Appl. No. 10/963,371, filed on Oct. 11, 2004, 7 pages.

Notice of Allowance mailed on Sep. 17, 2010, for U.S. Appl. No. 11/600,671, filed on Nov. 15, 2006, 7 pages.

(56) References Cited

OTHER PUBLICATIONS

Odell, J.A. et al. (1996). "Thorascopic Obliteration of the Left Atrial Appendage: Potential for Stroke Reduction?" *Ann. Thorac. Surg.* 61:565-569.

O'Donnell, M. et al. (2005). "Emerging Therapies for Stroke Prevention in Atrial Fibrillation," *European Heart Journal* 7(Supplement C):C19-C27.

Omran, H. et al. (1997). "Left Atrial Appendage Function in Patients with Atrial Flutter," *Heart* 78:250-254.

Onalan, O. et al. (2005). "Nonpharmacologic Stroke Prevention in Atrial Fibrillation," *Expert Rev. Cardiovasc. Ther.* 3(4):619-633.

Onalan, O. et al. (2007). "Left Atrial Appendage Exclusion for Stroke Prevention in Patients With Nonrheumatic Atrial Fibrillation," *Stroke* 38(part 2):624-630.

Ostermayer, S. et al. (2003). "Percutaneous Closure of the Left Atrial Appendage," *Journal of Interventional Cardiology* 16(6):553-556.

Ota, T. et al. (2006). "Epicardial Atrial Ablation Using a Novel Articulated Robotic Medical Probe Via a Percutaneous Subxiphoid Approach," *National Institute of Health* 1(6):335-340.

Ota, T. et al. (Oct. 2007). "Impact of Beating Heart left Atrial Ablation on Left-sided Heart Mechanics," *The Journal of Thoracic and Cardiovascular Surgery* 134:982-988.

Pennec, P-Y. et al. (2003). "Assessment of Different Procedures for Surgical Left Atrial Appendage Exclusion," *The Annals of Thoracic Surgery* 76:2167-2168.

Perk, G. et al. (Aug. 2009). "Use of Real Time Three-Dimensional Transesophageal Echocardiography in Intracardiac Catheter Based Interventions," *J. Am Soc Echocardiogr* 22(8):865-882.

Pollick C. (Feb. 2000). "Left Atrial Appendage Myopathy," *Chest* 117(2):297-308.

Poulsen, T.S. et al. (Feb. 15, 2005). "Is Aspirin Resistance or Female Gender Associated With a High Incidence of Myonecrosis After Nonurgent Percutaneous Coronary Intervention?" *J. Am. Coll. Cardiol.* 45(4):635-636.

Reznik, G. et al. (Oct. 1992). "Percutaneous Endoscopic Implantation of Automatic Implantable Cardioverter/Defibrillator (AICD): An Animal Study of a New Nonthoracotomy Technique," *J. Laparoendosc. Surg.* 2(5):255-261, Abstract Only.

Robicsek, F. (1987). "Closed-Chest Decannulation of Transthoracically Inserted Aortic Balloon Catheter without Grafting," *Journal of Cardiac Surgery* 2(2):327-329.

Ross, J. Jr. et al. (Jun. 3, 2008). "Transseptal Left Heart Catheterization: A 50-Year Odyssey," *Journal of the American College of Cardiology* 51(22):2107-2115.

Rubin, D.N. et al. (Oct. 1, 1996). "Evaluation of Left Atrial Appendage Anatomy and Function in Recent-Onset Atrial Fibrillation by Transesophageal Echocardiography," *Am J Cardiol* 78:774-778.

Ruchat, P. et al. (2002). "Off-pump Epicardial Compartmentalization for Ablation of Atrial Fibrillation," *Interactive Cardio Vascular and Thoracic Surgery* 1:55-57.

Salzberg, S.P. et al. (2008). "Surgical Left Atrial Appendage Occlusion: Evaluation of a Novel Device with Magnetic Resonance Imaging," *European Journal of Cardiothoracic Surgery* 34:766-770.

Sapp, J. et al. (Dec. 2001). "Electrophysiology and Anatomic Characterization of an Epicardial Accessory Pathway," *Journal of Cardiovascular Electrophysiology* 12(12):1411-1414.

Scharf, C. et al. (2005). "Catheter Ablation for Atrial Fibrillation: Pathophysiology, Techniques, Results and Current Indications," *Continuous Medical Education* 8:53-61.

Scherr, D. et al. (Apr. 2009). "Incidence and Predictors of left Atrial Thrombus Prior to Catheter Ablation of Atrial Fibrillation," *Journal of Cardiovascular Electrophysiology* 20(4):379-384.

Schmidt, H. et al. (Sep. 2001). "Prevalence of Left Atrial Chamber and Appendage Thrombi in Patients With Atrial Flutter and Its Clinical Significance," *Journal of the American College of Cardiology* 38(3):778-784.

Schneider, B. et al. (2005, e-pub. Aug. 22, 2005). "Surgical Closure of the Left Atrial Appendage—A Beneficial Procedure?" *Cardiology* 104:127-132.

Schweikert, R.A. et al. (Sep. 16, 2003). "Percutaneous Pericardial Instrumentation for Endo-Epicardial Mapping of Previously Failed Ablation," *Circulation* 108:1329-1335.

Schweikert, R.A. et al. (2005). "Epicardial Access: Present and Future Applications for Interventional Electrophysiologists," Chapter 25 in *New Arrhythmia Technolgies*, Wang, P.J. ed., Blackwell Publishing, pp. 242-256.

Seferovic, P. et al. (Jan. 1999). "Initial Clinical Experience with the PerDUCER® Device: Promising New Tool in the Diagnosis and Treatment of Pericardial Disease," *Clin. Cardiol.* 22(Supp I):I-30-I-35.

Sengupta, P.P. et al. (2005). "Transoesophageal Echocardiography," *Heart* 91:541-547.

Sharada, K. et al. (2005). "Non-Surgical Transpericardial Catheter Ablation of Post-Infarction Ventricular Tachycardia," *Indian Heart J* 57:58-61.

Sievert, H. et al. (Apr. 23, 2002). "Percutaneous Left Atrial Appendage Transcatheter Occlusion to Prevent Stroke in High-Risk Patients With Atrial Fibrillation," *Circulation* 105:1887-1889.

Singer, D.E. et al. (Sep. 2004). "Antithrombotic Therapy in Atrial Fibrillation: The Seventh ACCP Conference on Antithrombotic and Thrombolytic Therapy," *Chest* 126(3):429S-456S.

Smith, P.W. et al. (Nov. 1956). "Diagnosis of Mitral Regurgitation by Cardioangiography," *Circulation* 14:847-853.

Soejima, K. et al. (2004). "Subxiphoid Surgical Approach for Epicardial Catheter-Based Mapping and Ablation in Patients With Prior Cardiac Surgery or Difficult Pericardial Access," *Circulation* 110:1197-1201.

Sosa, E. et al. (1996). "A New Technique to Perform Epicardial Mapping in the EP Laboratory," *J. Cardiovasc. Electrophysiol.* 7(6):531-536.

Sosa, E. et al. (Mar. 1998). "Endocardial and Epicardial Ablation Guided by Nonsurgical Transthoracic Epicardial Mapping to Treat Recurrent Ventricular Tachycardia," *J. Cardiovasc. Elecytophysiol.* 9(3):229-239.

Sosa, E. et al. (Dec. 14, 1999). "Different Ways of Approaching the Normal Pericardial Space," *Circulation* 100(24):e115-e116.

Sosa, E. et al. (Jul. 15, 2002). "Gaining Access to the Pericardial Space," *The American Journal of Cardiology* 90:203-204.

Sosa, E. et al. (Apr. 2005). "Epicardial Mapping and Ablation Techniques to Control Centricular Tachycardia," *Journal of Cardiovasc. Electrphsiol.* 16(4):449-452.

Sparks, P.B. et al. (2001). "Is Atrial Flutter a Risk Factor for Stroke?" *Journal of the American College of Cardiology* 38(3):785-788.

Spodick, D.H. (Nov. 1970). "Medical History of the Pericardium," *The American Journal of Cardiology* 26:447-454.

Stewart, J.M. et al. (Apr. 1992). "Bilateral Atrial Appendectomy Abolishes Increased Plasma Atrial Natriuretic Peptide Release and Blunts Sodium and Water Excretion During Volume Loading in Conscious Dogs," *Circulation Research* 70(4):724-732.

Stewart, S. (1974). "Placement of the Sutureless Epicardial Pacemaker Lead by the Subxiphoid Approach," *Ann. of Thoracic Surg.* 18(3):308-313.

Stoddard, M.F. et al. (1995). "Left Atrial Appendage Thrombus is not Uncommon in Patients with Acute Atrial Fibrillation and a Recent Embolic Event: A Transesophageal Echocardiographic Study," *J. Am. Coll. Cardiol.* 25:452-459, Abstract Only.

Stokes, K. (Jun. 1990). "Implantable Pacing Lead Technology," *IEEE Engineering in Medicine and Biology* pp. 43-49.

Stöllberger, C. et al. (2000). "Is the Left Atrial Appendage Our Most Lethal Attachment?" *European Journal of Cardio-Thoracic Surgery* 18:625-626.

Stöllberger, C. et al. (Dec. 2003). "Elimination of the Left Atrial Appendage to Prevent Stroke or Embolism?: Anatomic, Physiologic, and Pathophysiologic Considerations," 124(6):2356-2362.

Stöllberger, C. et al. (2006). "Stroke Prevention by Means of Epicardial Occlusion of the Left Atrial Appendage," *Journal of Thoracic and Cardiovascular Surgery* 132(1):207-208.

Stöllberger, C. et al. (2007). "Arguments Against Left Atrial Appendage Occlusion for Stroke Prevention," *Stroke* 38:e77.

Stöllberger, C. et al. (2007). "Leave the Left Atrial Appendage Untouched for Stroke Prevention!" *Journal of Thoracic and Cardiovascular Surgery* 134(2):549-550.

(56) References Cited

OTHER PUBLICATIONS

Su, P. et al. (Sep. 2008, e-pub. May 8, 2007). "Occluding the Left Atrial Appendage: Anatomical Considerations," *Heart* 94(9):1166-1170.
Subramanian, V.A. (Jun. 1997). "Less Invasive Arterial CABG on a Beating Heart," *Ann. Thorac. Surg.* 63(6 Suppl.):S68-S71.
Subramanian, V.A. et al. (Dec. 1997). "Minimally Invasive Direct Coronary Artery Bypass Grafting: two-Year Clinical Experience," *Ann. Thorac. Surg.* 64(6):1648-1653, Abstract Only.
Suehiro, S. et al. (1996). "Echocardiography-Guided Pericardiocentesis With a Needle Attached to a Probe," *Ann. Thoracic Surg.* 61:741-742.
Sun, F. et al. (Feb. 2006). "Subxiphoid Access to Normal Pericardium with Micropuncture Set: Technical Feasibility Study in Pigs," *Radiology* 238(2):719-724.
Szili-Torok, T. et al. (2001). "Transseptal Left heart Catheterisation Guided by Intracardiac Echocardiography," *Heart* 86:e11-e15.
Tabata, T. et al. (Feb. 1, 1998). "Role of Left Atrial Appendage in left Atrial Reservoir Function as Evaluated by Left Atrial Appendage Clamping During Cardiac Surgery," *The American Journal of Cardiology* 81:327-332.
Tomar, M. et al. (Jul.-Aug. 2006). "Transcatheter Closure of Fossa Ovalis Atrial Septal Defect: A Single Institutional Experience," *Indian Heart Journal* 58(4):325-329.
Troughton, R.W. et al. (Feb. 28, 2004). "Pericarditis," *The Lancet* 363:717-727.
Ulicny K.S. et al. (Jun. 1992). "Conjoined Subrectus Pocket for Permanent Pacemaker Placement in the Neonate," *Ann Thorac Surg.* 53(6):1130-1131, Abstract Only.
Valderrabano, M. et al. (Sep. 2004). "Percutaneous Epicardial Mapping During Ablation of Difficult Accessory Pathways as an Alternative to Cardiac Surgery," *Heart Rhythm* 1(3):311-316.
Von Korn, H. et al. (2006). "Simultaneous Combined Interventional Percutaneous Left Atrial Auricle and Atrial Septal Defect Closure," *Heart* 92:1462.
Wang, T.J. et al. (Aug. 27, 2003). "A Risk Score for Predicting Stroke or Death in Individuals With New-Onset Atrial Fibrillation in the Community," *American Medical Association* 290(8):1049-1056.
Watkins, L. et al. (Nov. 1982). "Implantation of the Automatic Defibrillator: The Subxiphoid Approach," *Ann. of Thoracic Surg.* 34(5):515-520.
W.L. Gore & Associates (Aug. 11, 2006). "Gore Helex™ Septal Occluder," located at <http://www.fda.gov/cdrh/pdf5/p050006a.pdf>, last visited on Jun. 14, 2007, 3 pages.
Wolber, T. et al. (Jan. 2007). "Potential Interference of Small Neodymium Magnets with Cardiac pacemakers and Implantable Cardioverter-defibrillators," *Heart Rhythm* 4(1):1-4.
Wolf, P.A. et al. (Oct. 1978). "Epidemiologic Assessment of Chronic Atrial Fibrillation and Risk of Stroke: The Fiamingham Study," *Neurology* 28:973-977.
Wolf, P.A. et al. (Aug. 1991). "Atrial Fibrillation as an Independent Risk Factor for Stroke: The Framingham Study," *Stroke* 22(8):983-988.
Wolf, P.A. et al. (Feb. 9, 1998). "Impact of Atrial Fibrillation on Mortality, Stroke, and Medical Costs," *Arch Intern Med* 158:229-234.
Wong, J.W.W. et al. (2006). "Impact of Maze and Concomitant Mitral Valve Surgery on Clinical Outcomes," *The Annals of Thoracic Surgery* 82:1938-1947.
Wongcharoen, W. et al. (Sep. 2006). "Morphologic Characteristics of the Left Atrial Appendage, Roof, and Septum: Implications for the Ablation of Atrial Fibrillation," *Journal of Cardiovascular Electrophysiology* 17(9):951-956.
Wood, M.A. (Jan. 2006). "Precutaneous Pericardial Instrumentation in the Electrophysiology Laboratory: A Case of Need," *Heart Rhythm* 3(1):11-12.
Written Opinion of the International Searching Authority mailed on Jun. 1, 2010, for PCT Application No. PCT/US2010/029668, filed on Apr. 1, 2010, 8 pages.
Wudel, J.H. et al. (Apr. 3, 2008). "Video-Assisted Epicardial Ablation and left Atrial Appendage Exclusion for Atrial Fibrillation: Extended Follow-Up," *The Annals of Thoracic Surgery* 85:34-38.
Wyse, D.G. et al. (Dec. 5, 2002). "Of 'Left Atrial Appendage Amputation, Ligation, or Occlusion in Patients with Atrial Fibrillation'," *N Engl J Med* 347(23):1825-1833, Abstract Only.
Yamada, Y. et al. (Aug. 2006). "Video-Assisted Thoracoscopy to Treat Atrial Tachycardia Arising from Left Atrial Appendage," *Journal of Cardiovascular Electrophysiology* 17(8):895-898.
Zapolanski, A. et al. (May 2008). "Safe and Complete Exclusion of the left Atrial Appendage, A Simple Epicardial Approach," *Innovations* 3(3):161-163.
Zenati, M.A. et al. (Sep. 2003). "Left Heart Pacing Lead Implantation Using Subxiphoid Videopericardioscopy," *Journal of Cariodvascular Electrophysiology* 14(9):949-953.
Zenati, M.A. et al. (2004). "Mechanical Function of the Left Atrial Appendage Following Epicardial Bipolar Radiofrequency Ablation," *Cardiothoracic Techniques and Technologies X*, Abstract 121A, p. 176.
Zenati, M.A. et al. (2005). "Modification of the Left Atrial Appendage," Chapter 12 in *Innovative Management of Atrial Fibrillation*, Schwartzman, David ed., Blackwell Science Ltd., 5 pages.
Chinese Office Action mailed on Dec. 4, 2013 for Chinese Patent Application No. 201080023899.9, filed on Apr. 1, 2010, 4 pages.
Final Office Action mailed on Apr. 26, 2011, for U.S. Appl. No. 12/037,802, filed Feb. 26, 2008, 9 pages.
Final Office Action mailed on Sep. 20, 2011, for U.S. Appl. No. 12/212,511, filed Sep. 17, 2008, 8 pages.
Final Office Action mailed on Oct. 28, 2011, for U.S. Appl. No. 12/055,213, filed Mar. 25, 2008, 15 pages.
Final Office Action mailed on May 4, 2012, for U.S. Appl. No. 12/363,359, filed Jan. 30, 2009, 10 pages.
Final Office Action mailed on May 16, 2012, for U.S. Appl. No. 12/363,381, filed Jan. 30, 2009, 8 pages.
Final Office Action mailed on Jul. 11, 2012, for U.S. Appl. No. 13/033,532, filed Feb. 23, 2011, 8 pages.
Final Office Action mailed on Jul. 24, 2012, for U.S. Appl. No. 12/212,511, filed Sep. 17, 2008, 6 pages.
Final Office Action mailed on Oct. 18, 2012, for U.S. Appl. No. 12/124,023, filed May 20, 2008, 15 pages.
Final Office Action mailed on Nov. 8, 2013, for U.S. Appl. No. 12/037,802, filed Feb. 26, 2008, 15 pages.
Japanese Office Action mailed on Dec. 17, 2013, for Japanese Patent Application No. 2012-503714, filed on Apr. 1, 2010, 4 pages.
Non-Final Office Action mailed on Feb. 17, 2011, for U.S. Appl. No. 12/212,511, filed Sep. 17, 2008, 14 pages.
Non-Final Office Action mailed on Apr. 28, 2011, for U.S. Appl. No. 12/055,213, filed Mar. 25, 2008, 20 pages.
Non-Final Office Action mailed on Oct. 27, 2011, for U.S. Appl. No. 12/363,359, filed Jan. 30, 2009, 11 pages.
Non-Final Office Action mailed on Nov. 9, 2011, for U.S. Appl. No. 12/363,381, filed Jan. 30, 2009, 10 pages.
Non-Final Office Action mailed on Dec. 22, 2011, for U.S. Appl. No. 13/033,532, filed Feb. 23, 2011, 8 pages.
Non-Final Office Action mailed on Mar. 7, 2012, for U.S. Appl. No. 12/124,023, filed May 20, 2008, 13 pages.
Non-Final Office Action mailed on Apr. 2, 2012, for U.S. Appl. No. 12/212,511, filed Sep. 17, 2008, 5 pages.
Non-Final Office Action mailed on Sep. 18, 2013, 2011, for U.S. Appl. No. 12/055,213, filed Mar. 25, 2008, 15 pages.
Non-Final Office Action mailed on May 31, 2013, for U.S. Appl. No. 12/124,023, filed May 20, 2008, 14 pages.
Notice of Allowance mailed on Nov. 24, 2010, for U.S. Appl. No. 11/400,714, filed Apr. 7, 2006, 8 pages.
Notice of Allowance mailed on Feb. 22, 2013, for U.S. Appl. No. 12/212,511, filed Sep. 17, 2008, 8 pages.
Notice of Allowance mailed on Mar. 18, 2013, for U.S. Appl. No. 12/212,511, filed Sep. 17, 2008, 6 pages.
Notice of Allowance mailed on Mar. 4, 2014, for U.S. Appl. No. 12/055,213, filed Mar. 25, 2008, 9 pages.
Australian Office Action mailed on Mar. 28, 2014 for Australian Patent Application No. 2010232589, filed on Apr. 1, 2010, four pages.

(56) References Cited

OTHER PUBLICATIONS

Chinese Office Action mailed on Jun. 25, 2014, for Chinese Patent Application No. 201080023899.9, filed on Apr. 1, 2010, 5 pages.
Final Office Action mailed on Nov. 14, 2014, for U.S. Appl. No. 12/363,359, filed Jan. 30, 2009, 10 pages.
Final Office Action mailed on Aug. 12, 2014, for U.S. Appl. No. 13/033,532, filed Feb. 23, 2011, 6 pages.
Non-Final Office Action mailed on Apr. 2, 2014, for U.S. Appl. No. 13/033,532, filed Feb. 23, 2011, 8 pages.
Non-Final Office Action mailed on Jun. 17, 2014, for U.S. Appl. No. 12/363,359, filed Jan. 30, 2009, 7 pages.
Notice of Allowance mailed on Apr. 1, 2014, for U.S. Appl. No. 12/363,381, filed Jan. 30, 2009, 9 pages.
Notice of Allowance mailed on Dec. 29, 2014, for U.S. Appl. No. 12/363,381, filed Jan. 30, 2009, 9 pages.
Notice of Allowance mailed on Apr. 3, 2014, for U.S. Appl. No. 12/037,802, filed Feb. 26, 2008, 8 pages.
Notice of Allowance mailed on Nov. 18, 2014, for Australian Patent Application No. 2010232589, filed on Apr. 1, 2010, 3 pages.
Japanese Office Action mailed on Aug. 4, 2015, for Japanese Patent Application No. 2014-179551, filed on Apr. 1, 2010, 2 pages.
Non-Final Office Action mailed on Sep. 10, 2015, for U.S. Appl. No. 12/363,359, filed Jan. 30, 2009, 12 pages.

* cited by examiner

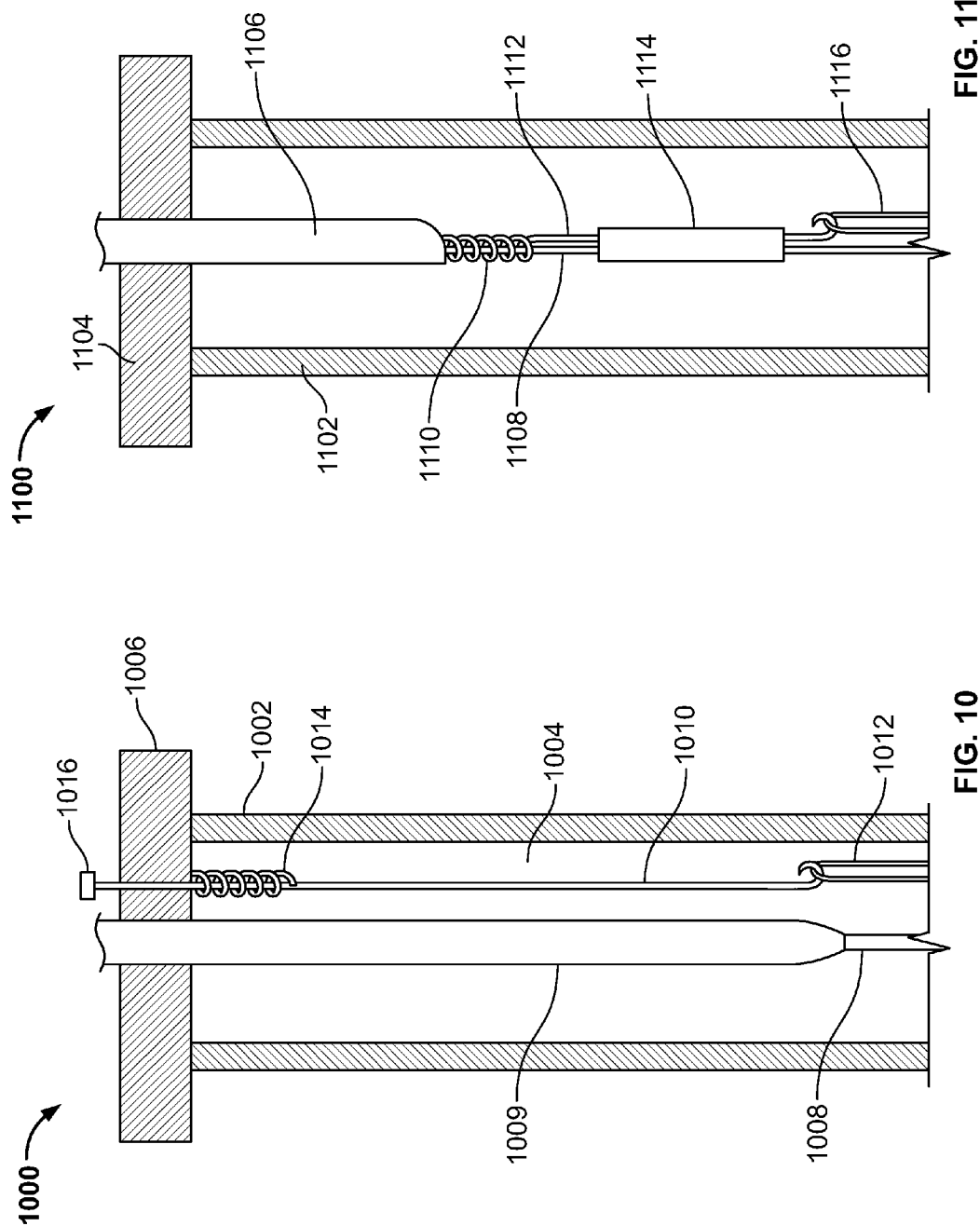

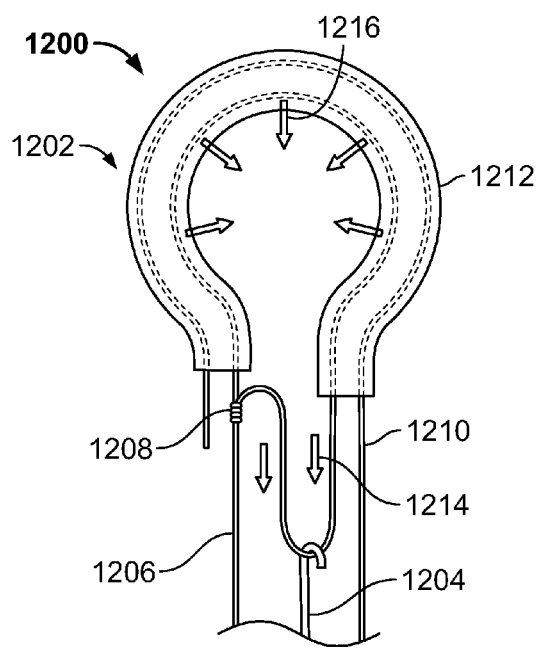
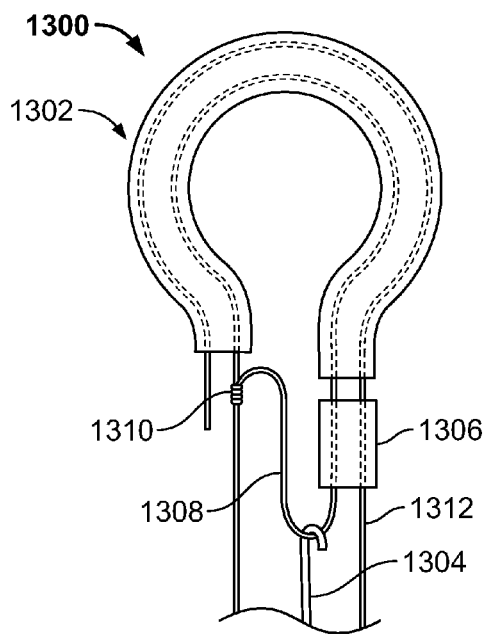
FIG. 12
FIG. 13A
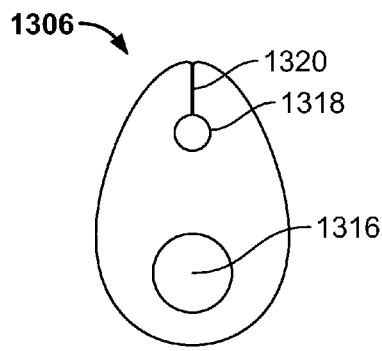
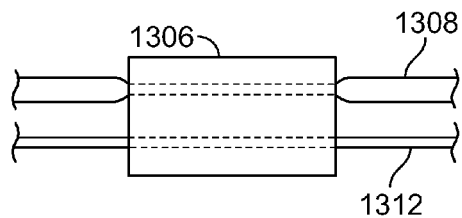
FIG. 13B
FIG. 13C

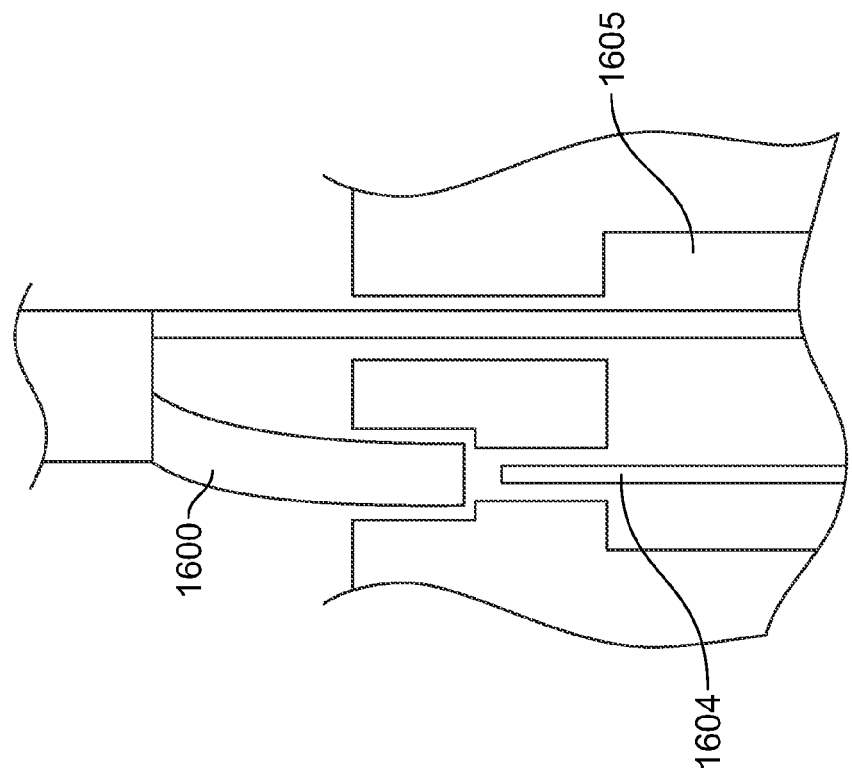
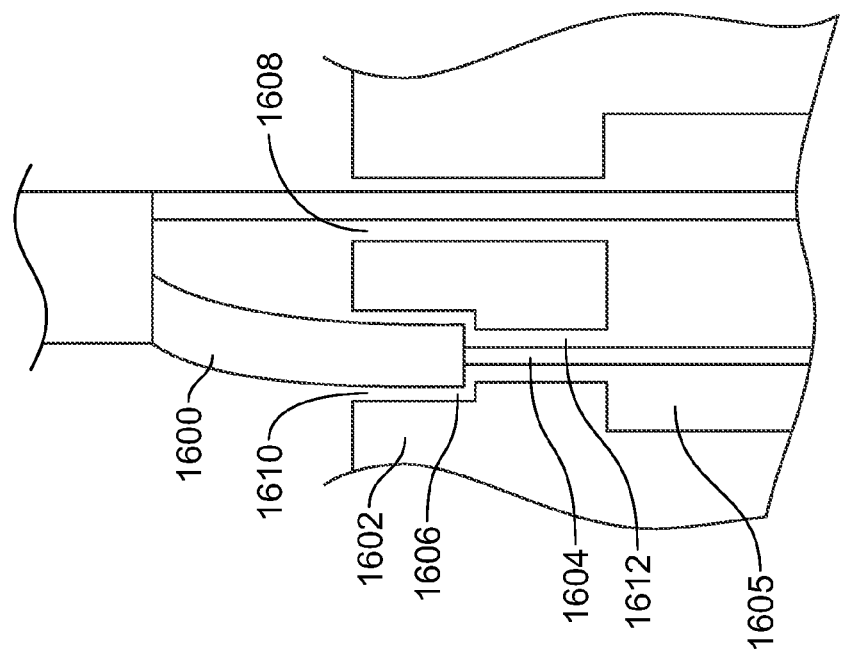

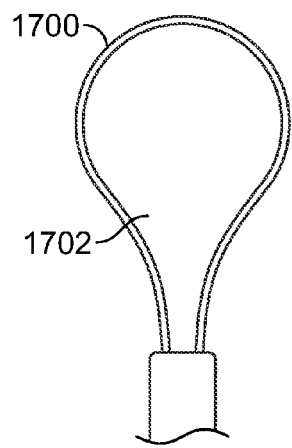
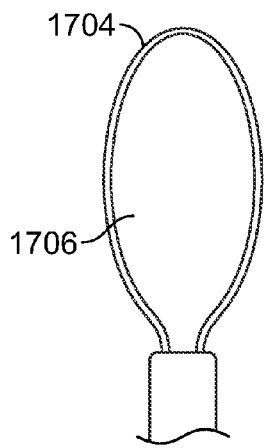
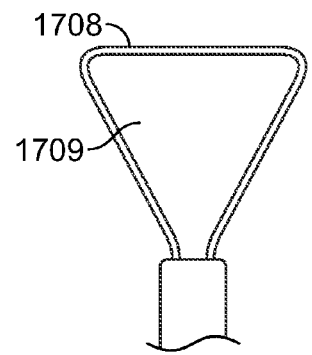
FIG. 17A          FIG. 17B          FIG. 17C
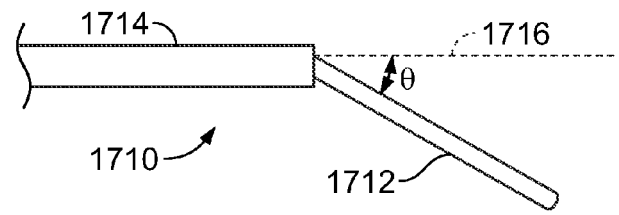
FIG. 17D

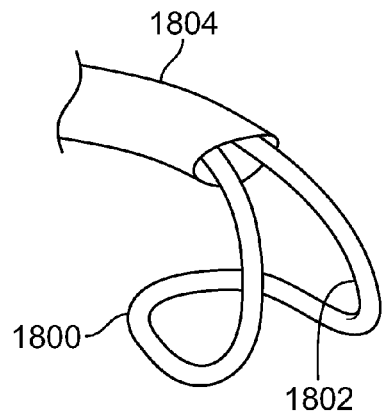
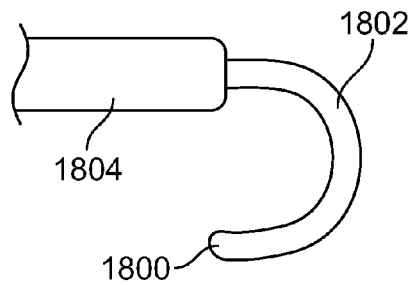
FIG. 18A  FIG. 18B
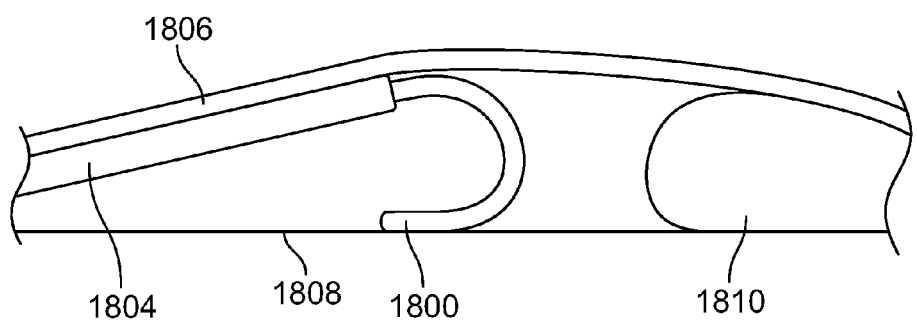
FIG. 18C
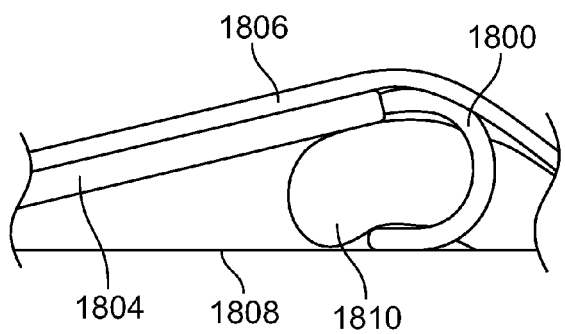
FIG. 18D

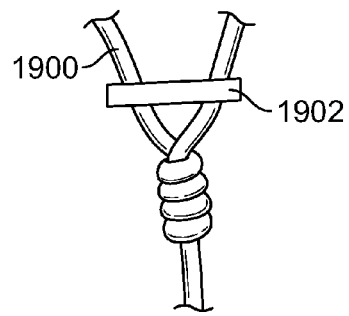
FIG. 19A
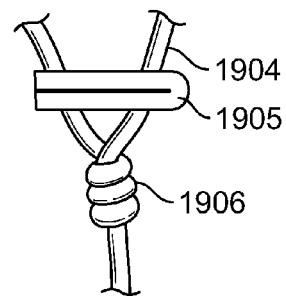
FIG. 19B
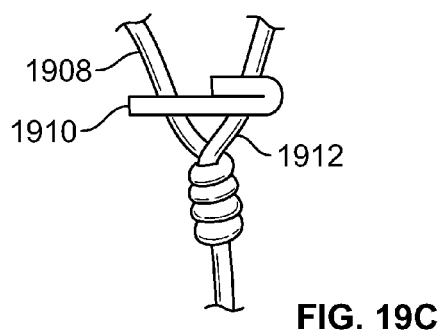
FIG. 19C
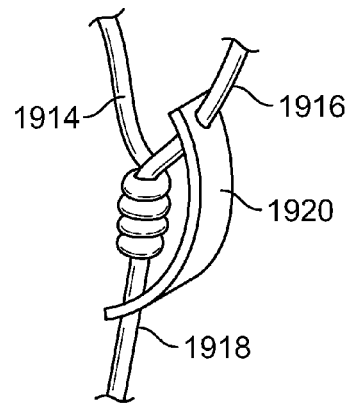
FIG. 19D
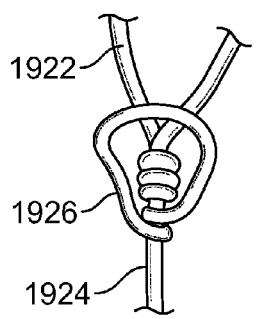
FIG. 19E
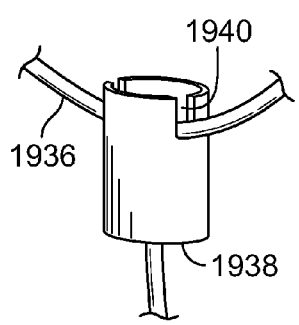
FIG. 19F
FIG. 19G

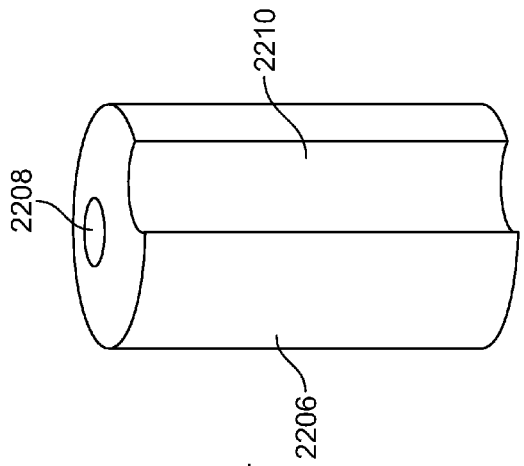
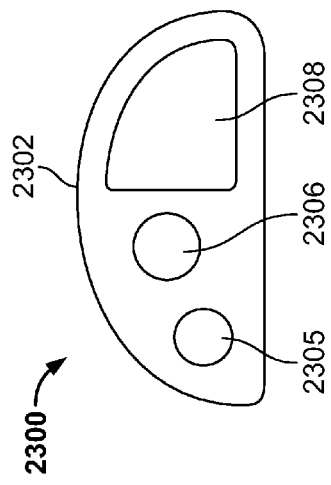
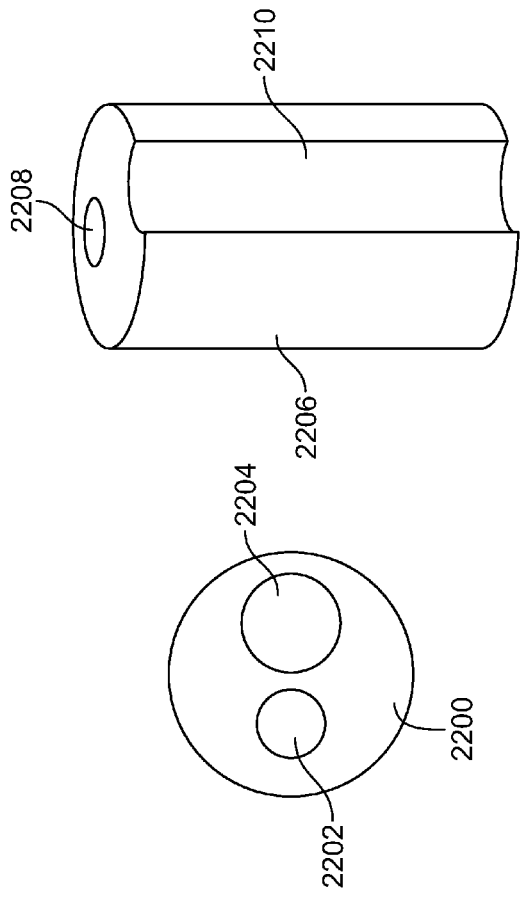
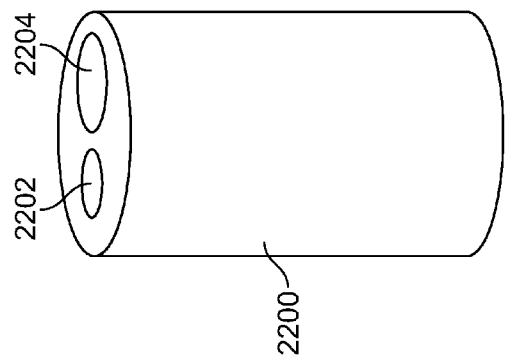
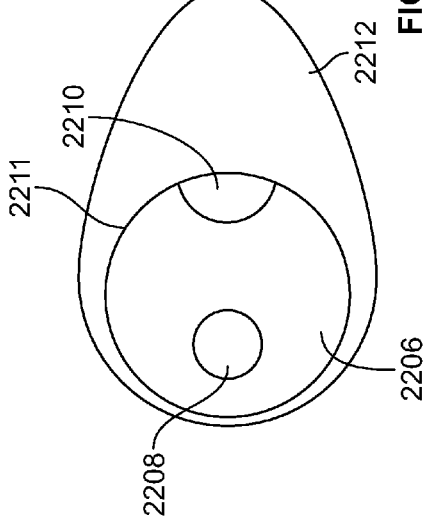

TISSUE LIGATION DEVICES AND CONTROLS THEREFOR

CROSS-REFERENCE TO RELATED APPLICATIONS

This application claims priority to U.S. Provisional Patent Application Ser. No. 61/165,828, filed on Apr. 1, 2009, which is incorporated by reference herein in its entirety.

FIELD

This invention relates generally to devices and methods for ligating tissue, such as the left atrial appendage, using surgically, minimally invasive or intravascular approaches, and to handles for actuating such devices.

BACKGROUND

Atrial fibrillation is a common problem that afflicts millions of patients. Atrial fibrillation often results in the formation of a thrombus, or clot, in the appendage of the left atrium. This presents a problem, inasmuch as the thrombus can dislodge and embolize to distant organs, which may result in adverse events such as a stroke. For this reason, most patients with atrial fibrillation are treated with one or more blood thinners to help prevent the formation of a thrombus. Blood thinners, however, can present health risks of their own, especially in the elderly. These risks, such as bleeding, often require a user to make significant lifestyle changes.

Several methods have been developed to address the potential problem of thrombus formation in the left atrial appendage. One such method includes suturing the left atrial appendage along the base or ostial neck where it joins the atrial chamber. In this way, blood flow into the atrial appendage is cut off, eliminating the risk of thrombus formation therein. This is typically done through open-heart surgery, which limits the availability of the procedure to those who are at a particularly high risk, or who are otherwise undergoing an open-heart procedure. In addition, open-heart surgery requires general anesthesia and has a number of well-known risks, making it less desirable.

Other methods have also been investigated. These methods include methods of stapling the base of the appendage and methods of filling the appendage with a space occupying or occluding member. Stapling is not preferred given the fragility of the appendage and its tendency to rupture, while occlusion devices may not effectively prevent all blood flow into the appendage.

Additional devices and methods for closing the left atrial appendage or other suitable tissues would therefore be desirable. In particular, devices and methods for closing the left atrial appendage using minimally invasive, intravascular, or a combination of these techniques, would be desirable in order to avoid the need for opening the chest. Of course, additional devices for use in open surgical procedures are desirable as well, especially when those devices offer additional advantages over standard devices.

BRIEF SUMMARY

Described here are devices for closing one or more tissues, and mechanisms for controlling these devices. Generally, the devices described here comprise a snare loop assembly, wherein the snare loop assembly comprises a snare and a suture loop, an elongate body, and a mechanism for controlling the snare loop assembly which may be mounted on a handle. In some variations the snare loop assembly may comprise a retention member that may releasably couple the suture loop and the snare. In other variations the devices comprise one or more force-reducing suture locks to help prevent the suture loop from inadvertently disengaging from the snare loop assembly.

Generally, the elongate body may be attached to the handle and may comprise one or more lumens. In some variations, the elongate body comprises one lumen. In another variation, the elongate body comprises two lumens. In still another variation, the elongate body comprises three or more lumens. In some variations, the elongate body may comprise one or more pieces of separation tubing, which may alter the size or shape of one or more lumens, or may divide one or more lumens into two or more sub-lumens. Additionally, in some variations the elongate body may comprise a tip portion. In some variations, the tip portion may be formed separately from the elongate body and may be attached thereto. In other variations, the tip portion may be formed integrally with the elongate body. The tip portion may have any suitable number of lumens or sub-lumens passing therethrough. In some variations, the tip portion may at least partially house one or more pieces of separation tubing. In some variations, the tip portion comprises a knot-receiving recess for at least temporarily housing a suture knot of a suture loop. In some of these variations, the tip portion may comprise one or more elements that may eject a suture knot from a knot-receiving recess. In some of these variations, a balloon or other expandable structure may be expanded in knot-receiving recess to a eject suture knot therefrom. In other variations, a pusher may be used to eject a suture knot from the knot-receiving recess.

In some variations, the devices may comprise one or more suture management elements to hold a portion of the suture loop within the elongate body. In still other variations, the devices comprise one or more suture hooks. In some variations, the one or more suture hooks comprise one or more springs attached thereto. In some of these variations, the one or more springs may be disposed concentrically around a snare of the snare loop assembly. In other variations, separation tubing may be used to hold excess suture within the elongate body. In some of these variations, the closure device may further comprise a suture tube for releasably holding a length of suture. The suture tube may be configured such that suture held within suture tube may tear or otherwise break through a portion of the suture tube when the suture loop is tightened. In some variations, one end of the suture tube may be attached to separation tubing and the other end of the suture tube may be attached to one or more components of the snare loop assembly (e.g., a snare, a retention member, a suture lock, or the like). In some variations, the suture tube may comprise one or more grooves or cuts on a side thereof. In other variations, the suture tube may comprise one or more strengthening members disposed therein.

In other variations, the closure device may comprise a pulley suture. In some of these variations, the pulley suture may be looped around or doubled over a portion of a suture loop. In other variations, the pulley suture may be temporarily attached to a portion of a suture loop via one or more deformable elements. In some variations, one end of the pulley suture may be temporarily or permanently attached to a snare via a suture lock. Another end of the pulley suture may be attached to one or more components of the device handle. In some of these variations, an end of the pulley suture may be attached to a suture fob. In some of these variations, an end of a suture loop may be attached to the same suture fob.

The handles described here may have any suitable configuration of elements or combination of elements. In some variations, the handle comprises one or more device introducers. In some of these variations, the device introducer may be a guidewire introducer. In other variations, the handle may comprise a strain relief portion, which may help prevent the handle from disengaging with the rest of the closure device. In still other variations, the handle may comprise one or more elements configured to tighten a suture loop. Tightening a suture loop may remove excess suture from the suture loop, release a suture loop from a snare loop assembly, or ligate a target tissue. For example, in some variations, this element is a snare control. In other variations, this element is a suture knob. In some variations, the devices may be actuated and controlled without an actual handle. In some of these variations, one or more devices or systems may be used to control the device, such as a surgical master-slave system utilizing a user-operated computer.

Also described here are methods for closing one or more tissues. In some variations, the methods comprise introducing a closure device into a body, where the closure device comprises a snare loop assembly having an opened configuration and a closed configuration and comprising a snare and a suture loop, where the suture loop has slack when the snare loop assembly is in its closed configuration. The snare loop assembly may be advanced in its closed configuration to a target tissue, opened to its open configuration, advanced over the target tissue, and closed around the target tissue. The slack from the suture loop may then be removed, and the suture tightened to disengage the suture loop from the snare loop assembly and ligate the target tissue. It should be appreciated that the closure device of these methods may be any suitable closure device as described hereinthroughout. In some variations, the method may comprise placing an expandable structure in the left atrial appendage to help position the snare loop assembly. In other variations, the method may comprise placing an expandable structure in or near an entrance to the left atrial appendage to help position the snare loop assembly. In some variations, one or more expandable structures may be released inside of and maintained in the left atrial appendage. In other variations, one or more embolic or haemostatic materials may be delivered to the left atrial appendage to help form a bolus or occlusive structure therein.

BRIEF DESCRIPTION OF THE DRAWINGS

FIGS. 10 and 11 are cross-sectional side views of portions of two variations of the closure devices described here.

FIGS. 12 and 13A-13C illustrate two variations of snare loop assemblies suitable for use with the closure devices described here.

FIGS. 16A-16B illustrate a variation of the closure devices described here in which a snare is releasably connected to an elongate body.

FIGS. 17A-17D illustrate different illustrative variations of snare configurations.

FIGS. 18A and 18B depict a perspective view and a side view, respectively, of a variation of a snare. FIGS. 18C and 18D depict a method by which the snare of FIGS. 18A and 18B may be used to ensnare tissue.

FIGS. 19A-19G illustrate several variations of knot shielding mechanisms suitable for use with the closure devices described here.

FIGS. 22A and 22B depict a perspective view and a top view, respectively, of one variation of separation tubing suitable for use with the devices described here. FIGS. 22C and 22D depict a perspective view and a top view, respectively, of another variation of separation tubing suitable for use with the devices described here.

FIG. 23A depicts a front view of one illustrative variation of a tip portion suitable for use with the devices described here.

DETAILED DESCRIPTION

Figure 1:
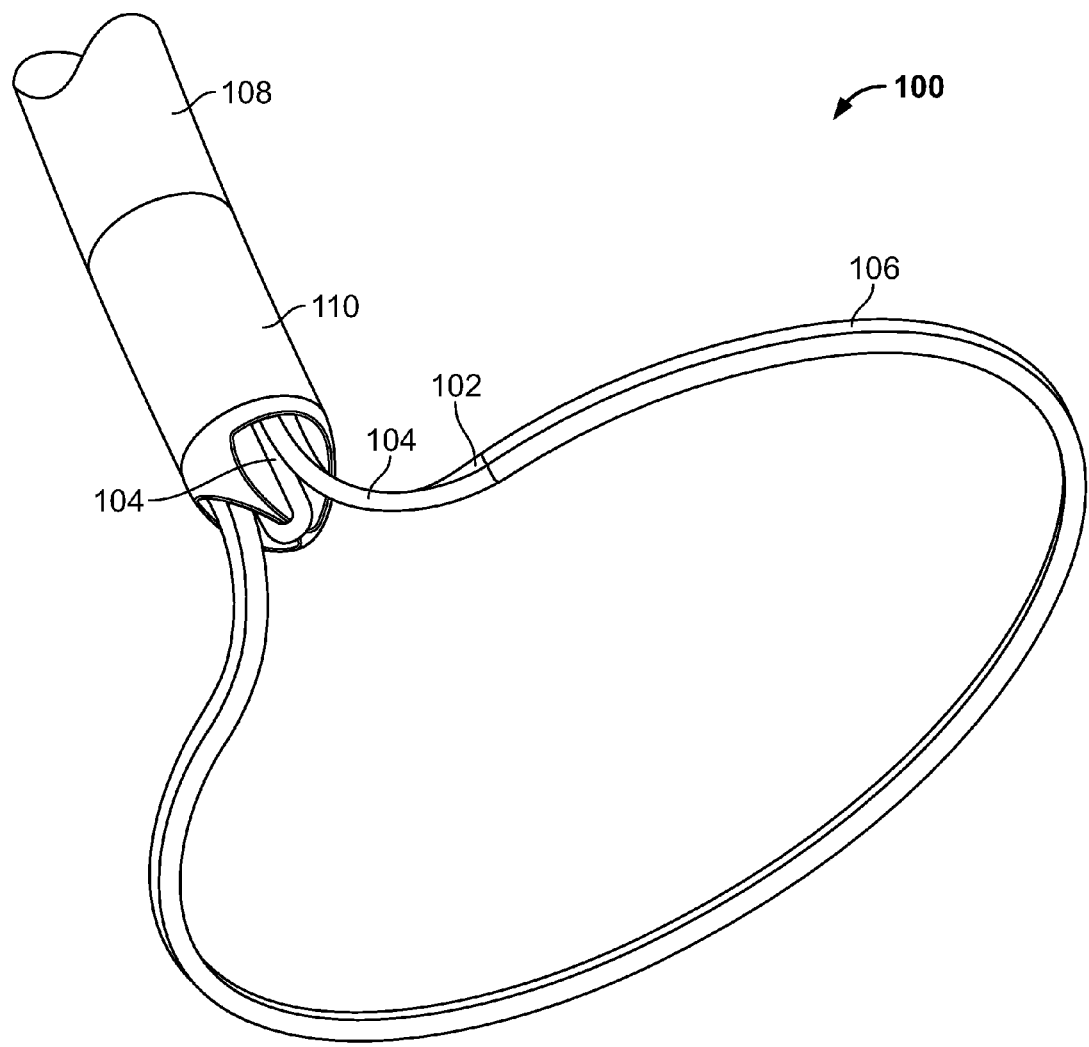
FIG. 1 is a view of a distal end of an illustrative device having a snare loop assembly.

Described here are closure devices, handles for actuating closure devices, and methods for closing tissues using one or more closure devices. Generally, the closure devices comprise a snare loop assembly comprising a snare and a suture loop, such as those described in U.S. patent application Ser. No. 12/055,213, entitled "Devices, Systems, and Methods for Closing the Left Atrial Appendage" and filed on Mar. 5, 2008, which is incorporated by reference herein in its entirety. The devices described here may be suitable for use with minimally invasive access to the left atrial appendage (e.g., through a small incision above, beneath or through the rib cage, through an incision in the costal cartilage or the xiphoid, through a port, through the vasculature, etc.).

Generally, the closure devices described here comprise an elongate body, and a snare loop assembly. In some variations the closure devices may further comprise a handle. A handle or other control mechanism (e.g., a surgical master-slave robotic system) may be used to control and actuate the snare loop assembly through the elongate body, as will be explained in more detail below. The snare loop assembly, in turn, may be used to temporarily or permanently close, tighten, ligate or other restrict tissue. To achieve this, the snare loop assembly may be changed between a delivery, or "closed," configuration and a deployed, or "open," configuration, and vice versa, as will be described in more detail below. Placing the snare loop assembly in a closed configuration may allow for low-profile advancement of the snare loop assembly to a target location, or may allow the snare loop assembly to close around a target tissue. Conversely, placing a snare loop assembly in an open configuration may allow the snare loop assembly to be placed around one or more target tissues, or may allow the snare loop assembly to release one or more target tissues previously closed by the snare loop assembly.

In use, a distal end of an elongate body may be advanced into the body toward a target tissue (e.g., the left atrial appendage). This advancement may be done in a minimally invasive manner. During advancement, the snare loop assembly may be in a closed configuration to help prevent the snare loop assembly from snagging or catching on tissue or other obstructions. Once the distal end of the elongate body has reached a location at or near the target tissue, the snare loop assembly may be opened to a deployed configuration. The snare loop assembly may then be advanced, moved, or otherwise manipulated to encircle at least a portion of the target tissue. The snare loop assembly may then be closed around the encircled tissue to close, ligate, or otherwise restrict the target tissue. The snare loop assembly may be re-opened, repositioned, and re-closed as necessary. In some instances, a suture loop (not shown) or other restricting device may be tightened and released from the closure device to maintain the target tissue in a closed fashion. To remove the closure device from the body, the snare loop assembly may again be opened to release the target tissue (it should be appreciated that the suture loop or other closure device may remain in place) such that the snare loop assembly and elongate body may be withdrawn. Once the target tissue is released, the snare loop assembly may be closed to facilitate low-profile withdrawal.

The closure devices may contain one or more additional features, as will be described in more detail below. In some variations, the snare loop assembly comprises one or more force-reducing suture locks. These elements, as will be described in more detail below, may act to releasably or permanently connect various components of the snare loop assembly while reducing forces that are transmitted to one or more portions of the snare loop assembly. In other variations, the closure device may comprise one or more features that helps maintain at least a portion of the suture loop inside of the elongate body when the device is in an opened and/or closed configuration. In some of these variations, the closure device may comprise a suture hook that engages a portion of the snare loop assembly. In other variations, the elongate body may comprise one or more pieces of separation tubing. This separation tubing may further comprise a suture tube attached thereto for releasably holding at least a portion of the suture loop. In still other variations, the elongate body may comprise a pulley suture that engages one or more portions of the snare loop assembly. Each of these features will be described in more detail below, and it should be appreciated that the closure devices described here may comprise any combination of these features.

Figure 14:
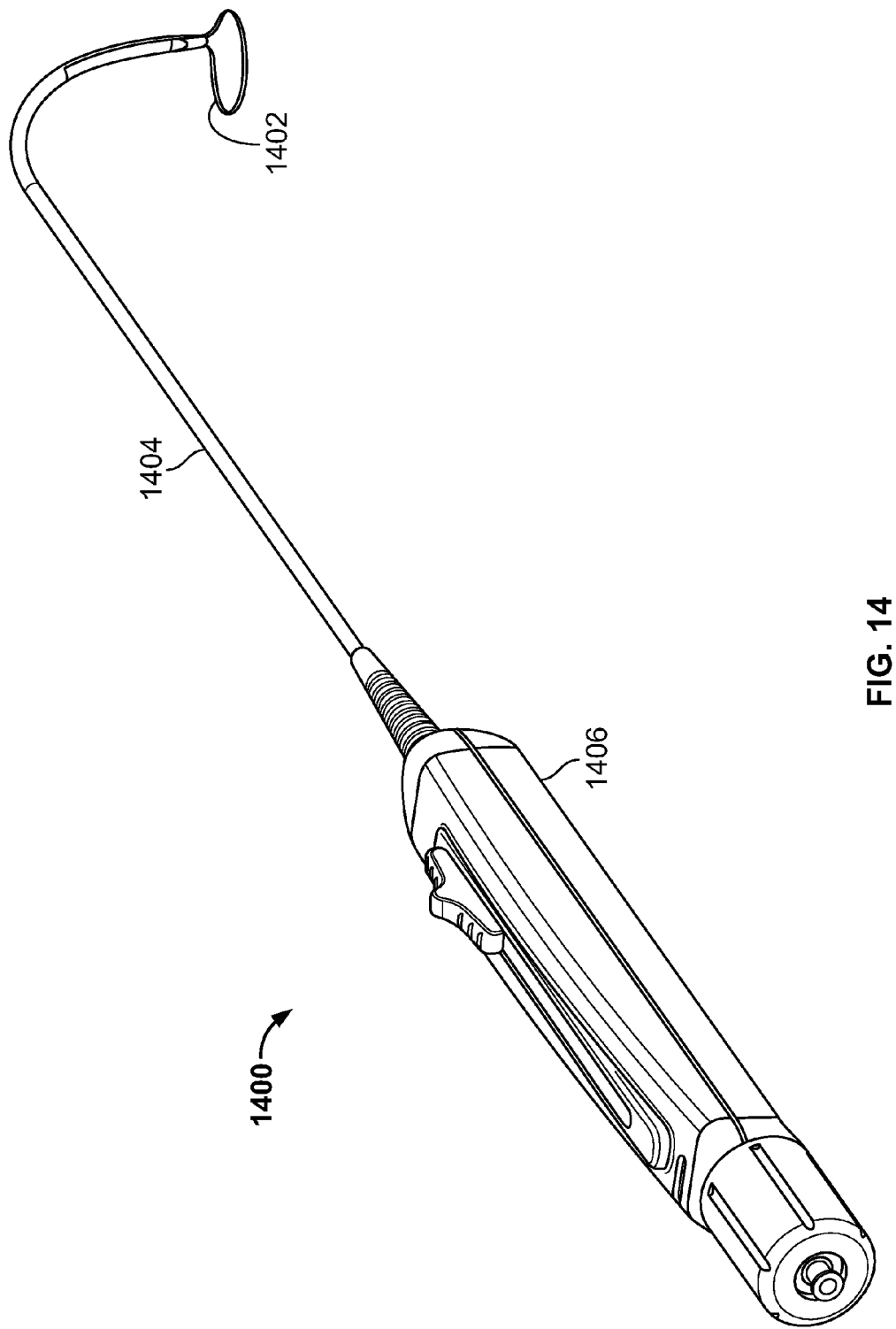
FIG. 14 shows a perspective view of an illustrative variation of the closure devices described here.

FIG. 14 depicts one illustrative variation of closure device (1400). Shown there is snare loop assembly (1402), elongate body (1404), and handle (1406). As noted above, handle (1406) may be used to control and actuate the snare loop assembly (1402) through the elongate body (1404) in order to move snare loop assembly (1402) between a closed configuration (as shown in FIG. 14) and a deployed configuration (not shown), and vice versa.

Snare Loop Assembly

As mentioned above, the snare loop assemblies of the closure devices described here may be used to temporarily close or restrict one or more target tissues. Generally the snare loop assembly comprises a snare, a suture loop, and a retention member at least temporarily connecting the snare and the suture loop. The snare loop assembly may also comprise one or more force-reducing suture locks, as will be described in more detail below. FIG. 1 shows an illustrative variation of snare loop assembly (100) comprising snare (102), suture loop (104), and retention member (106). Snare loop assembly (100) may be at least partially disposed in elongate body (108) having tip (110). Snare loop assembly (100) is shown in FIG. 1 in an open configuration, and the portion of snare loop assembly (100) extending out of elongate body (104) may define a continuous aperture therethrough. This aperture may be defined by one or more components of the snare loop assembly (100) (e.g., the snare), and may be suitable for encircling tissue such as the left atrial appendage. Generally, the snare (102) may be used to open and close the snare loop assembly (100), as will be described in more detail below. In some instances, retention member (106) may be configured to releasably couple suture loop (104) and snare (102), and may be configured to release suture loop (104) from snare loop assembly (100) upon application of sufficient force to suture loop (104).

Snare

In variations of snare loop assemblies comprising a snare, the snare may be at least partially moveable to change a snare loop assembly between open and closed configurations. Generally, a portion of the snare may be housed in the elongate body, and another portion of the snare may extend outside of the distal end of the elongate body to at least partially define the aperture of the snare loop assembly. In some variations, one end of the snare is fixed relative to one or more portions of the closure device, while the other end may be advanced or retracted through the elongate body. Movement of the free end of snare may change the amount of the snare loop assembly that is disposed outside of elongate body, and thus change the size of the aperture defined thereby. Specifically, advancement of the snare through the elongate body may increase the size of the snare loop assembly aperture, while retraction of the snare may decrease the size of the snare loop assembly aperture to close the snare loop assembly. The free end of the snare may be manipulated in any suitable manner. In some variations, the snare may be attached directly to one or more portions of the handle, as will be described in more detail below. In other variations, a hypotube, rod, or other rigid structure may be attached to the free end of the snare. This structure may in turn be moved by the handle, which may help facilitate advancement or withdrawal of the snare through the elongate body.

In variations where one end of the snare is fixed relative to the closure device, the snare may be fixed to any suitable portion of the device. For example, in some variations one end of the snare may be fixedly held in, on, or near a tip of the elongate body. In other variations, the fixed end of the snare may be affixed in one or more lumens of the elongate body. In still other variations, the fixed end of snare may be at least temporarily attached to the device's handle. Although one end of the snare may be temporarily fixed relative to the closure device, it should be appreciated that this fixed end may be configured to be releasable and/or moveable. Configuring the fixed end of the snare to be releasable and/or movable may serve a number of useful functions. In some instances, temporary or permanent device failure may result in the moveable portion of the snare becoming stuck or caught. In these instances, it may be necessary to release the fixed end in order to allow the closure device to release ensnared tissue. In other instances, it may be desirable to move the free end in order to provide for adjustment of the snare using both ends.

When one end of the snare is configured to be temporarily fixed relative to the elongate body, the end of snare may be released from its fixed relation in any suitable manner. For example, in some variations, an end of the snare may be temporarily held in a fixed manner by a frangible member. FIGS. 16A and 16B illustrate one variation by which an end of a snare (1600) may be releasably fixed to an elongate body (1602) by a frangible member (1604). Specifically, FIGS. 16A and 16B show a portion of elongate body (1602) having at least one lumen (1605). In this variation, a portion of lumen (1605) may be subdivided into at least first and second sub-lumens ((1606) and (1608) respectively). As shown in FIG. 16A, first sub-lumen (1606) has a first section (1610) with a first cross-sectional area, and a second section (1612) with a second cross-sectional area. The end of snare (1600) may be placed in first section (1610) of first sub-lumen (1606), and may be attached to the distal end of frangible member (1604), as shown in FIG. 16A. Frangible member (1604) may pass through second section (1612) of first sub-lumen (1606) and through lumen (1605).

The attachment of snare (1600) to frangible member (1604) may help temporarily lock the end of snare (1600) in place. The proximal end (not shown) of frangible member (1604) may be temporarily attached in a fixed manner to one or more portions of the device handle (not shown). Because the proximal end of the frangible member (1604) is held in place, the frangible member (1604) may prevent the snare from being pulled distally out of the end of the elongate body (1602). Additionally, the cross-sectional area of first section (1610) may be different from the cross-sectional area of the second section (1612) such that the end of snare (1600) is unable to pass from first section (1610) into second section (1612). In this way, the snare (1600) is prevented from moving proximally into the elongate body (1602). Additionally, in some variations, at least a portion of snare (1600) and first section (1610) may have non-circular cross sections (e.g., oval, triangle, square, polygon, or shape with irregular geometry) such that the snare (1614) housed within first section (1610) may unable to rotate relative to first section (1610). Because the end of snare (1600) is prevented from moving proximally, distally, or rotating relative to first section (1610) of first sub-lumen (1606), the end of snare may be effectively immobilized relative to the elongate body (1602).

Frangible member (1604) may be configured such that application of a sufficient force to frangible member (1604) is sufficient to break the attachment between frangible member (1604) and snare (1600). To release snare (1600) from its fixed position, a user may pull on the proximal end of frangible member (1604) directly or indirectly (e.g., via one or more handle components). Because the snare (1600) is prevented from moving proximally into second section (1612), sufficient proximal force applied to the frangible member (1604) may act to break the engagement between frangible member (1604) and snare (1600), thereby releasing the snare (1600) as shown in FIG. 16B.

The snares described here may be made of any suitable material or combination of materials. For example, in some variations the snare may be made from a shape-memory material, such as a shape-memory alloy (e.g., a nickel titanium alloy, etc.), or may be made from stainless steel, polyester, nylon, polyethylene, polypropylene, combinations thereof, and the like. In variations where the snare is made from the shape-memory material, the snare may be configured to take on a particular shape or configuration when the snare loop assembly is placed in an open configuration, but may still be at least partially withdrawn into the elongate body to place the snare loop assembly in a closed configuration. For example, as shown in FIG. 1 above, snare (102) may form a generally circular loop when snare loop assembly (100) is placed in an open configuration. While shown in FIG. 1 as being generally circular, snare (102) may form a loop of any given shape. FIGS. 17A-17D illustrate several additional snare configurations. In the variation shown in FIG. 17A, snare (1700) may form a teardrop-shaped loop (1702) when in a deployed configuration. In the variation shown in FIG. 17B, snare (1704) may form an oval or ellipsoid loop (1706) when in a deployed configuration. In the variation shown in FIG. 17C, snare (1708) may take on a substantially triangular loop (1709) when in a deployed configuration. Furthermore, in some variation, the snare loop may be angled relative to the elongate body. For example, FIG. 17D shows a side view of closure device (1710), in which snare (1712) exits elongate body (1714) that is at an angle ($\theta$) relative to the elongate body's longitudinal axis (1716). This angle ($\theta$) may be any suitable angle. For example, angle ($\theta$) may be about 5°, about 15°, about 30°, about 45°, about 60°, about 75°, about 90°, between about 40° and about 50°, between about 35° and about 55°, between about 30° and about 60°, or the like. Angling snare (1712) relative to elongate body (1714) may aid the snare (1712) in capturing tissue, as angling may better position the snare (1712) relative to tissue as the closure device is moved in the body.

FIGS. 18A-18D illustrate yet another variation of snare (1800). In this variation, snare (1800) may form a hook-shaped loop (1802) when snare (1800) extends from elongate body (1804) in an open configuration. FIG. 18A shows a perspective view of snare (1800), while 18B shows a side view of snare (1800). Because the loop (1802) bends back over itself to form a hook shape (as highlighted in a side view in FIG. 18B), the snare (1800) may help create space between body tissues when in an open configuration. For example, when opened in the pericardial space, as shown in FIG. 18C, the snare (1800) may lift the pericardial sac (1806) away from the heart (1808). Creating additional space within the pericardial sac may make it easier for snare (1800) to capture tissue, such as the left atrial appendage (1810), as shown in FIG. 18D.

Suture Loop

The snare loop assemblies described here may also comprise a suture loop for maintaining tissue in a closed manner. Generally, the suture loop may be releasably attached to the snare, for example, via a retention member, as will be described in more detail below. Furthermore, the suture loop may comprise a suture knot, but need not. This suture knot may be any suitable knot, including, but not limited to, a slip knot (e.g., a one-way slip knot). In some variations, as will be described in more detail below, at least a portion of the knot may be held within the tip of elongate body. In other variations, the suture knot may be temporarily held in fixed relation to the elongate body, as will be described in more detail below.

In variations where the suture loop comprises a slip knot, suture may be advanced or withdrawn through the slip knot to change the size of suture loop. In some instances where the suture knot is held within or against a tip of elongate body, the suture knot may not move while the size of suture loop is changed. This may help prevent the closure device from damaging tissue, as will be described in more detail below.

In some variations, the suture loop further comprises a unidirectional locking structure. In these variations, the unidirectional locking structure may be any structure capable of being advanced along the suture in one direction, but resisting movement in a second direction. In these variations, the locking structure may be advanced over a portion of the suture loop to help lock a suture knot in place. For example, in some variations the unidirectional locking structure may comprise a bead which is placed at least partially around the suture. In these variations, the bead may comprise one or more teeth or projections that allow for the bead to be advanced along the suture in one direction, but prevents or resists movement in the opposite direction. The locking structure may be advanced via one of the closure devices described here, or may be advanced by a separate device after the suture loop has been released from the closure device.

Suture loop may be made from any suitable material useful in exclusion or closure. For example, it may be made of a biodegradable material (e.g., polylactic acid, polyglycolic acid, polylactic-co-glycolic acid, etc.), or may be made of a non-biodegradable material (e.g., metal, steel, polyester, nylon, propylene, silk, combinations thereof and the like).

When the suture loop is tightened to close tissue, it may be possible for tissue to be pulled into the suture knot of the suture loop. If too much tissue is pulled into suture knot, the suture knot may clog or jam in a way that prevents the suture loop from being further tightened. In some variations the suture loop may comprise one or more pledgets or tube sections to help shield a portion of the suture knot. FIGS. 19A-19G illustrate several variations of suture loops comprising knot-shielding elements. In FIG. 19A, two legs of suture loop (1900) are threaded through a pledget (1902). Pledget may be made from any suitable material, such as, for example, polyurethane foam, felt, Teflon fabric, Dacron, collagen, or the like. FIG. 19B shows another variation of suture loop (1904) in which pledget (1905) is doubled over and two legs of suture loop (1904) are threaded therethrough. By increasing the thickness of pledget (1905) disposed between suture knot (1906) and tissue (not shown), the pledget (1905) may further reduce the amount of tissue that is pulled into suture knot (1906). FIG. 19C shows yet another variation of suture loop (1908) comprising pledget (1910), in which only a portion of pledget (1910) is doubled over. In this variation, one leg (1912) of suture loop (1908) may be threaded through the doubled-back portion of pledget (1910) while the other leg is threaded through the single-layered portion of pledget (1910).

FIG. 19D shows still another variation of suture loop (1914), in which one leg (1916) of suture loop (1914) and free end (1918) of suture loop (1914) are threaded through pledget (1920). FIG. 19E shows a variation of suture loop (1922) in which both legs and a free end (1924) of suture loop (1922) are all threaded through a pledget (1926). It should be appreciated that in some of these variations, one or more portions of pledget (1926) may be sized or otherwise configured to fit in one or more portions, lumens or recesses of the elongate body. FIG. 19F shows a variation of suture loop (1928) in which suture knot (1930) is at least partially shielded by tubing (1932). In this variation, the legs of suture loop (1928) may pass through the ends of tubing (1932), while suture knot (1930) may exit out of an aperture (1934) in the side of the tubing (1932). FIG. 19G shows another variation of suture loop (1936) in which the suture knot (not shown) is shielded by tubing (1938). In this variation, legs of suture loop (1936) may exit out of slots (1940) in the sides of tubing (1938), while the free end of suture loop (1936) may exit out of one end of the tubing (1938).

Retention Member

Figure 20A:
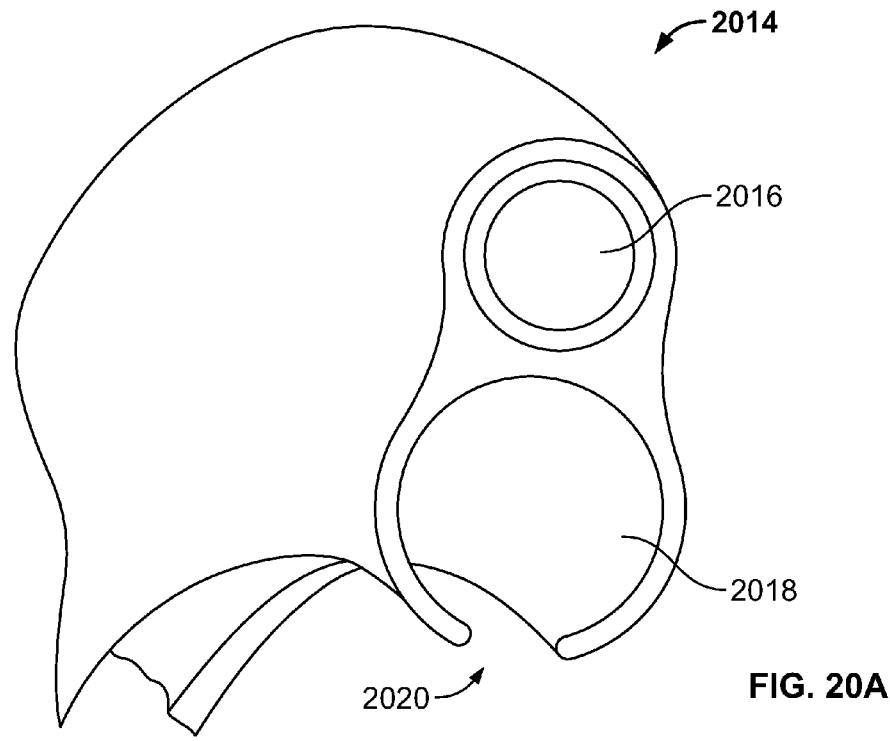
FIGS. 20A-20C depict illustrative retention members that may be used with the devices described here.
Figure 20B:
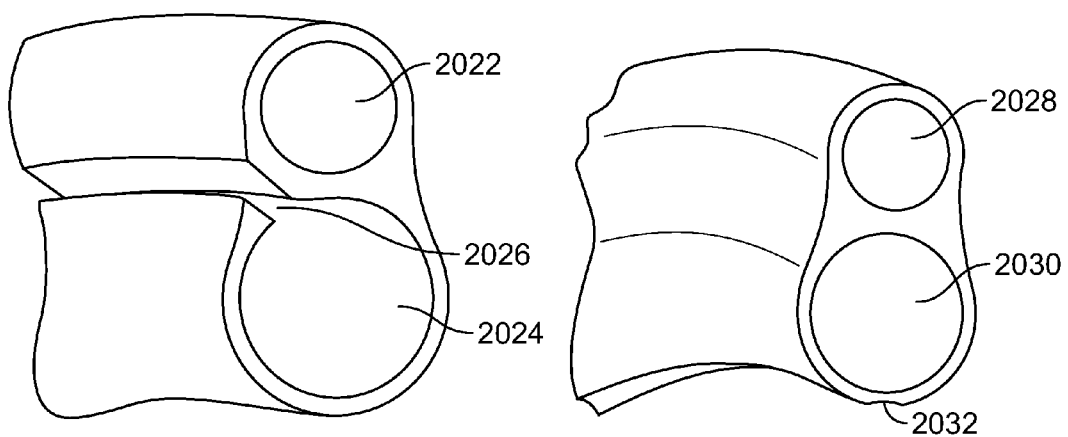
Figure 20C:
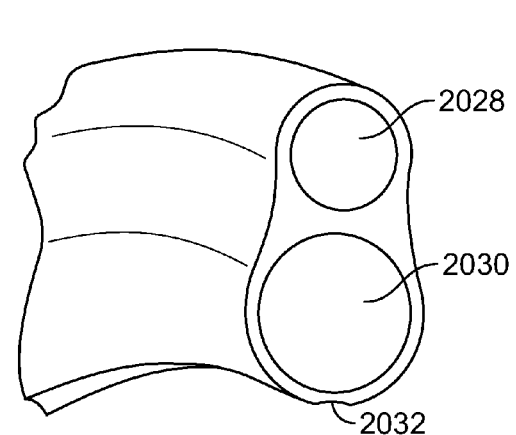

FIGS. 20A-20C depict illustrative retention members that may be used with the devices described herein. FIG. 20A shows an end view of a retention member (2014) having first and second lumens (2016, 2018) for retaining a closure element and a suture loop therein. In this variation, the second lumen (2018) has a slit or other opening (2020) along its length, for allowing the suture to pass therethrough when it is ready to be deployed. Of course, it should be understood that the first and second lumens may be positioned or oriented in any suitable way with respect to each other, and similarly, the slit or other opening on the second lumen may be positioned or oriented in any suitable fashion with respect to the first lumen (e.g., it may be approximately 180°, approximately 150°, approximately 120°, approximately 90°, approximately 60°, approximately 30°, or the like, from the first lumen (2016)). FIG. 20B provides an illustration of a retention member having a first lumen (2022), a second lumen (2024), and a slit (2026). In this variation, the slit (2026) is positioned closer to the first lumen (2022) than the slit of FIG. 20A. The width or spacing of the slit opening may be selected as desired or appropriate. Similarly, the slit need not extend or be continuous along the entire length of the retention member. In some variations, the slits may have prongs or arms along its length to help capture and retain the suture therein. In other variations, the slits may be covered at spaced apart locations therealong with a biodegradable polymer, temporarily used to tack or hold down the suture. Of course, in still other variations, the retention member does not comprise a slit, and instead comprises some other type of retention mechanism, such as the prongs or tacks described just above. In yet other variations, there are no slits or openings in the retention member and the suture loop is released upon removing or withdrawing the retention member and closing the device.

FIG. 20C provides another variation of a retention member. In this variation, the retention member has a first lumen (2028), second lumen (2030), and a separation region (2032). The separation region may be constructed in any suitable fashion. For example, the separation region may comprise a perforated region adapted to perforate and release the suture with the application of force. Alternatively, the separation region may be a thin-walled or other type of weakened region that may be configured to break and release the suture. It should be understood that the retention member may have any suitable geometry or shape, and may be made from any suitable material. Similarly, the lumens need not be full circles or have a circular cross-sectional geometry. When these or other types of retention members are used, the suture loop may be torn out, pulled through, or otherwise released from the retention member after it has been properly positioned and tightened as desirable.

Elongate Body

As mentioned briefly above, the elongate body of the closure devices described here may connect the distal end of the snare loop assembly and the handle or actuating mechanism while still allowing for control of the snare loop assembly through the elongate body. Specifically, at least a portion of some of the snare loop assembly components may be housed within elongate body, and may be connected to the handle through the elongate body. In some variations, at least a portion of the elongate body may be flexible, which may help facilitate navigation of the elongate body in and through tissue.

Figure 21:
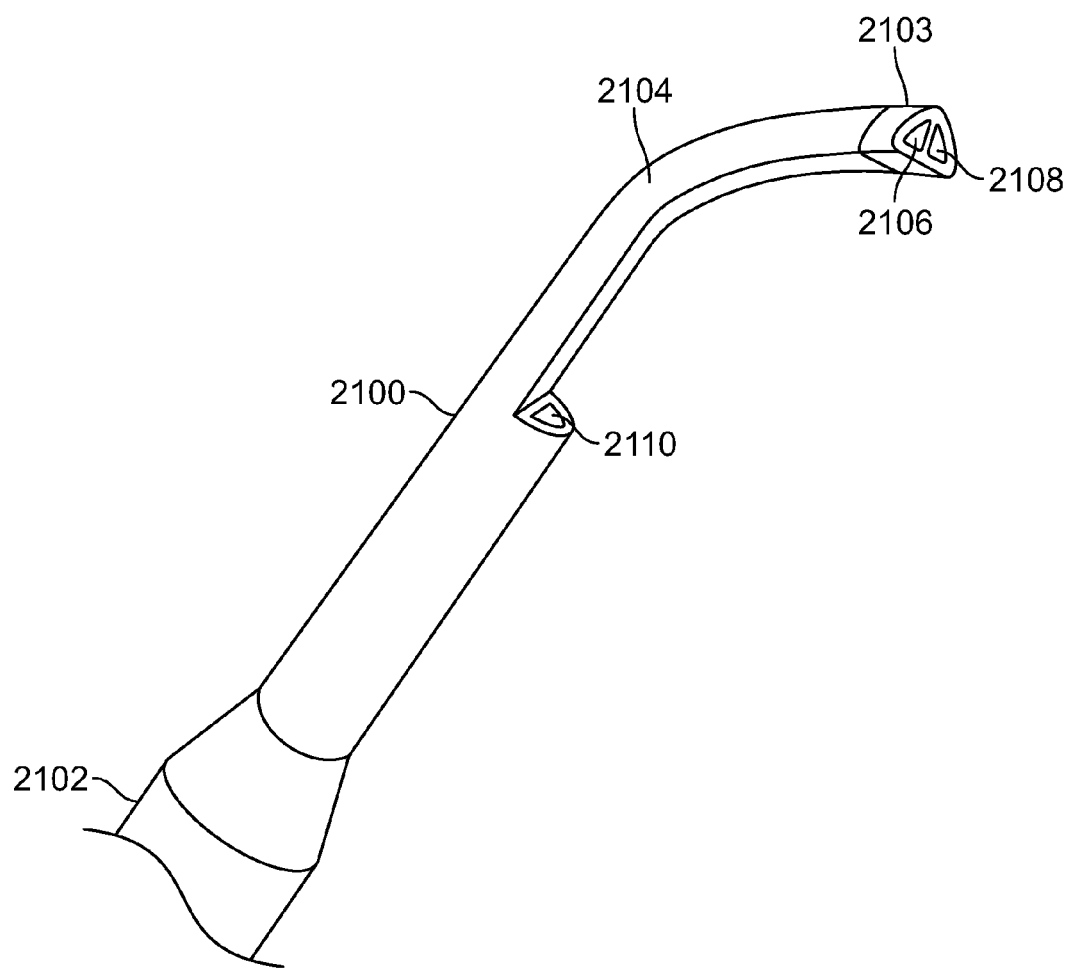
FIG. 21 depicts an illustrative variation of an elongate body suitable for use with the devices described here.

FIG. 21 shows one illustrative variation of an elongate body suitable for use with the closure devices described here. Shown there is elongate body (2100) attached to handle portion (2102). Elongate body (2100) may comprise tip portion (2103), curve (2104), first lumen (2106), second lumen (2108), and third lumen (2110). While shown in FIG. 21 as having a single curve (2104), elongate body (2100) may have no curves or may have multiple curves in different portions of the elongate body (2100). Furthermore, in some variations the closure device may comprise one or more mechanisms that may act or function to change the shape of the elongate body (2100). In instances where the elongate body (2100) comprises one or more curves (2104), a tube, mandrel or other straightening mechanism (not shown) may be used to temporarily straighten the elongate body. For example, a rigid tube or mandrel may be placed in one or more lumens of elongate body (2100), which may temporarily straighten any curved sections. Straightening may occur during delivery (e.g., when used in conjunction with a left atrial appendage ligation procedure, before the pericardial space is reached), and the straightening mechanism may be withdrawn at any point to allow elongate body (2100) to return to its original configuration. The straightening mechanism may be made of any suitable material (e.g., a rigid plastic, stainless steel, a combination thereof, etc.).

In other variations, one or more pre-curved tubes or mandrels may be inserted into elongate body (2100) to create one or more curved sections. In still other variations, one or more pull wires may be disposed in, on, or around elongate body (2100) and may cause elongate body (2100) to flex or bend when one or more of the pull wires is pulled, pushed or otherwise manipulated. It should be further understood that any of the devices described here may be configured for steerability, or may be configured for robotic use (e.g., configured for use with one or more robotic or otherwise automated devices).

Lumens

The elongate bodies described here may have any suitable number of lumens. It should be appreciated that when the term "lumen" is used herein, it may be used to describe any bore or passageway extending through a length of the elongate body or other portion of the closure device. It should be appreciated that a lumen need not be entirely enclosed (i.e., the lumen may comprise one or more slots, slits, gaps or other openings along some or all of the length of the lumen). Elongate body may comprise one, two, three, four, or five or more lumens. Some or all of the lumens may extend entirely through the elongate body (i.e., from the proximal end of the elongate body to the distal end of the elongate body). Other lumens may pass through only a portion of the elongate body (e.g., from one end to an intermediate point along the elongate body, or between two intermediate points along the elongate body). For example, in the variation shown in FIG. 21, third lumen (2110) passes from the proximal end of the elongate body (2100) to an intermediate point along the length of the elongate body (2100). In this variation, one or more guidewires, visualization devices, or working devices (not shown) may be passed through third lumen (2110).

The various components of the snare loop assembly may be housed within any lumen or lumens of the elongate body. For example, in some variations, all components of the snare loop assembly may be housed in a single lumen. In other variations, different portions of the snare loop assembly may be at least partially housed in different lumens. For example, in some variations, the elongate body may comprise at least two lumens. In these variations, the free end of suture loop may pass to the handle portion through a first lumen, while the free end of the snare may pass to the handle portion through a second lumen. In variations where the suture loop has excess suture housed within the elongate body, as described in more detail below, this excess suture may be housed in any suitable lumen. For example, in some variations, the excess suture may be held in the same lumen as the free end of the suture loop, in the same lumen as the free end of the snare, or in an altogether different lumen.

In some instances, one or more of the lumens of the elongate body may be at least partially divided into one or more sub-lumens. Specifically, a lumen may be split into two or more sub-lumens along a portion of the length of that lumen. In some of these variations, a piece of separation tubing may be used to divide a lumen into two or more sub-lumens. FIGS. 22A-22D illustrate several variations of separation tubing suitable for use with the closure devices described here. Specifically, FIGS. 22A and 22B show a perspective view and a top view, respectively, of one variation of separation tubing (2200). In this variation, separation tubing (2200) may comprise first (2202) and second (2204) lumens extending therethrough. When placed inside of a lumen of the elongate body (not shown), the first (2202) and second (2204) lumens of separation tubing (2200) may act as sub-lumens within the lumen of the elongate body. In this way, the separation tubing (2200) may allow for a lumen to be a single passageway along one length of the elongate body and two or more separate passageways along another length of the elongate body.

It should be appreciated that although shown in FIGS. 22A and 22B as having two lumens ((2202) and (2204)), separation tubing (2200) may include any suitable number of lumens (e.g., one, two, three, or four or more). In this way, a lumen of the elongate body may be subdivided into any suitable number of sub-lumens along the length of the separation tubing. It should be noted that in some variations, the separation tubing may only have a single lumen passing therethrough. In these variations, the separation tubing may not divide a lumen into multiple sub-lumens, but instead may alter the size and/or shape of the lumen along a portion thereof. It should also be appreciated that some or all of the lumens of the separation tubing (2200) may only pass through a portion of the separation tubing.

In other variations, a piece of separation tubing may include one or more grooves or channels. These grooves or channels may form a fully-enclosed sub-lumen when placed inside of a lumen of an elongate body. For example, FIGS. 22C and 22D illustrate one such variation of separation tubing (2206). Specifically, FIG. 22C shows a perspective view of separation tubing (2206), which comprises lumen (2208) and channel (2210) along an outer surface of separation tubing (2206). When separation tubing (2206) is placed inside of a lumen (2211) of an elongate body (2212), as shown in a top view in FIG. 22D, channel (2210) may form an enclosed lumen which may defined in part by the separation tubing (2206) and in part by the lumen wall. It should be appreciated that the separation tubing described here may comprise any suitable number and combination of channels and/or lumens.

In some variations it may desirable to configure the separation tubing to allow one or more components of the snare loop assembly to be released therethrough. For example, in some instances a portion of the suture loop may be threaded through two or more lumens/channels of a section of separation tubing, as will be described in more detail below. In order to release the suture loop from the device, it may be necessary to remove any excess suture from separation tubing without undoing or breaking the suture loop. Thus, in some variations, the separation tubing may comprise one or more separation regions (not shown) between two or more lumens, channels, or combinations thereof. The separation regions may be constructed in any suitable manner, such as those described above with respect to the retention members. For example, in some variations the separation region may comprise a perforated region adapted to perforate and allow suture to pull therethrough as the suture loop is tightened. Alternatively, in some variations the separation region may be a thin-walled or other type of weakened region that may be configured to tear or otherwise break upon the application of force from a suture or other device component.

Tips

The elongate body generally comprises a tip portion at the distal end thereof. In some variations, the tip of the elongate body may be formed separately from the elongate body, and may be attached to the body during assembly of the device. In other variations the tip portion may be formed integrally with the elongate body as a unitary device. The tip portion may serve a number of useful functions for closure device. In some instances, the tip may be configured to be atraumatic, which may act to reduce the risk of damaging tissue as the proximal end of the elongate body is moved within the body. In other instances, the tip may allow certain portions of the snare to pass through elongate body while holding other portions in place relative to elongate body, as will be described in more detail below.

The tip portion may have the same number of lumens as the elongate body, but need not. Indeed, in some variations, the tip portion may divide one or more lumens of the elongate body into two or more sub-lumens. In some of these variations, the tip portion may house at least one portion of a piece of separation tubing. In other variations, the tip portion may alter the size or shape of one or more lumens of the elongate body.

Figure 23B:
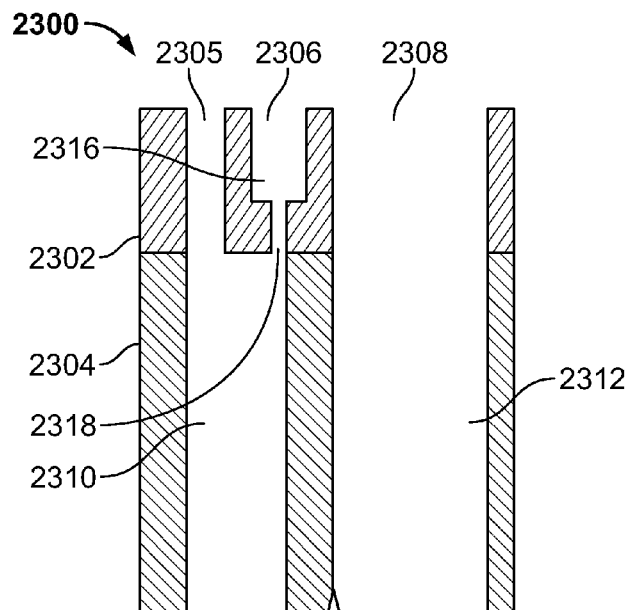
FIGS. 23B and 23C depict cross-sectional side views of the tip portion of FIG. 23A.
Figure 23C:
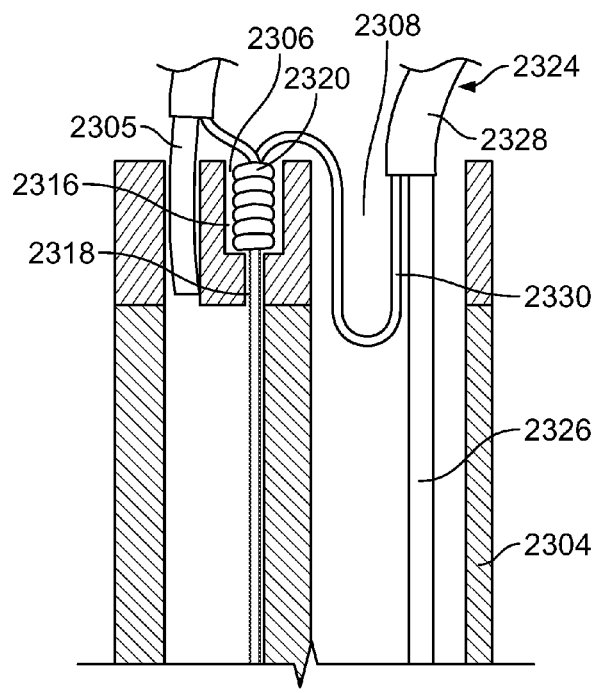

FIGS. 23A-23C show the distal end of one illustrative variation of closure device (2300). Specifically, FIG. 23A shows a front view of tip (2302) of elongate body (2304). As can be seen there, tip (2302) may comprise first sub-lumen (2305), second sub-lumen (2306), and third sub-lumen (2308). FIG. 23B shows a cross-sectional side view of elongate body (2304) and tip (2302). As shown there, first (2305) and second (2306) sub-lumens may exit into a first lumen (2310) of elongate body, while third sub-lumen may exit into a second lumen (2312).

In some variations, one sub-lumen may be configured to at least partially house a suture knot of the suture loop. For example, second sub-lumen (2306) shown in FIG. 23B may comprise a knot-receiving recess (2316) with a first cross-sectional area, and a second section (2318) with a second cross-sectional area. A suture knot (2320) of a suture loop (2330) may be placed in knot-receiving recess (2316) of second sub-lumen (2306), as shown in FIG. 23C. A free end of suture loop (2330) may pass through second section (2318) into first lumen (2310) of elongate body (2304). Additionally, the cross-sectional area of knot-receiving recess section (2316) may be different (e.g., smaller and/or differently shaped) from the cross-sectional area of the second section (2318) such that the suture knot (2320) is unable to pass from knot-receiving recess section (2316) into second section (2318). In this way, the suture knot (2320) may be prevented from moving proximally into the elongate body (2304). Additionally, because suture knot (2320) may be housed at least partially in the knot-receiving recess (2316) of second sub-lumen (2306), suture knot may be prevented from pulling into third sub-lumen (2308) when excess suture is pulled into elongate body (2304), as will be described in more detail below.

FIG. 23C also illustrates how other components of a snare loop assembly (2324) may be disposed relative to tip (2302). As shown there, snare loop assembly (2324) may comprise snare (2326), suture loop (2330), and retention member (2328). Retention member (2328) may releasably connect a portion of snare (2326) and suture loop (2330). A free end of suture loop (2330) may pass through second sub-lumen (2306) and first lumen (2310) to a handle portion (not shown), while an amount of excess suture (2330) may be housed within third-sub lumen (2308) of tip and second lumen (2312) of elongate body. At least a portion of this excess suture (2330) may be held within the elongate body by one or more suture management features (not shown) described below. Additionally, one end of snare may be fixed, temporarily or permanently, at least partially within first sub-lumen (2305), while a free end of snare (2326) may be moved at least partially through third sub-lumen (2308) of tip and second lumen (2312) of elongate to open and close the snare loop assembly (2324).

Figure 24A:
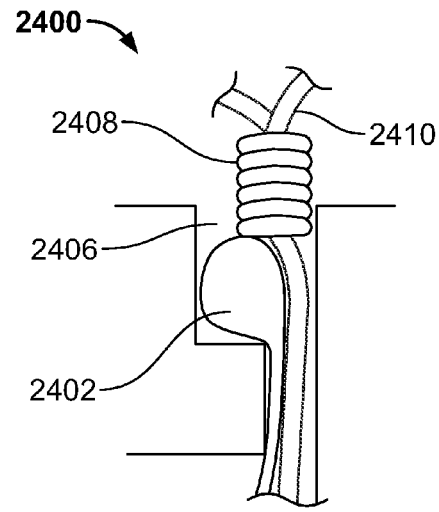
FIGS. 24A and 24B depict portions of two variations of tip portions suitable for use with the devices described here.
Figure 24B:
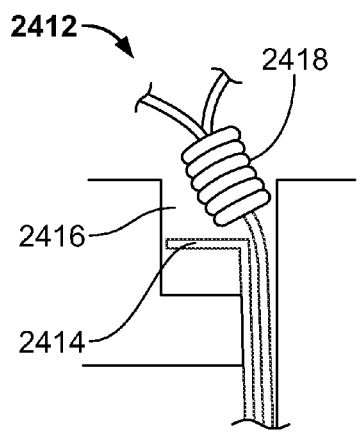

In variations where the tip of an elongate body comprises a knot-receiving recess, it may be desirable to eject or move the suture knot from the recess during or prior to tightening of the suture loop. Moving a suture knot out of the recess may improve the ability of the suture loop to tighten around tissue by improving knot placement relative to tissue. A suture knot may be displaced from the recess in any suitable manner. For example, FIGS. 24A and 24B illustrate two suitable variations by which a suture knot may be advanced from a knot-receiving recess. In a first variation, closure device (2400) may comprise a balloon (2402) or other expandable structure disposed in a knot-receiving recess (2406), as illustrated in FIG. 24A. Suture knot (2408) of suture loop (2410) may be at least partially housed in knot-receiving recess (2406) when balloon is collapsed. When balloon (2402) is expanded, it may displace at least a portion of suture knot (2408) from the knot-receiving recess (2406). In another variation, closure device (2412) may comprise a pusher (2414) at least partially disposed in a knot-receiving recess (2416), as shown in FIG. 24B. In this variation, pusher (2414) may be advanced within knot-receiving recess (2416) to push at least a portion of suture knot (2418), and in some instances the entire suture knot (2418), from the knot-receiving recess (2416).

Figure 25A:
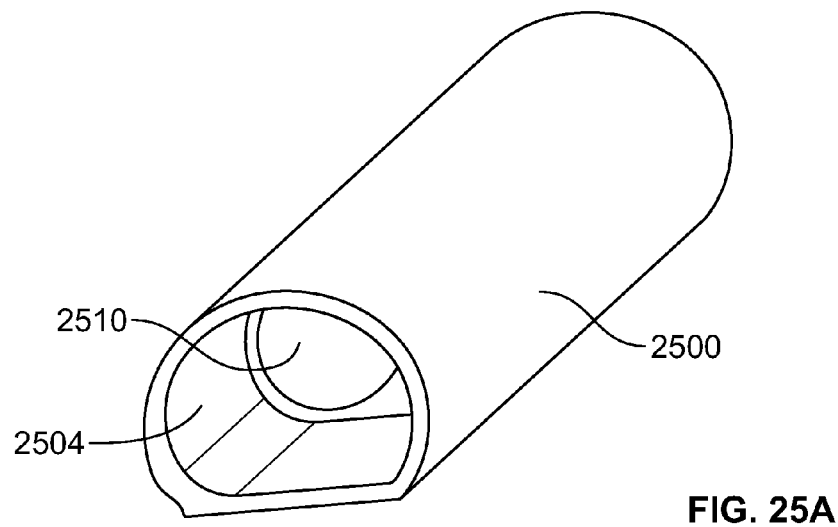
FIGS. 25A-25C depicts a perspective view, a front view, and a cross-sectional side view, respectively of an illustrative variation of a tip portion suitable for use with the devices described here.
Figure 25B:
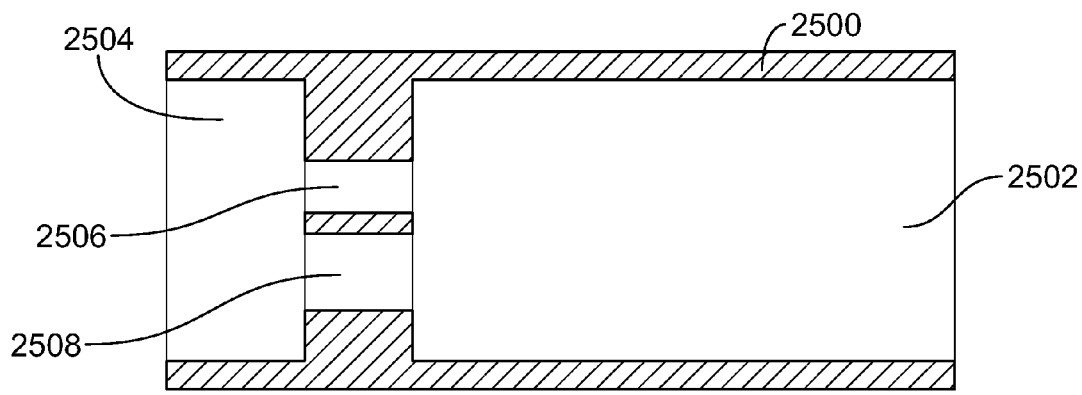
Figure 25C:
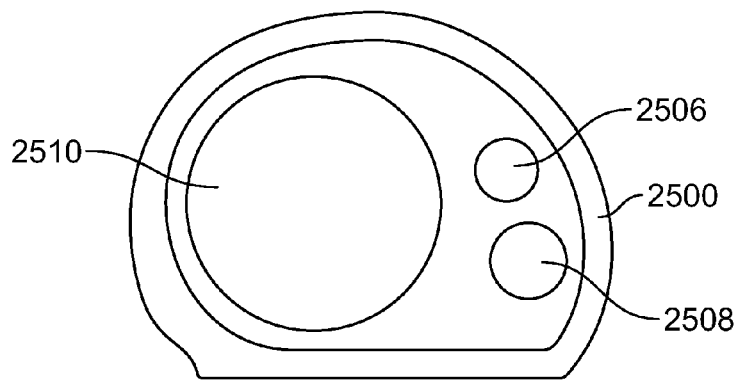

In other variations of the closure devices described here, the tip portion may comprise a distal recess. FIGS. 25A-25D illustrate one such variation of tip (2500). FIG. 25A-25C show a perspective view, a front view, and a cross-sectional side view of tip (2500). Shown there is proximal recess (2502) for receiving a distal end of the elongate body (not shown), distal recess (2504), first sub-lumen (2506), second sub-lumen (2508), and third sub-lumen (2510). While shown in FIGS. 25A-25C as being formed separately from the elongate body, it should be appreciated that the tip may be formed integrally with the elongate body.

Figure 25D:
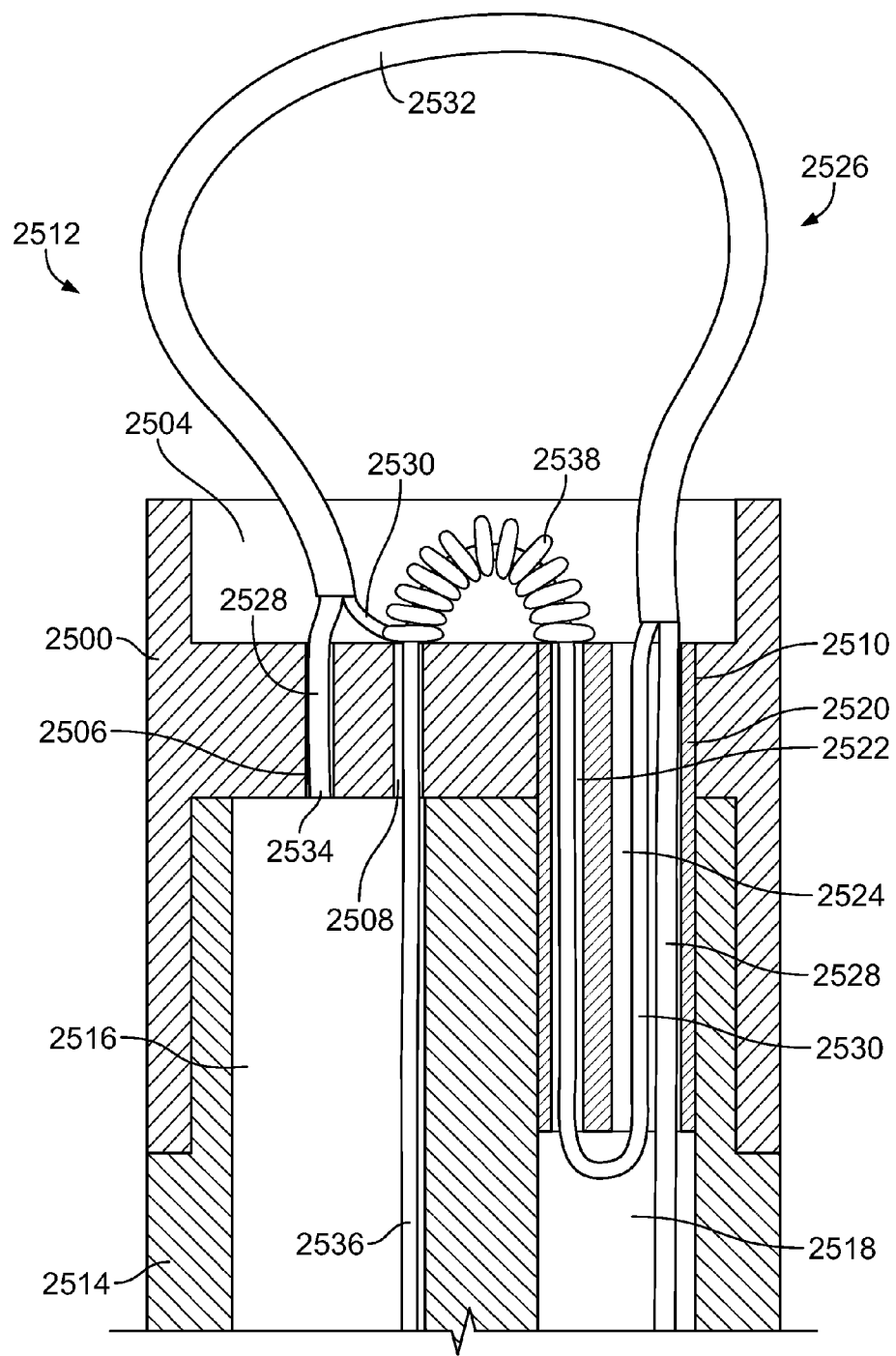
FIG. 25D illustrates a cross-sectional side view of one variation of a closure device incorporating the tip portion illustrated in FIGS. 25A-25C.

FIG. 25D illustrates a cross-sectional side view of one instance of how tip (2500) may be incorporated into a closure device (2512). Shown there is tip (2500) attached to elongate body (2514). As shown there, elongate body (2514) may comprise a first lumen (2516) and a second lumen (2518), and may be placed within the proximal recess (2502) of tip (2500). First (2506) and second (2508) sub-lumens may exit into first lumen (2516), while third sub-lumen may exit into second lumen (2518).

Closure device (2512) may further comprise separation tubing (2520) that may be disposed partially in third sub-lumen (2510) of tip (2500) and second lumen (2518) of elongate body (2514), and may divide the lumen into sub-lumens (2522) and (2524). Also shown in FIG. 25D is snare loop assembly (2526) comprising snare (2528), suture loop (2530), and retention member (2532). One end (2534) of snare (2528) may be fixedly attached to tip (2500) via first sub-lumen (2506) or may be attached in lumen (2516) through sub-lumen (2506), while a free end of the snare may be advanced or withdrawn through sub-lumen (2524) of separation tubing (2520). Similarly, a free end (2536) of suture loop (2530) may pass through second sub-lumen (2508) of tip (2500), while a portion of excess suture of suture loop (2530) may be housed in sub-lumens (2522) and (2524) of separation tubing (2520).

Suture knot (2538) may be housed in distal recess (2504). Additionally, second sub-lumen (2508) of tip (2500) and sub-lumen (2522) of separation tubing (2520) may be sized such that suture knot (2538) is unable to pass into either sub-lumen, thereby preventing suture knot (2538) from being pulled or pushed into the elongate body (2514). Additionally, by placing the ends of the suture knots against the entrances to these sub-lumens, the suture loop (2530) may be tightened around tissue while minimizing the amount of tissue that may be pulled into suture knot (2538) as the suture loop (2530) is tightened.

Excess-Suture Management

In operation of the closure devices, it may be desirable to be able to open and close a snare loop assembly without prematurely releasing the suture loop from the snare assembly. Because the size of the continuous aperture defined by the snare loop assembly changes as the snare loop assembly is opened and closed, it may be necessary for the size of the suture loop to change in order to accommodate this change in aperture size and to prevent the suture from being prematurely released from the snare loop assembly. In some variations, opening the snare loop assembly may pull suture through a slip knot to increase the size of the suture loop. This may, however, provide sufficient force to the suture loop to cause the suture to break or sever. To help prevent this undesirable outcome, the suture loop may be sized such that the suture loop is as large as or larger than the size of the aperture defined by the snare loop assembly when the snare loop assembly is in an open configuration. Thus, when the snare loop assembly is opened to a deployed configuration, the suture loop can assume a similar size without needing to advance additional suture through the suture knot. Pre-sizing the suture loop to such a size, however, may result in extra slack in the suture loop when the snare loop assembly is in a closed configuration. To help prevent the excess suture from getting entangled with or caught on anatomical structures, instruments, or other obstructions, some or all of the slack in the suture loop may be held inside of the elongate body when the snare loop assembly is opened and/or closed.

As such, the closure devices described here may comprise one or more excess-suture management features, which may be used in any suitable manner. In some instances, the feature may be configured to apply a force to the excess suture when the device is an open and/or a closed configuration. This force may act to pull the excess suture into the elongate body or may temporarily prevent excess suture from exiting the elongate body. Additionally, this force may act to prevent the excess suture from knotting or bunching up, which may potentially affect device performance. The following is a discussion of a number of different potential suture management features suitable for use for the closure devices described here. It should be appreciated that the closure devices described here may comprise any combination of these suture management features.

Suture Hooks

Figure 2:
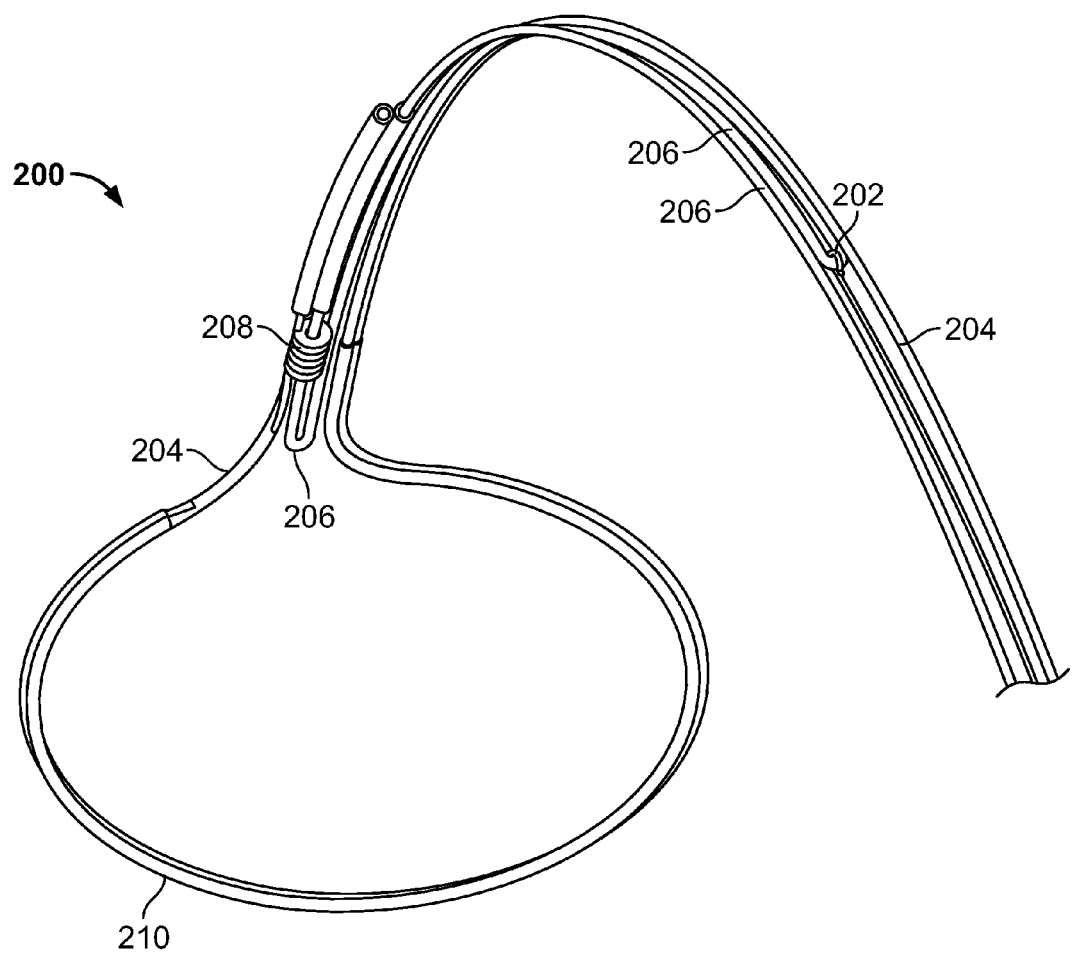
FIG. 2 is a view of a distal end of a snare loop assembly, including a suture hook.

In some variations, a suture hook may be used to hold the excess suture within the elongate body. FIG. 2 shows one such variation of a snare loop assembly (200) having suture hook (202). Also shown there is snare (204), suture loop (206) having suture knot (208), and retention member (210). As illustrated in FIG. 2, suture hook (202) may hold excess suture from suture loop (206) within an elongate body (not shown). In variations in which the elongate body has multiple lumens, suture hook (202) may hold excess suture in any suitable lumen.

In some variations the proximal end of the suture hook may be able to move relative to the elongate body when snare is advanced from or withdrawn through or within the elongate body. FIG. 10 shows a cross-sectional side view of a portion of closure device (1000) comprising elongate body (1002) with lumen (1004) disposed therethrough, and connected to interconnect (1006) of a handle (not shown). It should be appreciated that, although shown in FIG. 10 as having only one lumen (1004) disposed therethrough, elongate body (1002) may have any number and configuration of lumens as described above. Also shown in FIG. 10 is a portion of snare (1008) attached to hypotube (1009) and suture hook (1010) engaging a portion of suture loop (1012). As described above, snare (1008) may be advanced or withdrawn through or within elongate body (1002) to open or close a snare loop assembly (not shown).

When snare (1008) is advanced and snare loop assembly is opened, suture loop (1012) may pull suture hook (1010) toward the distal end of the elongate body (1002) to release some of the excess suture from the elongate body (1002) or to allow some of the excess suture to advance within the elongate body (1002). In some variations, suture hook (1010) comprises a spring (1014). Spring (1014) may stretch when suture hook (1010) moves toward the distal end of the elongate body (1002). Conversely, closing the snare loop assembly may reduce the force applied to suture hook (1010) by suture loop (1012), which may allow the return force of the spring (1014) to pull suture hook (1010) proximally. This, in turn, may pull any excess suture back into or through a portion of elongate body (1002). Because excess suture is released from elongate body (1002) when the snare loop assembly is opened and withdrawn into elongate body (1002) when snare loop assembly is closed, the suture loop (1012) may be maintained at the same size as the snare loop assembly. Additionally, because the excess suture is doubled back into the elongate body when held by suture hook (1010), suture hook (1010) need only to be configured to move half as much as snare (1008) in order to maintain the suture loop (1012) at the same size as snare loop assembly.

It should be appreciated that although shown in FIG. 10 as having one end attached to suture hook (1010) and the other end attached to interconnect (1006) (which will be described in more detail below), spring (1014) may be attached to any suitable portion or portions of the closure device (1000). In some variations, the spring may be attached to one or more elements of the handle, as will be described in more detail below. In other variations, the spring may be attached to one or more portion of the elongate body (1002). In still other variations, suture hook (1010) does not comprise a spring at all. In some of these variations, at least a portion of the suture hook (1010) may be capable of stretching or otherwise deforming to allow excess suture to be pulled out of elongate body (1002). For example, suture hook (1010) may comprise an elastic material or combination of materials that are capable of both stretching and returning to an unstretched state. In these instances, as snare loop assembly opens, the elastic material or materials may stretch to allow excess suture to be pulled out of or through a portion of elongate body (1002). When snare loop assembly is closed, the suture hook (1010) may return to its unstretched state, and may thereby pull the excess suture back into or through a portion of the elongate body (1002).

In variations where excess suture from suture loop (1012) is held within the elongate body by suture hook (1010), an additional step may be required to release suture loop (1012) from snare loop assembly. Once snare loop assembly is advanced over a target tissue and closed over the tissue, there may be excess suture from suture loop (1012) held in the elongate body by suture hook (1010). Before suture loop (1012) can be released from the snare loop assembly, this slack may first need to be removed. To achieve this, the excess suture may be pulled through a suture knot (not shown) to reduce the size of suture loop (1012). In some variations, suture hook (1010) may be configured to deform once sufficient force is applied thereto. Furthermore, in some variations suture hook (1010) comprises a stop (1016) that prevents suture hook (1010) from moving distally beyond a certain point. Thus, as suture is withdrawn through suture knot and the size of suture loop (1012) decreases, suture loop (1012) places an increasing force on suture hook (1010). Suture hook (1010) may move toward the distal end the elongate body (1002) until stop (1016) engages interconnect (1006). It should be noted that stop (1016) may engage any suitable structure in closure device (1000). When stop (1016) engages interconnect (1006), suture hook (1010) is held in place and eventually the force applied by suture loop (1012) may cause the end of suture hook (1010) to deform and release the remaining excess suture.

After suture loop (1012) has been released from suture hook (1010) and the excess suture has been removed from suture loop (1012), any additional suture that is pulled through suture knot may begin to release suture loop (1012) from the snare loop assembly. If the snare loop assembly is closed around tissue before releasing suture loop (1012), any excess suture may be held within the elongate body (1002). Thus, any excess suture removed from the suture loop (1012) is housed within the elongate body (1002). Because this suture is housed within the elongate body (1002), it will not rub against or otherwise make contact with tissue disposed outside of the elongate body (1002). Additionally, as the suture loop (1012) is released from the snare loop assembly, the suture is released directly into contact with the tissue. Thus, a user may both remove excess suture from the suture loop (1012) and release the suture loop (1012) from the snare loop assembly without rubbing or sliding against the tissue. Because tissue may be damaged when suture slides or rubs against tissue, the closure devices described here may help minimize damage caused to tissue in this way. Once the suture loop (1012) is completely separated from the snare loop assembly, it may be tightened to ligate the target tissue.

As shown in FIG. 10, snare (1008) and suture hook (1010) may be disposed in the same lumen (1004) of elongate body (1002), but need not be. In variations where the snare (1008) is disposed in the same lumen (1004) as suture hook (1010), there may be a risk of the snare (1008) becoming entangled with the suture hook (1010). Additionally, because the suture hook (1010) need only move half as much as snare (1008) when opening and closing the snare loop assembly, the snare (1008) may rub against spring (1014), which may in turn cause spring (1014) to rub against the inner wall of lumen (1004). This friction may impede the actuation of the closure device (1000), and thus increase the force a user must provide to actuate the device.

In some variations, the closure device may be configured to help prevent the suture hook from tangling with snare. FIG. 11 shows one such variation of a middle portion of closure device (1100). Shown there is elongate body (1102) attached to interconnect (1104), hypotube (1106), snare (1108), spring (1110), suture hook (1112), sleeve (1114), and suture loop (1116). The free end of snare (1108) may be attached to hypotube (1106), as described above. Additionally, suture hook (1112) may be attached to hypotube (1106) via spring (1110). Spring (1110) may additionally be disposed around snare (1108), which may help prevent spring (1110) from tangling with snare (1108). Additionally, this may reduce the amount of space taken up by snare (1108) and spring (1110), which may, in turn, allow snare and spring to be placed within a smaller lumen without adding to the amount of rubbing that occurs between the spring and the inner wall of lumen.

Sleeve (1114) may also act to help prevent tangling between suture hook (1112) and snare (1108). Sleeve (1114) may have two or more lumens. Suture hook (1112) may pass through one lumen, while snare (1108) may pass through a separate lumen. In some variations, sleeve (1114) may be attached to snare (1108). Sleeve (1114) may be attached in any suitable manner (e.g., bonding, welding, mechanical attachment, etc.). In these variations, sleeve (1114) may act as a stop to help release suture loop (1116) from suture hook (1112). As excess suture is removed from suture loop (1116), as described above, spring (1110) may stretch until it comes into contact with sleeve (1114). Once in contact with sleeve, spring (1110) may be held in place while the force exerted on suture hook (1112) by suture loop (1116) may cause suture hook (1112) to deform, and may thereby release suture loop (1116) from suture hook (1112).

Separation Tubing

In some instances it may be desirable to maintain excess suture within the elongate body without the need for a suture hook. Under certain circumstances, as a portion of the elongate body is advanced into or through the body, one or more portions of the elongate body may bend or flex to allow the snare loop assembly to reach a target location. Bending or flexing the elongate body, however, may impede movement of the suture hook or spring, which may potentially impede the snare hook's ability to maintain excess suture loop within the elongate body. Thus, it may be desirable to have a suture maintenance feature that is located in a distal portion of the elongate body.

Figure 26A:
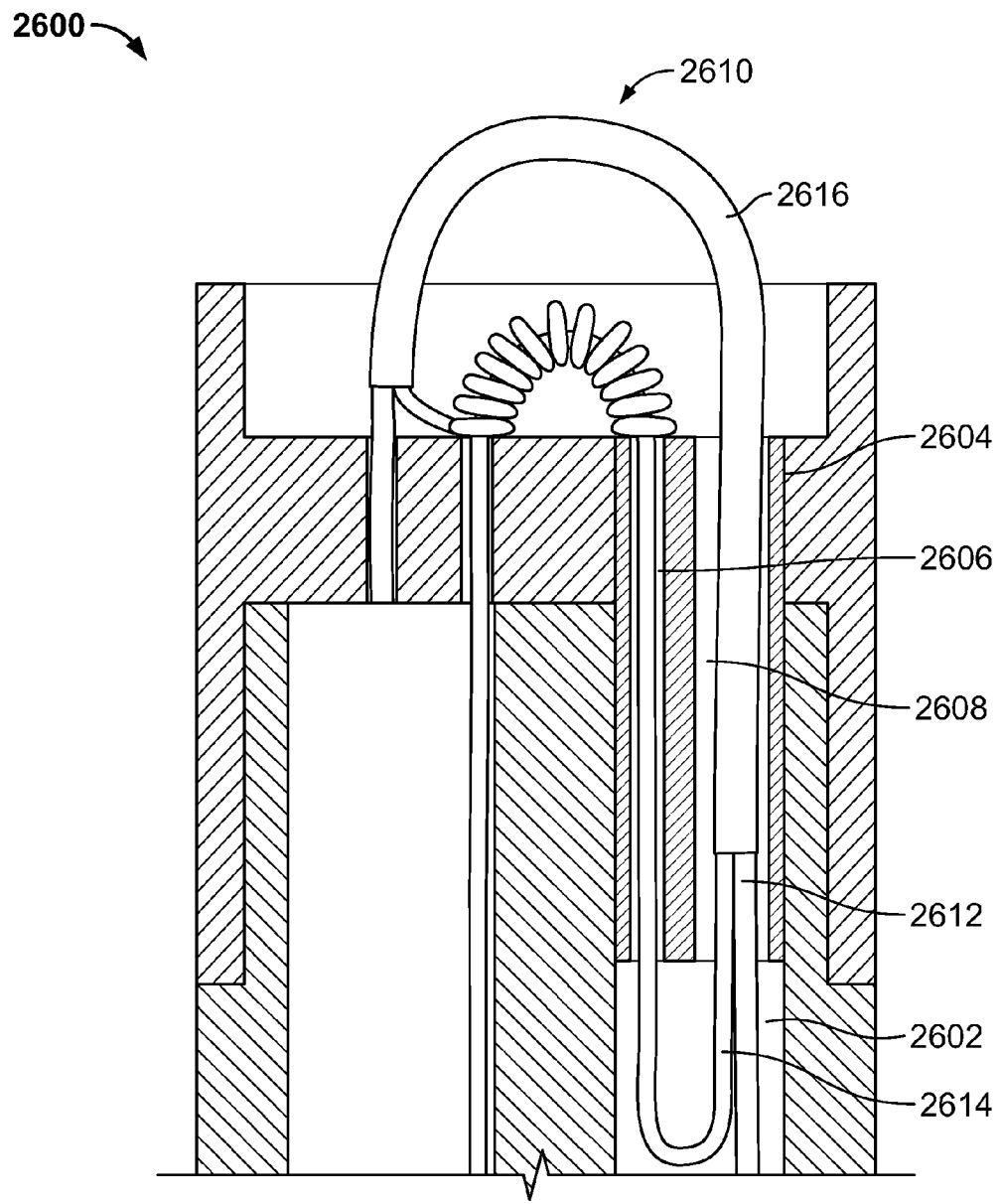
FIGS. 26A and 26B show an illustrative variation of a closure device comprising separation tubing.
Figure 26B:
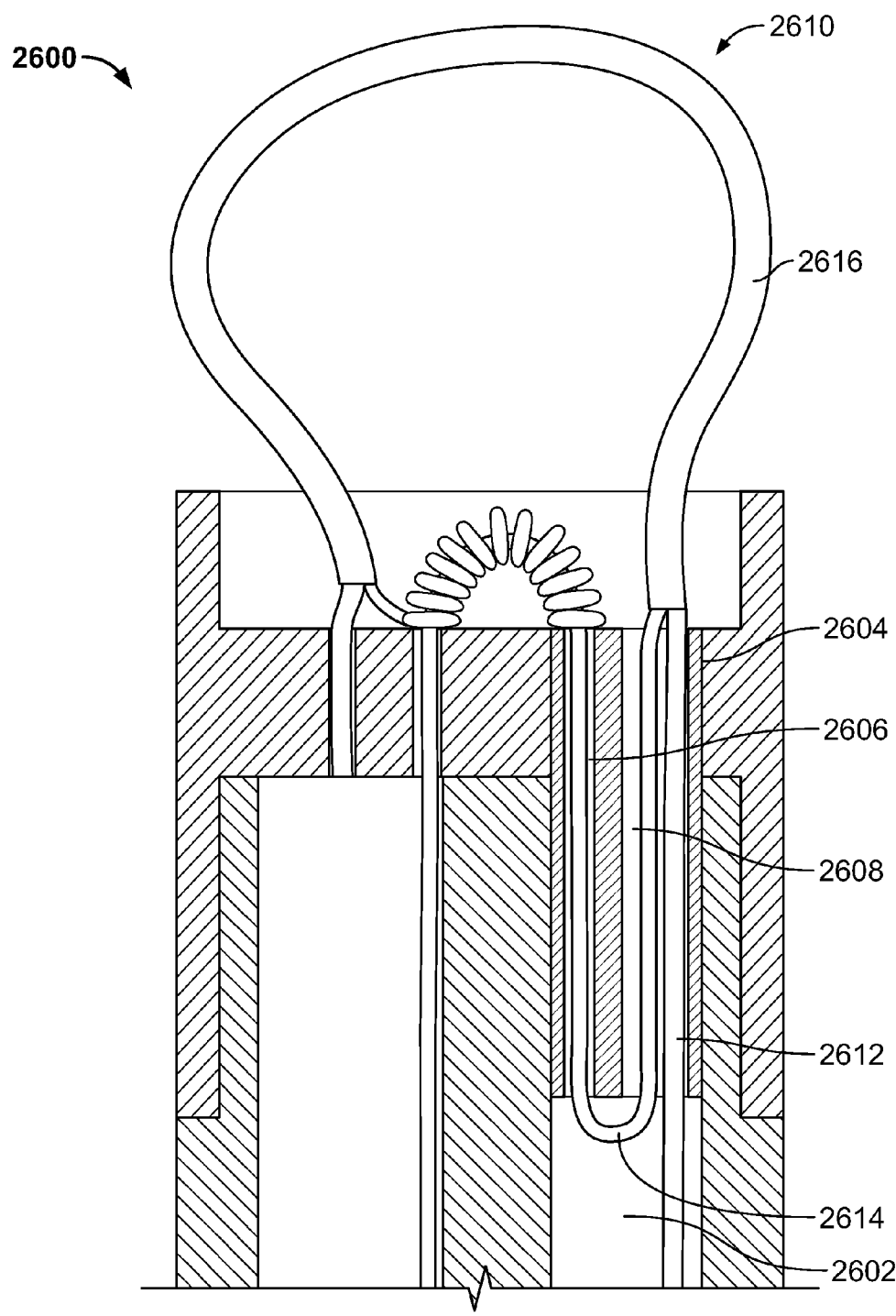

As such, in some variations of the closure devices described here, one or more pieces of separation tubing may be used to help maintain excess suture within the elongate body, and may thereby limit the exposure or release of excess suture out of the elongate body. FIGS. 26A and 26B show cross-sectional side views one such variation of a closure device (2600). Shown there is lumen (2602) with separation tubing (2604) disposed therein. Separation tubing (2604) may divide lumen (2602) into a first sub-lumen (2606) and a second sub-lumen (2608). Closure device (2600) may comprise a snare loop assembly (2610), which may comprise snare (2612), suture loop (2614), and retention member (2616). As shown in FIGS. 26A and 26B, suture from suture loop (2614) may pass through first sub-lumen (2606) into lumen (2602), where it may be connected to snare (2612) via retention member (2616). Snare (2612) may be advanced or withdrawn through second sub-lumen (2608) to open or close the snare loop assembly, respectively. When snare loop assembly (2610) is in a closed configuration, as shown in FIG. 26A, excess suture from suture loop (2614) may be held in snare lumen (2602) and first sub-lumen (2606). When snare is advanced to open the snare loop assembly, some of the suture held within the snare lumen may be advanced into the second sub-lumen (2608) to allow the snare loop assembly to open, as shown in FIG. 26B. The presence of separation tubing, however, may prevent the excess suture from being pushed or pulled out of the tip of the closure device.

When separation tubing is employed to maintain excess suture within elongate body, it may be necessary for the separation tubing to comprise one or more separation regions to release the excess suture from the elongate body. These separation regions, as described in more detail above, may allow suture to pass therethrough during release of the suture loop. Specifically, as excess suture is removed from the suture loop (i.e., as suture is pulled through the suture knot to tighten the suture loop), the suture may be pulled through the separation regions, allowing the excess suture to span the space between the sub-lumens of the separation tubing.

It should be appreciated that any suitable piece of separation tubing as described in more detail above may be used to maintain excess suture within the elongate body. It should also be appreciated that separation tubing may be used in conjunction with a suture hook, as described above, or one or more additional excess-suture management features. For example, in some instances separation tubing may be used in conjunction with one or more suture tubes. Generally, a suture tube has a first end that may be connected to the separation tubing, a second end that may be connected to a portion of the snare loop assembly, and may temporarily hold excess suture therein. The suture tube may be made from any suitable material (e.g., pebax, tecothane, nylon, or the like), and may be comprise one or more separation regions which may allow the excess suture to be removed from the suture tube.

Figure 27:
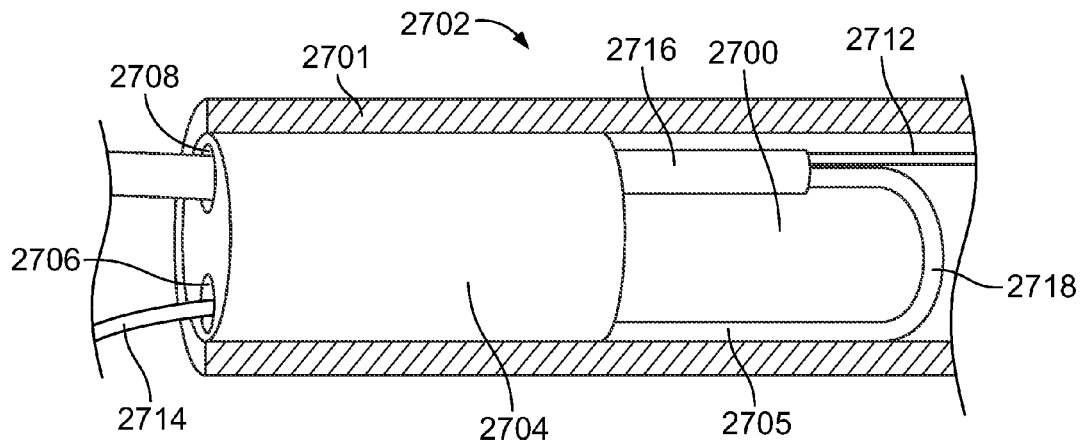
FIG. 27 depicts an illustrative variation of a closure device comprising separation tubing and a suture tube.

FIG. 27 shows a partial cutaway view of one such variation of a closure device (2702) comprising elongate body (2701), separation tubing (2704) and a suture tube (2705). Shown there is separation tubing (2704), which divides lumen (2700) into first sub-lumen (2706) and second sub-lumen (2708). Also shown there is snare loop assembly comprising snare (2712), suture loop (2714), and retention member (2716) at least temporarily connecting snare (2712) and suture loop (2714). As shown in FIG. 27, suture tube (2705) may releasably house a portion of suture loop (2714). One end of suture tube (2705) may be attached to the separation tubing (2704), and the other end may be attached to a portion of the snare loop assembly (e.g., attached to snare (2712) or retention member (2716)). By virtue of this attachment, one end of the suture tube (2705) may be fixed relative to the closure device (2702) while the other end may move with snare (2712) and closure element (2716) as the snare loop assembly is moved between a closed configuration and an open configuration.

Figure 28A:
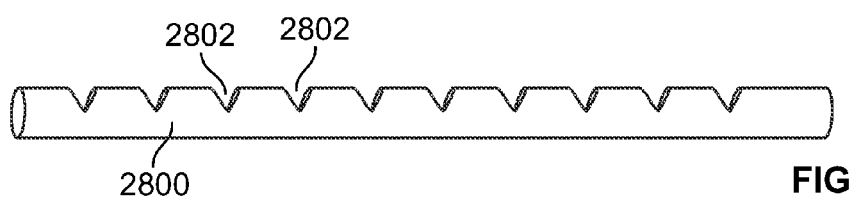
FIGS. 28A and 28B depict a variation of a suture tube suitable for use with the devices described here.
Figure 28B:
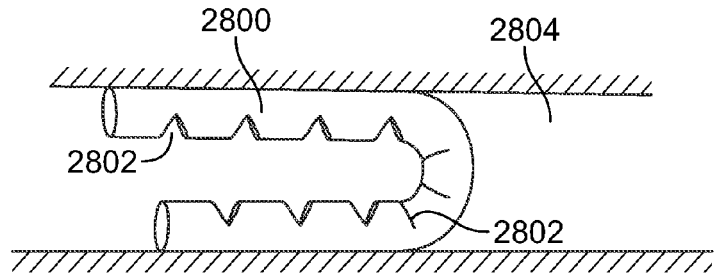

When placed in lumen (2700), suture tube (2705) may double back upon itself at bend (2718). In this way, the portion of suture loop (2714) temporarily housed in suture tube (2705) may be held in the doubled-back suture tube (2705), which may help prevent the excess suture held within lumen (2700) from bunching. The position of bend (2718) may move as the snare loop assembly is changed between opened and closed configurations. Additionally, in some instances the suture tube (2705) may have a tendency to return to an unbent shape, which may also give the suture tube (2705) tendency to twist and kink at points other than bend (2718). As such, suture tube may comprise one or more features that may help reduce twisting or kinking. For example, in some variations, tube comprises a plurality of cut or slits that may act as relief areas. FIGS. 28A and 28B show one such variation of suture tube (2800). FIG. 28A shows suture tube (2800) comprising v-shaped cuts (2802) along one side thereof. Each v-grooved cut (2802) reduces the rigidity of suture tube (2800) along that side, and may make the suture tube (2800) more likely to bend or flex at that cut (2802). Thus, when suture tube (2800) is placed within a lumen (2804), as shown in FIG. 28B, and doubles back at bend (2806), some of the v-shaped cuts (2802) may be essentially closed. As such, the v-shaped cuts (2802) may reduce the straightening force of the suture tube (2800), and may thereby alter the tendency of the suture tube (2800) to kink or twist.

While shown in FIGS. 28A and 28B as being v-shaped, the cuts may be any suitable shape (e.g. semi-circular, semi-oval, etc.).

Figure 29:
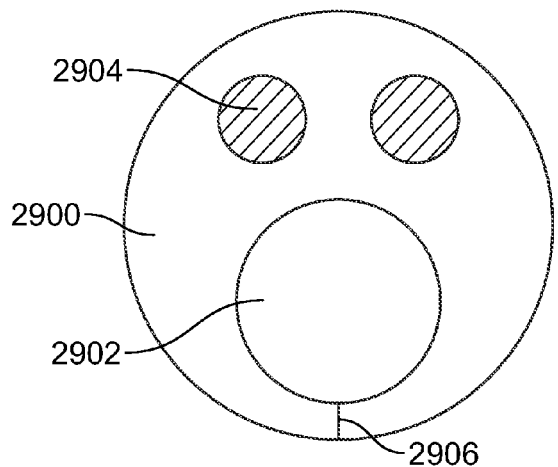
FIG. 29 depicts a cross-sectional side view of a suture tube suitable for use with the devices described here.

In other variations, the suture tube may comprise one or more strengthening members that may affect the rigidity of one or more portions of the suture tube. FIG. 29 illustrates a cross-sectional view of one such variation of suture tube (2900). Shown there is suture tube (2900), comprising suture lumen (2902), two strengthening members (2904), and separation region (2906). The strengthening members (2904) provide extra rigidity to a portion of the suture tube (2900). As such, when suture tube (2900) is doubled-over for placement in a snare lumen, the side of suture tube (2900) containing the strengthening member (2904) will have more resistance to bending, which may allow suture tube (2900) to better resist twisting and kinking. Additionally, strengthening members (2904) may increase the column strength of the suture tube (2900), such that the tube may be more easily moved as the snare is advanced or retracted. Strengthening members may be any suitable structures, such as, for example a wire made from a nickel titanium alloy, steel, a polymer, or the like. While shown in FIG. 29 as having two strengthening members (2904), it should be appreciated that the suture tube may comprise any suitable number of strengthening members (e.g., one, two, or three or more)

Pulley Suture

Figure 30A:
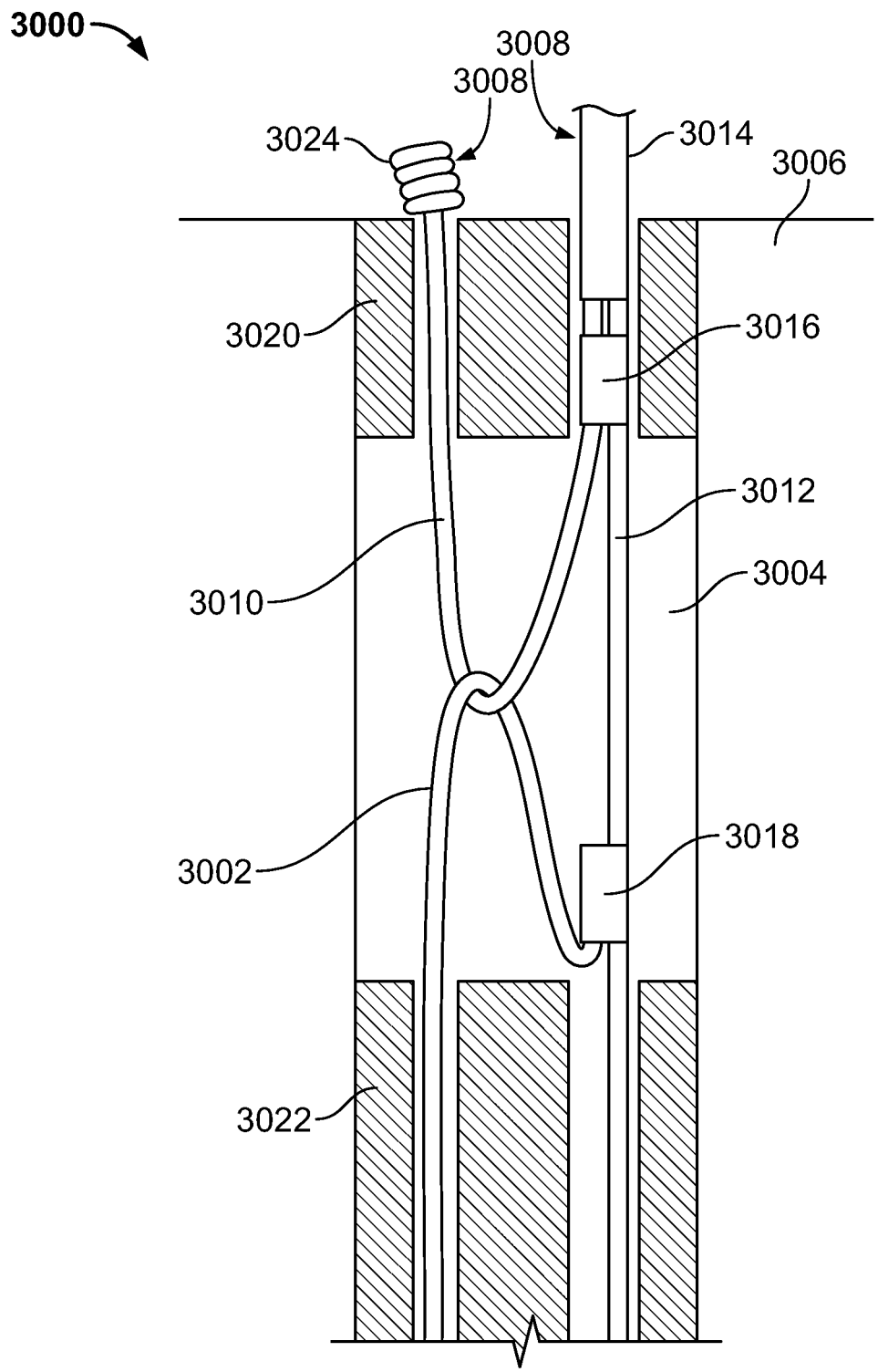
FIGS. 30A-30D depict a variation of the closure devices described here comprising a pulley suture.

In still other variations, the snare loop assembly may comprise a second suture, a pulley suture, that may engage a portion of the suture loop to help hold excess suture. Generally, one end of the pulley suture may be fixedly attached to a portion of the closure device (e.g., the handle or the elongate body) while the other end may be temporarily or permanently attached to the snare loop assembly. In some variations, the body of the pulley suture may be looped around or doubled back over a portion of suture loop to help hold a portion of the suture loop in the elongate body. FIGS. 30A-30D depict one variation of closure device (3000) comprising a pulley suture (3002) that may be used to hold a portion of a suture loop (3010) within a lumen (3004) of an elongate body (3006). Shown in FIG. 30A is snare loop assembly (3008) comprising suture loop (3010), snare (3012), retention member (3014), first suture lock (3016), second suture lock (3018), first separation tubing (3020), and second separation tubing (3022). While shown in FIG. 30A as having first (3020) and second (3022) separation tubing segments, closure device (3000) may comprise any number of separation tubing segments (e.g., zero, one, two, or three or more). Additionally, for clarity's sake first (3020) and second (3022) separation tubing segments are not shown in FIGS. 30B and 30C.

Figures 30B, 30C:
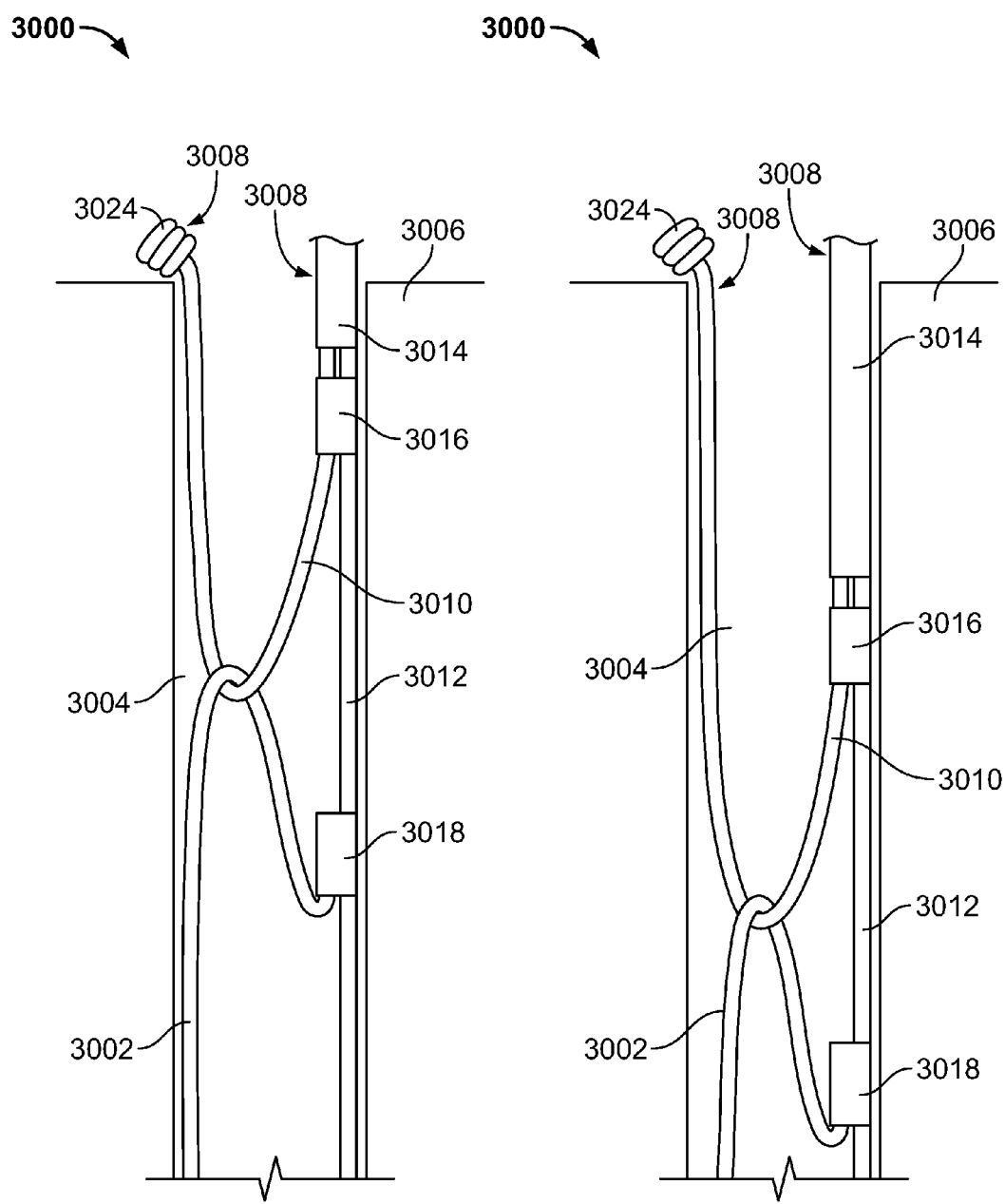

As mentioned above, one end (not shown) of pulley suture (3002) may be fixedly attached to a portion of the handle (e.g., a suture fob, as will be described in more detail below) while the other end may be temporarily attached to snare (3012) via second suture lock (3018) (suture locks will be described in more detail below). Pulley suture (3002) may also be doubled-back over a portion of suture loop (3010) between knot (3024) and second suture lock (3018), as shown in FIGS. 30A-30C. This engagement may allow excess suture to be advanced through elongate body (3006) when snare (3008) is advanced (as shown in FIG. 30B), while pulling excess suture distally into elongate body when snare (3008) is retracted (as shown in FIG. 30C). Because both suture loop (3010) and pulley suture (3002) are each temporarily attached to snare (3008) (by virtue of first (3016) and second (3018) suture locks, respectively), the sutures may be moved the same distance when snare (3008) is moved. This movement may also advance or retract the point of overlap between the two sutures when the snare is advanced or retracted, respectively.

In order to release the suture loop (3010) from the closure device (3000), it may be necessary to terminate the engagement between the pulley suture (3002) and suture loop (3010). This engagement may be terminated in any manner. In some variations the pulley suture may be released from suture lock and removed from the elongate body by pulling on one end of the pulley suture (3002). Indeed, pulley suture (3002) may be configured to pull out of or otherwise separate from the second suture lock (3018) upon application of a certain force to the pulley suture. As shown in FIGS. 30A-30C, pulley suture (3002) may double back as it enters second suture lock (3018). This may help release pulley suture (3002) from second suture lock (3018) as the change in direction may increase the shear force applied by the pulley suture (3002) to the second suture lock (3018). Additionally, first suture lock (3016) may be configured to release suture loop (3010) when a certain force is applied to the suture loop. To help prevent premature release of the suture loop (3010) from retention member (3014), the closure device (3000) may be configured such that the release force for the second suture lock (3018) is less than the release force for the first suture lock (3016), but need not be.

Figure 30D:
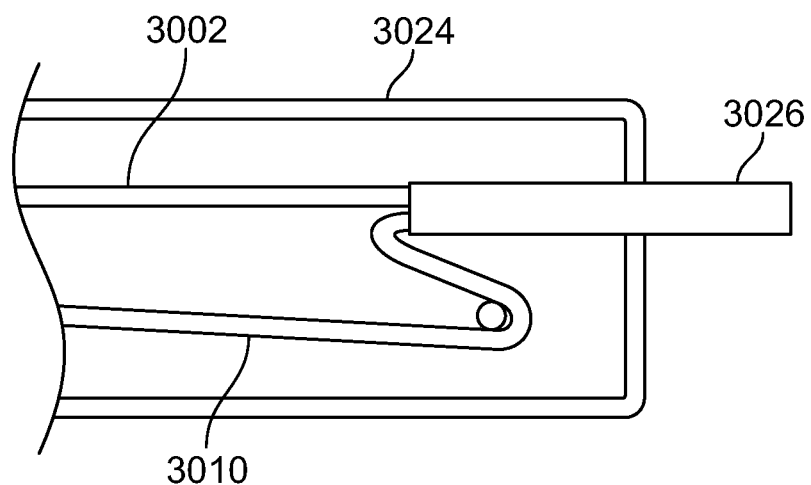

In order to release pulley suture (3002) from snare (3008), one end of pulley suture (3002) may be attached to one or more portions of the device's handle. For example, FIG. 30D shows one variation of a portion of handle (3024) of closure device (3000). As shown there, an end of pulley suture (3002) and an end of suture loop (3010) may be attached to suture fob (3026). While shown in FIG. 30D as attached to the same suture fob, it should be appreciated that pulley suture (3002) and suture loop (3010) need not be attached to the same handle component. In variations where the pulley suture (3002) and the suture loop (3010) are attached to the same handle component, such as the variation shown in FIG. 30D, the suture loop (3010) may comprise slack/excess suture inside of the handle (3024). Thus, when suture fob (3026) is pulled away from handle (3024), the pulley suture (3002) may be placed under tension before the suture loop (3010) is placed under tension. In this way, as the suture fob (3026) is pulled, the closure device (3000) may be configured to release the pulley suture (3002) from second snare lock (3018) prior to tightening and releasing the suture loop (3010).

Figure 15:
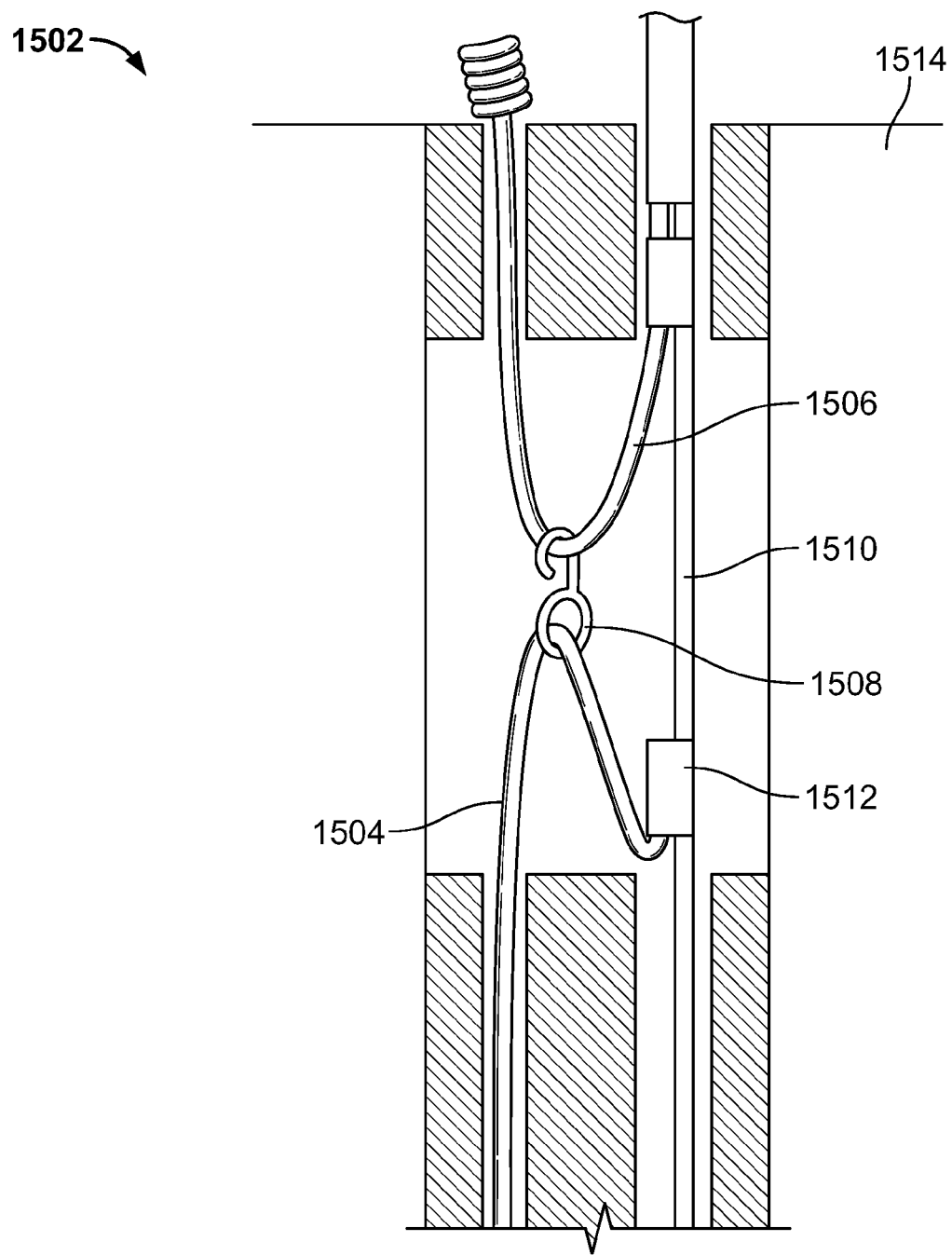
FIG. 15 shows a cross-sectional side view of a portion of one variation of the closure devices described here comprising a pulley suture.

FIG. 15 shows another variation of closure device (1502) comprising a pulley suture (1504). In this variation, pulley suture (1504) may be releasably connected to suture loop (1506) via deformable link (1508). One end of pulley suture (1504) may be attached to snare (1510) via first suture lock (1512), while the other end of the pulley suture (1504) may be fixedly attached to any suitable portion of the device (e.g., one or more portions of the handle or the elongate body). As in the other variations described above, pulley suture (1504) may be advanced or withdrawn with snare (1510) to help hold a portion of the suture loop (1506) inside of elongate body (1514).

To release the engagement between pulley suture (1504) and the suture loop (1506), the suture loop (1506) may be pulled away from the pulley suture (1504). This may be done in any suitable manner, such as, for example, tightening the suture loop (1506) or pulling one end of pulley suture (1504) relative to the suture loop (1506). As the suture loop (1506) and pulley suture (1504) are pulled away from each other, the two sutures may apply one or more forces to the deformable link (1508). These forces may cause the deformable link (1508) to deform, which may release the engagement between the suture loop (1506) and pulley suture (1504).

Force Reduction

In some instances, when a suture hook or other suture maintenance feature pulls and holds excess suture in an elongate body, it may exert one or more forces on the suture loop. This force applied to the suture loop may, in some instances, cause the suture loop to prematurely disengage from the snare loop assembly. This is illustrated in FIG. 12. Shown there is the distal end of closure device (1200) comprising snare loop assembly (1202) and suture hook (1204). Snare loop assembly comprises suture loop (1206) with suture knot (1208) and releasably coupled to snare (1210) via retention member (1212). When suture loop (1206) is pulled into an elongate body (not shown) by suture hook (1204), suture hook (1204) may place one or more tensile forces (1214) on the suture of suture loop (1206). These tensile forces may be translated into inwardly directed forces (1216) in the portion of suture loop (1206) disposed within snare loop assembly (1202). These inwardly directed forces (1216) may cause suture loop (1206) to disengage the suture loop (1206) from the retention member (1212), thereby releasing suture loop (1206) from snare loop assembly (1202) prematurely.

In order to prevent this problem, the snare loop assembly may comprise one or more suture locks. FIGS. 13A-13C illustrate one such variation of a closure device (1300). FIG. 13A shows a cross-sectional side view of closure device (1300) comprising snare loop assembly (1302), suture hook (1304), and suture lock (1306). Snare loop assembly (1302) may comprise suture loop (1308) with suture knot (1310) and coupled to snare (1312) via retention member (1314). FIG. 13B shows a front view of suture lock (1306). Shown there is suture lock (1306) comprising first lumen (1316), second lumen (1318), and slit (1320). Generally, at least a portion of snare (1312) may pass through first lumen (1316), while at least a portion of suture loop (1308) may pass through second lumen (1318). In some variations, force-reducing element (1306) may be attached to snare (1312) via first lumen (1316).

Generally, second lumen (1318) of force-reducing element (1306) may be configured to compress at least a portion of suture loop (1308). Because suture generally comprises a braided material disposed around a strength member, portions of a suture may be compressed without significantly affecting its strength. Second lumen (1318) may have a cross-sectional area that is smaller than the cross-sectional area of the suture. Thus, a portion of suture loop (1308) may be advanced through or otherwise placed in the second lumen (1318), and the narrow cross-sectional area of second lumen (1318) may act to compress the portion of suture loop (1308) disposed within second lumen, as shown in FIG. 13C. The compressed portion of suture loop (1308) may cause the suture loop (1308) to resist being pulled or pushed through force-reducing element (1306). More specifically, the uncompressed portions of suture loop (1308) may abut against the outer surface of the force-reducing element, and this abutment may resist movement of suture through the second lumen (1318).

Compression of a portion of suture loop (1308) may help prevent suture loop (1308) from prematurely releasing from snare loop assembly (1302). As described above with respect to FIG. 12, tensile forces placed on a suture loop may be translated into one or more forces that may cause a suture loop to disengage from a snare loop assembly. A force-reducing suture lock (1306) may help reduce or eliminate the forces applied to the portion of suture loop held by snare loop assembly (1302). More specifically, the compression of the portion of suture loop (1308) disposed within second lumen (1318) may prevent or reduce the transmission of the tensile force through force-reducing element (1306). As noted above, the compression of suture loop (1308) may cause the suture loop (1308) to resist movement through force-reducing element (1306). Thus, when suture hook (1304) applies a tensile force to suture loop (1308), as described above, this tensile force may attempt to pull suture through force-reducing suture lock (1306), but any such movement is resisted by the compression caused by force-reducing element (1306). As a result, some or all of the tensile force is, in effect, dissipated by trying to pull suture through force-reducing suture lock. This, in turn, may reduce or completely remove any force experienced by the suture on the other side of force-reducing element. Thus, force-reducing suture lock (1306) may reduce or remove the forces that may cause the suture loop (1308) to prematurely release form the snare loop assembly (1302).

Force-reducing suture lock (1306) may comprise one or more slits (1320) or other openings. These slits may allow suture loop (1308) to pass therethrough when it is ready to be deployed. These slits may have any suitable configuration, such as those described in U.S. patent application Ser. No. 12/055,213. Generally, once suture loop (1308) is tightened to remove excess suture from suture loop (1308), the suture loop (1308) may be tightened further, which may cause a portion of the suture loop (1308) to pass through the slit or other opening. As suture passes through the slit, suture loop (1308) may be released from force-reducing suture lock (1306).

In some variations, a force-reducing suture lock may be made from one or more pieces of shrink tubing. In these variations, a portion of the snare and the suture loop may be threaded through one or more lumens of the shrink tubing. One or more stimuli (e.g., heat) may be applied to the shrink tubing, which may cause the shrink tubing to get smaller. This reduction in size may act to hold and connect suture loop and snare.

Handles

Figure 3A:
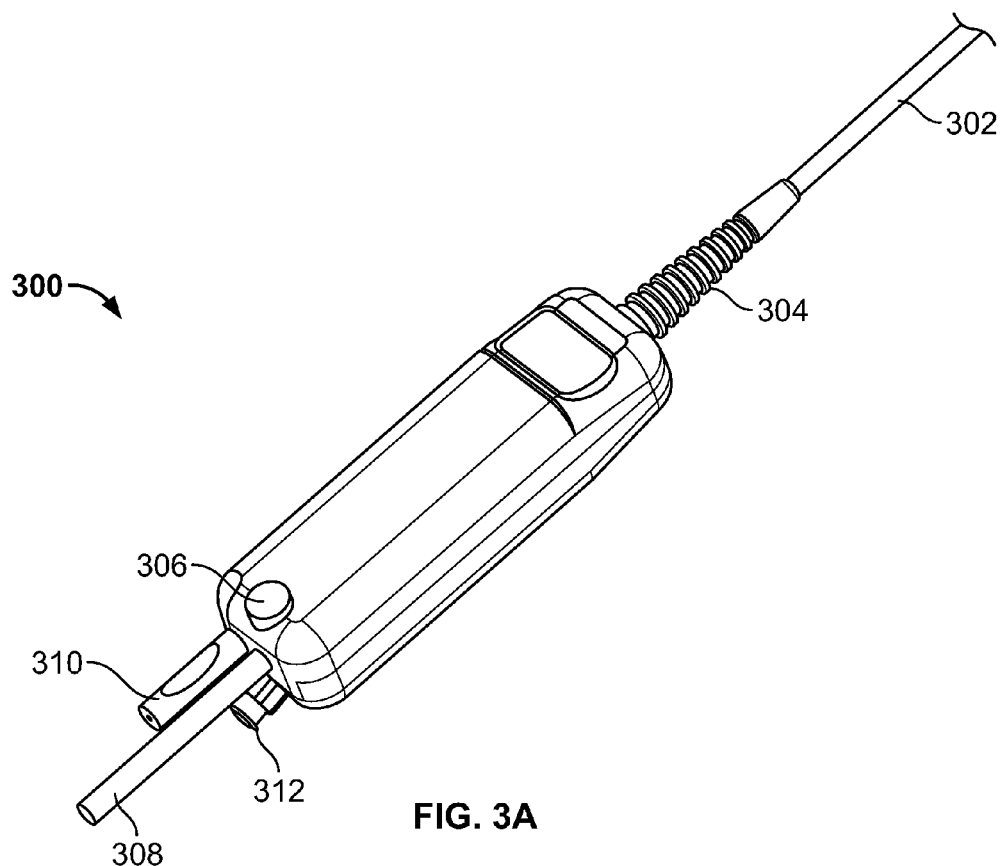
FIG. 3A is a perspective view of one variation of a handle suitable for use with the devices described here.
Figure 3B:
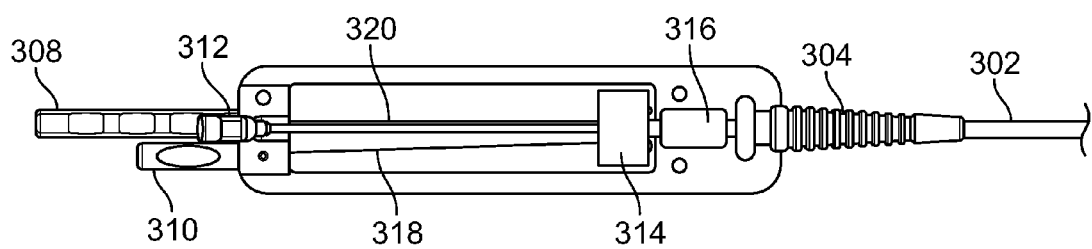
FIG. 3B is a cross-sectional bottom view of the handle shown in FIG. 3A.

Handles or proximal controls that are capable of facilitating removal of excess suture from a suture loop and releases of suture loop from snare loop assembly are provided. Handles having one or more ergonomic features or configurations to help facilitate and improve the use thereof are also described herein. FIGS. 3A and 3B show one suitable variation of handle (300). FIG. 3A shows a perspective view of handle (300) attached to elongate body (302). Also shown there is strain relief portion (304), snare lock (306), snare control (308), suture fob (310), and guidewire introducer (312). FIG. 3B shows a cross-sectional bottom view of handle (300). Also shown there is interconnect (314), locking collar (316), suture (318) and snare (320). Generally, suture (318) may be attached to suture fob (310), which may be pulled away from the handle. Pulling suture fob (310) may tighten the suture loop (not shown), and this tightening may pull excess slack from the suture loop. Once any excess slack has been removed from the suture loop, a user may continue to tighten the suture loop to release the suture loop from the snare loop assembly (not shown). Similarly, snare (320) may be attached to snare control (308), which may in turn be used to control a snare and/or a snare loop assembly. As snare control (308) is moved proximally or distally relative to handle (300), a portion of snare (320) may be moved proximally or distally through elongate body (302). This, in turn, may cause a snare loop assembly to move between an open and a closed configuration, as described in more detail above.

While shown in FIG. 3B as having a locking collar (316), handle (300) need not. In variations that include a locking collar (316), locking collar (316) may be attached to elongate body (302) and held by handle (300) to help prevent elongate body (304) from being disengaged from handle (300). Similarly, while shown in FIGS. 3A and 3B as having a strain relief portion (304), handle (300) need not. In variations that include a strain relief portion (304), the strain relief portion (304) may stretch, compress, or otherwise deform to help reduce the strain placed on elongate body (304) by handle (300). This deformation may or may not be reversible. Generally, the strain relief portion (304) may be attached to both handle (300) and elongate body (304). When a force pushes, pulls, or twists elongate body (304) relative to handle (300), the strain relief portion (304) may resist this movement and thus a portion of the force may cause the strain relief portion to stretch, compress, or otherwise deform as mentioned above. The deformation of the strain relief portion (304) may act to reduce the relative movement between elongate body (304) and handle (300), which may help minimize the likelihood of the elongate body (304) disengaging from handle (300). Strain relief portion (304) may have any suitable size, shape, or configuration.

Additionally, while shown in FIG. 3A as having an interconnect (314), handle (300) need not. In variations that include an interconnect (314), interconnect (314) may be attached to elongate body (304), and may align the various lumens of elongate body (304) within handle (300). For example, in variations where handle (300) comprises a guidewire introducer (312), interconnect (314) may align guidewire introducer (312) with a working lumen (not shown) in elongate body (304). Interconnect (314) may align any number of device components with any number of lumens in elongate body (304).

While handle (300) is shown in FIGS. 3A and 3B to have a guidewire introducer (312), it may have any number of introducers or guides for introducing devices, fluids, or other components into elongate body (304). Indeed, handle (300) may have a guide to introduce one or more working devices such as a tissue grasper, a tissue ablator, cutting tool, visualization device, a combination thereof, or the like, into a lumen in elongate body (304). In other variations, handle (300) may include an introducer to provide flushing, drug delivery, vacuum, or the like through a lumen in elongate body (304).

Furthermore, while shown in FIG. 3A as having a snare lock (306), handle (300) need not. In variations that include a snare lock (306), snare lock (306) may be used to prevent snare control (308) from being moved relative to handle (300). Thus, in order to manipulate a snare loop assembly (not shown) a user must first depress snare lock (306) to release snare control (308). Once snare control (308) is released, a user may push snare control distally or pull snare control proximally to open or close the snare loop assembly. When a user stops depressing snare lock (306), snare control (308), and with it the snare loop assembly, may again be locked in place. In other variations, handle (300) may have one or more features to prevent snare control (308) from being accidentally actuated. In some of these variations, snare control (308) may be configured such that it cannot slide relative to the handle unless a user first depresses the snare control itself. In other variations, the snare control (308) comprises a button or other control that must first be manipulated before the snare control (308) may be actuated. In still other variations, the snare control (308) may be freely actuated, but may be locked into place by depressing either a button, other control, or the snare control (308) itself.

Once the snare loop assembly is properly closed, suture fob (310) may be detached from the handle to tighten the suture loop (not shown). As suture fob (310) is pulled away from handle (300), suture fob (310) may pull suture through a suture knot (knot shown) to tighten the suture loop. As the suture loop is tightened, any excess suture held in the elongate body may be removed from the suture loop. Once this slack has been removed, the user may continue to pull suture fob (310) to disengage the suture loop from the snare loop assembly. Once disengaged from the snare loop assembly, the suture loop may be further tightened to ligate the enclosed tissue. The direct connection of suture fob (310) to suture (318) may provide tactile feedback to the operator to indicate the various stages of a closing procedure. More specifically, a user may experience different resistances when pulling suture fob (310) that may correspond to different stages of suture loop tightening. For example, a user may experience a given resistance when removing excess suture (318) from the suture loop. In variations where the closure device comprises a suture hook (not shown), the resistance may change when the suture (318) is released from the suture hook. Additionally, the resistance may change once all of the excess suture has been removed from the suture loop, once the suture loop starts being released from the snare loop assembly, and once the suture loop is completely released from the snare loop assembly.

Additionally, in some variations it may be desirable to ensure that a user may only apply a given force to the suture loop. If a suture loop is tightened too much, it may damage the ensnared tissue. As such, in some variations a suture fob (310) may be configured to break away from suture (318) upon application of a predetermined force (for example, between about 8 lbs and about 10 lbs) to suture fob (310). In this way, the device may be configured such that a user may tighten a suture loop using a suture fob (310) without damaging the ensnared tissue, as the suture fob (310) may be configured to separate from the suture prior to damaging tissue.

Suture (318) may additionally include one or more visual markers (e.g., a colored coating) to indicate when the excess suture (318) has been removed from the suture loop. For example, a portion of suture (318) may have a colored marker located a certain distance from suture fob (310). The distance between the colored marker and the suture fob (310) may correspond to the amount of excess suture in the suture loop when the snare loop assembly is closed. A user may then pull suture (318) out of handle (300) using suture fob (310). When the colored marker becomes visible outside of handle (300) (or through a window in handle (300)), a user may know that the excess suture has been removed. Because the amount of excess suture may be dependent on the size of the loop formed by snare loop assembly, and because the size of the loop formed by snare loop assembly may be changed by snare control (308), in some instances the one or more visual markers on the suture (318) may correspond to one or more visual markers on snare control (308).

Additionally, suture (318) may be connected to suture fob (310) in any suitable manner. In some variations, such as that shown in FIG. 3B, one end of suture (318) may be connected directly to suture fob (310). In some of these variations, suture (318) may pass through a channel in suture fob (310), and may be knotted such that the resulting knot engages suture fob (310). In others of these variations, suture (318) may be clipped, grasped, or otherwise attached to suture fob (310). In other variations, suture fob (310) may comprise a pulley (not shown) that engages suture (318). In these variations, the end of suture (318) may be attached to another structure in handle (300), such as interconnect (314), and the pulley may slidably engage the suture (318). Because the suture is doubled-back over the pulley, a user may need to pull a suture fob (310) a shorter distance to achieve the same amount of tightening. For example, when a user withdraws a suture fob one inch, the pulley may also be withdrawn one inch. During this withdrawal, the pulley may pull more suture (318) into handle (300). For each inch that pulley moves, about two inches of suture are pulled into handle (one inch for each portion of suture (318) on either side of the pulley), and thus a user need only move suture fob (310) half the distance to achieve the same level of tightening.

Figure 4:
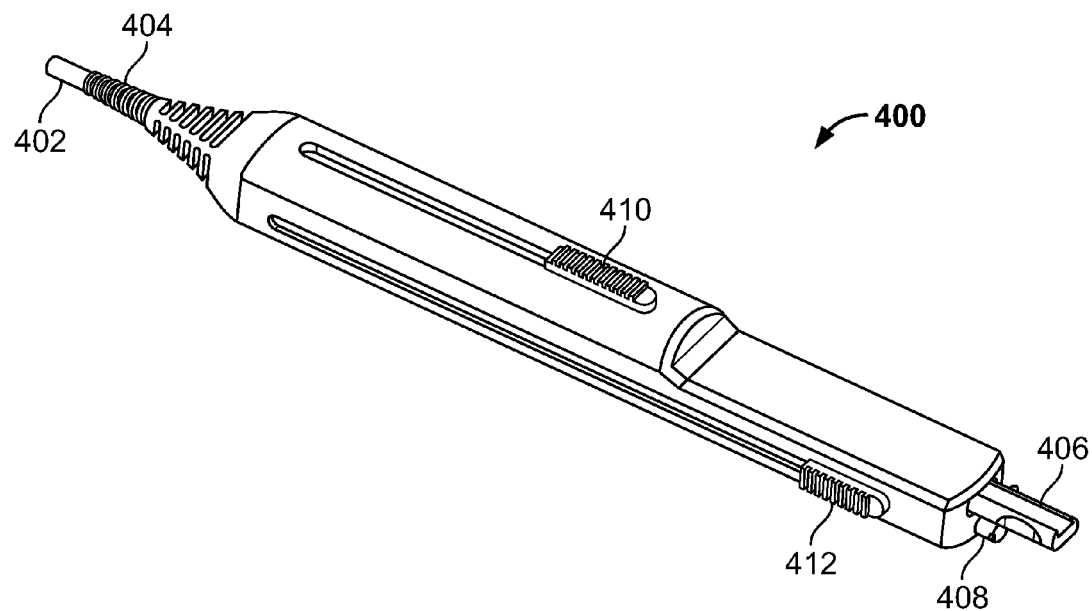
FIGS. 4-9 are perspective views of variations of handles suitable for use with the devices described here.

In some instances, it may be desirable to remove at least a portion of the excess suture without having to first disengage the suture fob. For example, FIG. 4 shows a perspective view of one variation of handle (400) attached to elongate body (402). Shown there is strain relief portion (404), suture fob (406), guidewire introducer (408), snare control (410), and suture fob control (412). Generally, snare control (410) may attach to a snare (not shown) to control a snare loop assembly (not shown), as described above. In some variations, snare control (410) may be configured to lock in place when not being actuated. In these instances, the snare control (410) may be unlocked in any number of ways, such as by depressing snare control (410) or by depressing a snare lock (not shown). In some of these variations, when snare control (410) or snare lock is no longer being depressed, snare control (410) is again locked into place.

In the variation shown in FIG. 4, suture fob (406) may be moved into and out of handle (400) by suture fob control (412). Suture fob (406) may be attached to a suture (not shown) in any manner as described above. Generally, the closure device is initially configured such that the suture fob control (412) is positioned near the distal end of handle (400), and suture fob (406) is entirely contained within handle (400). Suture fob control (412) may have one or more locking features like those described with respect to the snare control (410) above. Once the snare loop assembly has been closed around a target tissue using snare control (410), suture fob control (412) may be pulled proximally to the position shown in FIG. 4, to remove excess suture from the suture loop. Because movement of suture loop handle (412) is limited by the length of the track in which it sits, the length of this track may determine the amount of suture that may removed from the suture loop. In other variations, the handle (400) may comprise one or more features (e.g., stops) that limit the amount that suture fob control (412) may move. Thus the amount of suture pulled by suture fob control (412) may be dependent on the track in which suture fob control (412) is disposed, as well as the manner in which the suture is attached to the suture fob (406). As such, handle (400) may be configured to remove a predetermined amount of excess suture from the suture loop (not shown) when suture fob control (412) is actuated. Once suture fob control (412) has been moved to the position shown in FIG. 4, suture fob (406) may project out of the end of handle (400) and may be disengaged from handle (400). Once disengaged, the suture fob (406) may be pulled to remove any remaining excess suture from the suture loop, and then may pulled to remove the suture loop from the snare loop assembly. Once the suture loop has been released from the snare loop assembly, the suture fob (406) may be used to further tighten the suture loop and ligate tissue.

Figure 5:
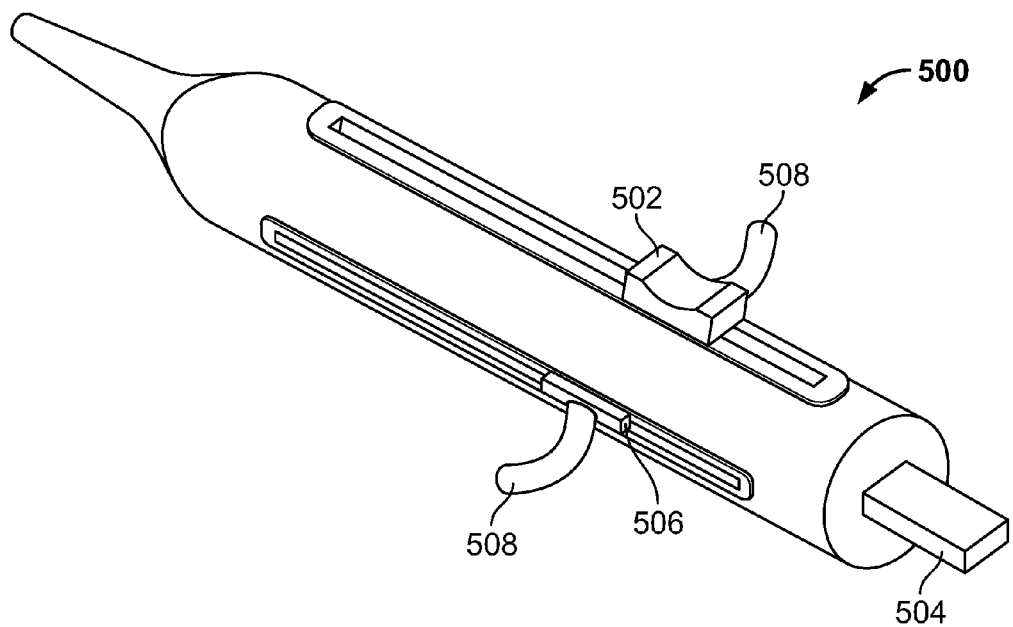

In some variations, a suture fob control has one or more features to help facilitate actuation of the suture fob control. FIG. 5 shows one such variation of a handle (500). Shown there is handle (500) with snare control (502), suture fob (504), and suture fob controls (506) with extensions (508). Snare control (502) and suture fob controls (506) may work in any suitable manner as described above. Extensions (508) may be any suitable structure or protrusion attached to, formed in, or formed upon one or more suture fob controls (502) that provide a surface that can be grasped, gripped, or otherwise contacted by a user to facilitate actuation of the suture fob controls (506). Extensions may have any suitable size, shape, configuration, and orientation. For example, in the variation shown in FIG. 5, extensions (508) are configured to allow a user to hold and actuate the handle (500) in a "syringe-like" fashion.

Figure 6:
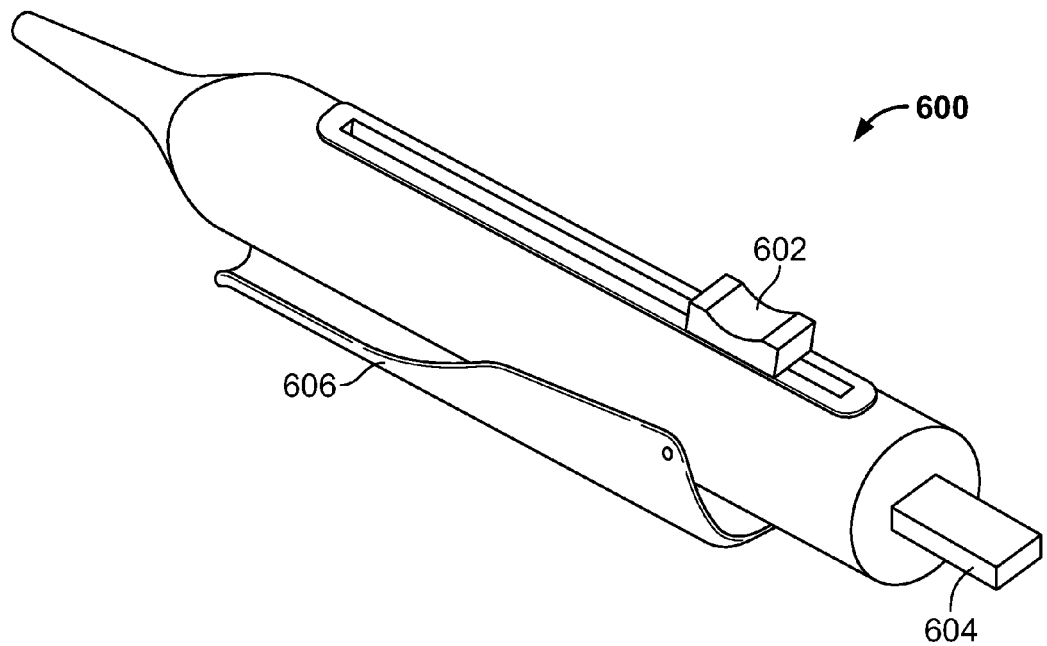

In other variations, a handle may have one or more alternative mechanisms to help remove excess suture from a suture loop. FIG. 6 shows one such variation of handle (600) comprising snare control (602), suture fob (604), and squeeze grip (606). To remove excess suture from a suture loop, a user may repeatedly compress squeeze grip (606). When a user compresses squeeze grip (606), squeeze grip (606) may pull suture from suture loop into handle (600). In some of these variations, compressing squeeze grip (606) may rotate a suture reel (not shown), which may collect suture as it rotates. Once a sufficient amount of suture has been removed from the suture loop, suture fob (604) may be disengaged to release suture loop from the snare loop assembly, as described above.

Figure 7:
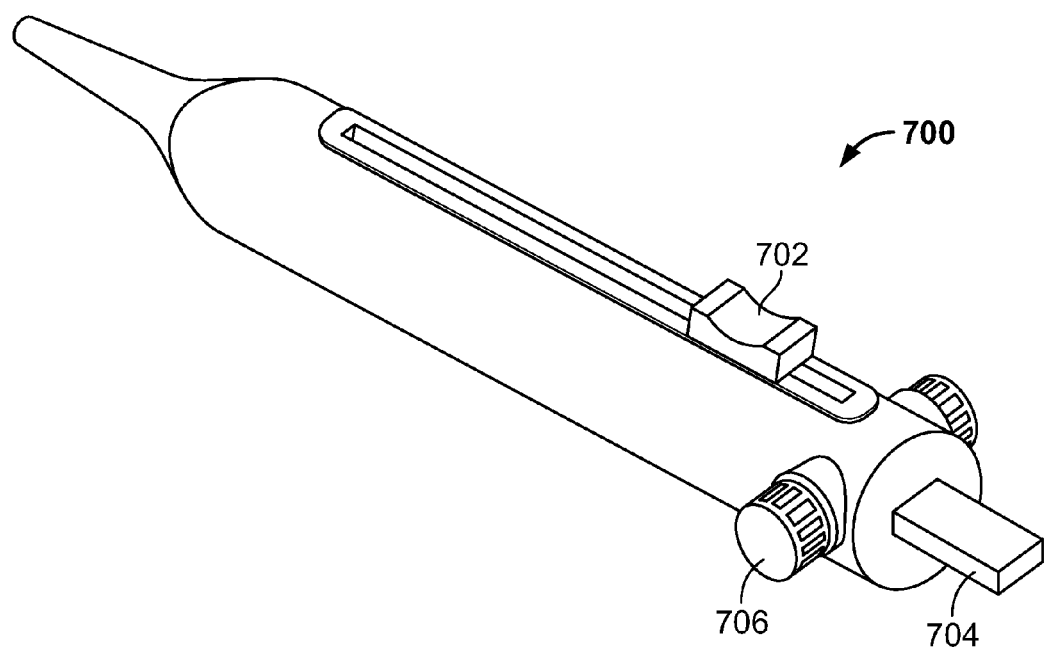

FIG. 7 illustrates another variation of handle (700). Shown there is handle (700) comprising snare control (702), suture fob (704), and suture knob (706). In these variations, suture knob (706) may be rotated to remove excess suture from a suture loop. In some of these variations, suture knob (706) may rotate a suture reel, which collects suture as it rotates. In other variations, rotating suture knob (706) may move suture fob (704) into and out of handle (700), as described above in relation to FIG. 4. Suture knob (706) may have one or more visual indicators to indicate how much suture has been removed from suture loop. For example, specific distance markings may be placed on one or more surfaces of suture knob (706). Handle (700) may have one or more reference markers (not shown). The distance markings on suture knob (706) may be configured such that each distance marking on suture knob (706), when aligned with the reference marker on handle (700), may correspond to the amount of suture that has been removed from the suture loop. For example, before the suture knob has been turned, a distance marking of "0" on suture knob (706) may be aligned with the reference marker, and may indicate that no suture has been removed from the suture loop. When the suture knob has been rotated a half-rotation, a distance marking of "3" on the suture knob (706) may be aligned with the reference marker on handle (700), and may indicate that 3 centimeters of suture has been removed from the suture loop. The specific distance markings on the suture knob (706) may depend on how much suture is removed from a suture loop as the suture knob (706) is rotated.

In other variations, a user may not be able to rotate suture knob (706) beyond a certain point. This feature may prevent a user from over-tightening the suture loop or unintentionally releasing the suture loop from the snare loop assembly. In some of these variations, the amount that suture knob (706) is able to rotate may correspond to the amount of excess suture in the suture loop. Generally, by only allowing a user to rotate a suture knob (706) a given distance, a user may know that they have removed a predetermined amount of suture from the suture loop. Depending on the configuration of handle (700), a user knows that all excess suture has removed from the suture loop, and the suture loop is ready to be released from the snare loop assembly. The suture fob (704) may then be released from the handle, and used to release suture loop from the snare loop assembly. Suture fob (704) may be released from handle (700) in any suitable way. In some variations, one or more buttons, knobs, or other controls may be actuated to release suture knob (704) from handle (700). By only allowing a user to rotate a suture knob (706) a given amount, the steps of tightening the suture loop and releasing the suture loop may be divided into two discrete steps, and thus a user does not to release the suture loop immediately after removing excess suture therefrom. This gives a user the ability to remove excess suture from the suture loop, and then to release the suture loop at his or her leisure. This in turn may provide an additional level of freedom to the user, who may want to attend to other matters between tightening the suture and releasing it from the snare loop assembly.

Figure 8:
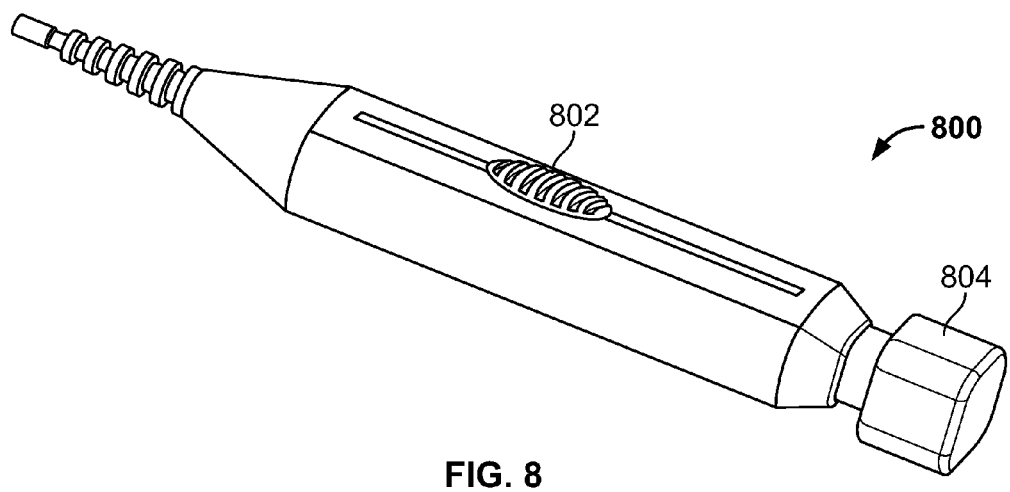

In some variations, a suture knob may be disengaged from the handle to act as a suture fob. FIG. 8 depicts one such variation of handle (800) comprising snare control (802) and suture knob (804). Suture knob (804) may have any suitable configuration, as described in U.S. patent application Ser. No. 12/055,213. Generally, suture knob (804) may be rotated to remove excess suture from a suture loop. In some variations, suture knob may only be rotated a certain amount, as described above. This may correspond to the amount of excess suture that is disposed in the suture loop. In some variations, one or more visual indicators, such as those described above, may inform a user how much suture has been removed from the suture loop. In some variations, the suture knob (804) may be configured to only require a certain amount of force by a user in order to rotate suture knob (804). In other variations, the force required to rotate the suture knob (804) may be determined by the resistance provided by the suture loop, and thus may provide a user with tactile feedback while rotating the knob.

Once the suture knob (804) has been rotated to remove excess suture from the suture loop, the suture knob may be disengaged from handle (800) to act as a suture fob, as described above. In some variations, suture knob (804) may automatically disengage from handle (800) once suture knob (804) has been rotated a certain amount. In some of these variations, suture knob (804) may comprise threading (not shown) that may engage handle (800). When suture knob (804) is rotated a certain amount, it may become "unscrewed" and release suture knob (804) from handle (800). In other variations, suture knob (804) may automatically disengage from handle (800) when the suture loop is subjected to a pre-determined force. In some of these variations, as the suture loop is tightened, it may pull one or more switches, levers, or other controls that disengages suture knob (804) from handle (800). In still other variations, the handle (800) may comprise one or more buttons, knobs, or levers that may be activated to release the suture knob (804) from the handle (800). Additionally, while shown in FIG. 8 to have a square suture knob (804), suture knob (804) may be of any suitable size or shape (e.g., square, rectangle, circle, oval, triangle, etc.).

Also provided here are ergonomically-improved handles. In some variations, the handle bodies may be shaped to contour to one or more portions of a user's hand. In other variations, the handles described here may have widths greater than their heights. These variations may have any suitable height to width rations, including, but not limited to about 1:1.5, about 1:2, about 1:2.5, about 1:3, or the like. When a user places one of these handles down on a surface, he or she may be more likely to place it on the wider base as opposed to one of the narrower sides. This may be beneficial in preventing device complications, such as rotation of the snare loop assembly, elongate body, or handle during a procedure, which may either damage the target tissue or interfere with the functioning of the closure device. If a user is less likely to place a handle on one of its narrower sides when setting the handle on a tray or another surface, then he or she may be less likely to overly rotate the handle during a procedure.

Figure 9:
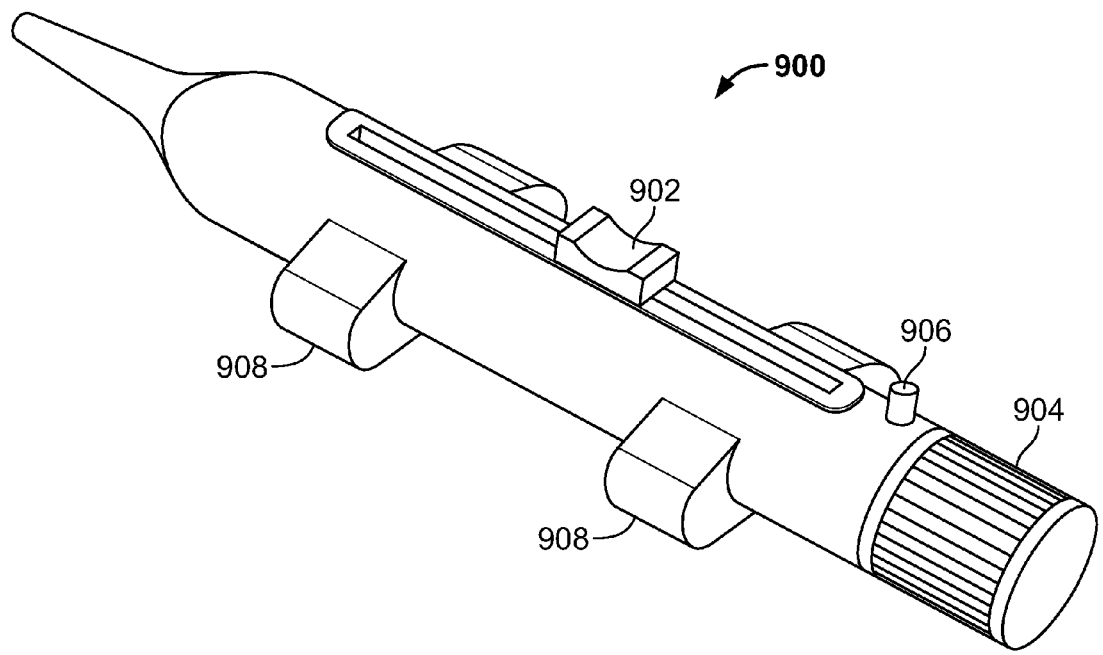

In other variations, the handle may comprise one or more protrusions that may help ensure the device is laid down with a particular orientation. FIG. 9 shows one such variation of handle (900) comprising snare control (902), suture knob (904), suture knob release (906), and protrusions (908). Protrusions (908) may act to help ensure that handle (900) is only placed with a particular side down. While shown as having four separate protrusions (908), handle (900) may have any suitable number of protrusions (908), and each protrusion may have any suitable size and shape.

Although the foregoing invention has, for the purposes of clarity and understanding been described in some detail by way of illustration and example, it will be apparent that certain changes and modifications may be practiced, and are intended to fall within the scope of the appended claims. Additionally, it should be appreciated that the closure devices described here may comprise any combination of device components and features described above.

Methods

Methods for closing the left atrial appendage are also described here. It should be appreciated that any of the devices described above may be used in conjunction with one or more of the methods described here or those described in U.S. patent application Ser. No. 12/055,213. Generally, methods described here comprise accessing the left atrial appendage. Once access has been achieved, a closure device (such as those described above) may be advanced to the left atrial appendage. In some variations, the closure devices may be advanced and positioned with the help of one or more guide devices and/or one or more stabilizing/positioning devices (e.g., an expandable member or the like). The closure device may be used to ensnare and close the left atrial appendage. A suture loop or other closure element may be tightened and released from the closure device to hold the left atrial appendage in closed configuration. The closure device may be withdrawn, and a portion of the suture may be severed. These steps will be described in more detail below.

As mentioned above, some variations of the methods described here may comprise gaining access to the left atrial appendage. In some variations, the methods for closing the left atrial appendage include accessing the left atrial appendage from both the inside of the heart and the outside of the heart. To access the inside of the heart, the vasculature is typically used. For example, access may be obtained via one or several of the various veins or arteries (jugular, femoral, carotid, etc.). In some variations, the heart is accessed on the inside via the common femoral vein (e.g., the left common femoral vein) using a standard Seldinger technique with a needle. An introducer wire may then be advanced through the needle, followed by an introducer sheath. The introducer wire may then be removed. In some variations, a guiding catheter sheath may be placed as an alternative to an introducer sheath or the initial sheath may be replaced with a guiding catheter sheath.

Using fluoroscopy, an angiogram performed through the sheath, a catheter placed through the sheath, a guiding catheter sheath, or any combination thereof, may be performed to observe anatomical characteristics and considerations of the access route for the purpose of transseptal access into the left atrium (e.g., tortuosity, clots, devices, such as vena cava filters, etc.). Fluoroscopy, ultrasound, intracardiac echocardiography, extracardiac echocardiography, transesophageal echocardiography, or combinations thereof, may be used to help visualize transseptal access to the left atrium, and access to the left atrium may be obtained using standard trans septal access techniques.

For access to the heart from the outside, a subthoracic access point may be used. The access point is typically identified based on patient anatomical characteristics. In some variations, the access point may be any suitable location (e.g., intercostal access via a sternotomy, thoracostomy, or thoracotomy, right of the xiphoid process and pointed towards the patient's left shoulder, or in the costal cartilage or xiphoid process itself). Once the access point has been determined, a needle (e.g., a 17G Tuohy needle) may be advanced using standard pericardiocentsesis techniques under fluoroscopic guidance. After access to the pericardium has been obtained, a guidewire may be advanced through the needle under fluoroscopic visualization within the pericardiac sac. The needle may then be removed. Access to the pericardial space has thus been obtained.

In other variations, the left atrial appendage may be closed off using the systems and devices described here without performing both access procedures as described above. For example, in some variations the methods comprise advancing a first guide having a proximal end and a distal end into the left atrial appendage, through the left atrial appendage, and out of the left atrial appendage, such that one of the proximal or distal ends is within the vasculature, and one of the proximal or distal ends is within the subthoracic space.

By virtue of gaining access to the left atrial appendage, one or more guides having alignment members may be advanced to the left atrial appendage. These guides may be any suitable guide, such as those described in U.S. patent application Ser. No. 12/055,213. For example, first and second guides having alignment members may be used to guide the procedure. The alignment member may be any suitable alignment member (e.g., interconnecting elements, one or more vacuum members, radiopaque or echogenic markers, members that are configured to produce an audible response, magnets, etc.). In some variations, the alignment members are magnets located at the distal ends of the guides. The magnets may be made from or comprise any suitable magnetic material, e.g., a rare earth magnet, such as neodymium-iron-boron, cobalt-samarium, or other powerful fixed magnet elements. These guides may be used for guiding additional tools and/or devices to the left atrial appendage.

For example, in some variations, a first guide may be advanced into the left atrial appendage, while the second guide may be advanced into the pericardial space adjacent to the left atrial appendage. Either of these guides may be advanced under any of a variety of visualization techniques, e.g., fluoroscopic visualization, ultrasound visualization, some combination thereof, etc. Once the first and second guide members have been advanced to the left atrial appendage, one or more positioning and/or stabilizing elements (e.g., balloons or other expandable structures) may be advanced over or in conjunction with the first guide (e.g., it may be coupled to or be part of the first guide) and into the left atrial appendage. Similarly, a closure device may be advanced over the second guide to the exterior of the left atrial appendage. It should be appreciated that the closure device may be any of the closure devices described above.

When placed in the left atrial appendage, the positioning element may be used to help position the snare loop assembly of a closure device. In some variations, an expandable structure may be inflated or otherwise expanded in or near the opening of the left atrial appendage and the snare loop assembly of the closure device may be closed around the left atrial appendage distally of the expandable structure. In these variations, the expandable structure may help position the closure device away from the Coumadin ridge. In other variations, the expandable member may be expanded inside of the left atrial appendage. In some of these variations, when the expandable member is expanded, the left atrial appendage may become distended and its shape changed from roughly conical to roughly spherical, thus better defining the junction between the left atrial appendage and left atrium. In addition, the expandable member in its expanded state may be at a pressure much greater than that of the left atrium proper, resulting in a significant differential in tension between the left atrial appendage and the left atrium. In these variations, the expandable member may help position the closure device near the base of the left atrial appendage. In still other variations, one expandable structure may be expanded in or near the opening of the left atrial appendage while a second expandable structure may be expanded inside of the left atrial appendage. In these variations, the snare loop assembly of the closure device may be closed around the left atrial appendage between the two expandable structures, which may help ensure correct device positioning.

It should be appreciated that the expandable structure may be any suitable expandable structure. In some variations, one or more the expandable structures may be a balloon or another inflatable structure. In some of these variations, the balloon or balloons may be attached to a catheter. In some variations, the balloon or inflatable structure may be configured to be detached in an expanded state inside of the left atrial appendage. In other variations, the expandable structure may comprise an expandable mesh or cage structure. This mesh may be self-expanding or mechanically expandable, and may be made from any suitable material (e.g., platinum, nitinol, stainless steel, Dacron wool, PTFE, combinations thereof, or the like). Again, the expandable mesh or cage structure may be configured to be detached in an expanded state in the left atrial appendage, but need not be.

While the expandable member is in an expanded state, the snare loop assembly may be moved to an open configuration and may be placed around a portion of the left atrial appendage. Once placed around the left atrial appendage, the snare loop assembly may be closed around the left atrial appendage. In some variations, the snare loop assembly is placed around the left atrial appendage while the balloon is in its deflated or unexpanded stated, and then the balloon is expanded after the snare loop assembly is closed. In some instances it may be desirable to confirm proper closure of the appendage prior to tightening of the suture. If closure is not adequate or otherwise not desirable, the snare loop assembly may be opened, repositioned, closed, and then confirmed once again.

Once proper closure has been affected, the suture loop may be tightened to release the suture loop from the snare loop assembly. In some variations, the snare loop assembly may then be returned to an open configuration and the suture loop may be tightened again. This may act to help ensure that the suture loop is sufficiently tightened around the left atrial appendage. In some variations, a user may re-tighten the suture loop after waiting for a period of time. This waiting period may allow tissue to readjust and settle within suture loop, which may allow for a tighter closure of tissue. This period of time may be any suitable period of time, such as, for example, greater than about 30 seconds, greater than about a minute, or greater than about 2 minutes. After releasing the suture loop from the snare loop assembly, the closure device may be withdrawn. In some variations, it may be desirable to further tighten the suture loop after the closure device has been withdrawn. This may be accomplished with one or more additional devices (e.g., a knot pusher).

It should be appreciated that some or all of the guide member or positioning elements may be removed from the left atrial appendage at any suitable point or points during the methods. For example, in some variations, some or all of these structures may be removed from the left atrial appendage after closing the snare loop assembly but prior to releasing the suture loop from the snare loop assembly. In other variations, some or all of these structures may be removed after releasing the suture loop from the snare loop assembly. The suture loop may be further tightened after some or all of these elements are removed. In still other variations, one or more expandable members may be detached and may remain in the left atrial appendage. In these variations, the expanded member may act to displace blood from the left atrial appendage and to help keep additional blood from entering the left atrial appendage. When the expandable member comprises a balloon or inflatable structure, the balloon may be filled with any suitable substance, such as, for example, saline or one or more hydrophilic polymers (e.g., hydroxyethyl methacrylate).

In yet other variations, one of the guide members or other elements placed inside of the left atrial appendage may be configured to release one or more materials to the closed left atrial appendage prior to removal. This material may act to create haemostasis or embolization of the closed left atrial appendage, which may prevent the ingress and egress of blood from the closed left atrial appendage. Examples of suitable materials include, but are not limited to gelatins (e.g., gel foam), liquid embolic agents (e.g. n-butyle-2-cyanoacrylate, ethidol), gelatin microspheres (e.g., polyvinyl alcohol acrylic microspheres), or pieces of thrombotic materials (e.g., platinum, stainless steel, Dacron wool, combinations thereof or the like).

In some variations, it may be desirable to lock the suture knot in place once the suture loop has been tightened around the left atrial appendage. In some variations, the suture knot may be locked using one or more unidirectional locking structures, as described in more detail above. In other variations, the knot may be locked in place with one or more bioglues or other biocompatible adhesives (e.g., cyanoacrylate). In still other variations, energy (e.g., RF energy, thermal energy, light energy, or the like) may be used to fuse the knot in place. In yet other variations, one or more portions of the suture knot may be configured to expand upon application of or exposure to one or more stimuli. For example, in some variations the suture may comprise collagen filaments that may be exposed to moisture when the suture is severed. Once the collagen is exposed to moisture, it may expand to lock the suture knot in place.

Once the suture loop has been properly placed, the suture may be severed in any suitable fashion, and at any suitable location along its length (i.e., from immediately adjacent to the knot at the left atrial appendage to just proximal to, or just distal to, the skin surface). In some instances it may be desirable to sever the suture at the knot itself (e.g., in instances where it is desirable to release tension on the suture entirely). The suture may be severed in any suitable manner, such as for example by mechanically cutting, or by the application of energy. For example, the suture may be severed with the application of light energy, thermal energy, RF energy, electrical energy, magnetic energy, electromagnetic energy, kinetic energy, chemical energy, and combinations of any of the above.

We claim:

1. A tissue closure device comprising:
   an elongate body;
   a snare comprising a snare loop that at least partially extends outside of the elongate body, wherein the snare has a proximal end that is connected to a first member;
   a suture loop releasably coupled to the snare loop, and a suture hook comprising a spring, wherein a proximal end of the suture hook is attached to the first member and a distal end of the suture hook releasably retains a portion of the suture loop; and wherein the first member is moveable within the elongate body to move the snare and the suture hook.

2. The device of claim 1 wherein the first member comprises a hypotube.

3. The device of claim 1 wherein a proximal end of the spring attaches to the first member.

4. The device of claim 1 wherein the spring is disposed around the snare.

5. The device of claim 1 further comprising a sleeve having a first lumen and a second lumen, wherein the suture hook passes through the first lumen and the snare passes through the second lumen.

6. The device of claim 5 wherein the sleeve is fixed relative to the snare.

7. The device of claim 1 wherein the tissue closure device further comprises a retention member releasably coupling the suture loop to the snare loop.

8. The device of claim 1 wherein the elongate body comprises a first lumen and a second lumen.

9. The device of claim 1 wherein a distal end of the snare is releasably held in a tip portion of the elongate body.

10. The device of claim 9 wherein the distal end of the snare is connected to a frangible member, and wherein breaking the connection between the snare and the frangible member releases the snare from the tip portion.

11. The device of claim 1 wherein the suture loop comprises a suture knot, and wherein a tip portion of the elongate body comprises a recess for housing the suture knot.

* * * * *